(12) United States Patent
Lu et al.

(10) Patent No.: US 9,550,792 B2
(45) Date of Patent: Jan. 24, 2017

(54) POLYCYCLIC SUBSTITUTED PYRAZOLE KINASE ACTIVITY INHIBITORS AND USE THEREOF

(71) Applicant: China Pharmaceutical University, Nanjing, Jiangsu (CN)

(72) Inventors: Tao Lu, Jiangsu (CN); Yue Wang, Jiangsu (CN); Yadong Chen, Jiangsu (CN); Yi Lu, Jiangsu (CN); Zhanwei Wang, Jiangsu (CN); Qiaomei Jin, Jiangsu (CN); Taotao Yang, Jiangsu (CN); Guowu Lin, Jiangsu (CN); Qinglong Guo, Jiangsu (CN); Li Zhao, Jiangsu (CN)

(73) Assignee: SHANGHAI FOSUN PHARMACEUTICAL DEVELOPMENT CO., LTD., Shanghai (CN)

( * ) Notice: Subject to any disclaimer, the term of this patent is extended or adjusted under 35 U.S.C. 154(b) by 0 days.

(21) Appl. No.: 14/759,516

(22) PCT Filed: Jan. 7, 2014

(86) PCT No.: PCT/CN2014/070195
§ 371 (c)(1),
(2) Date: Sep. 1, 2015

(87) PCT Pub. No.: WO2014/108053
PCT Pub. Date: Jul. 17, 2014

(65) Prior Publication Data
US 2015/0368259 A1    Dec. 24, 2015

(30) Foreign Application Priority Data
Jan. 8, 2013    (CN) .......................... 2013 1 0005258

(51) Int. Cl.
| | | |
|---|---|---|
| *C07D 495/04* | (2006.01) | |
| *C07D 491/048* | (2006.01) | |
| *C07D 471/04* | (2006.01) | |
| *C07D 487/04* | (2006.01) | |
| *A61K 31/5377* | (2006.01) | |
| *A61K 31/496* | (2006.01) | |
| *A61K 31/519* | (2006.01) | |
| *A61P 35/00* | (2006.01) | |
| *A61P 35/02* | (2006.01) | |
| *A61P 37/00* | (2006.01) | |
| *A61P 25/28* | (2006.01) | |
| *C07D 493/04* | (2006.01) | |

(52) U.S. Cl.
CPC ........... *C07D 495/04* (2013.01); *C07D 471/04* (2013.01); *C07D 487/04* (2013.01); *C07D 491/048* (2013.01); *C07D 493/04* (2013.01)

(58) Field of Classification Search
CPC . A61K 31/519; A61K 31/5377; A61K 31/496
See application file for complete search history.

(56) References Cited

U.S. PATENT DOCUMENTS

| | | |
|---|---|---|
| 2003/0203922 A1 | 10/2003 | Patel et al. |
| 2006/0035908 A1 | 2/2006 | Lew et al. |
| 2006/0258658 A1 | 11/2006 | Bebbington et al. |
| 2011/0002879 A1 | 1/2011 | Curry et al. |
| 2015/0368259 A1 | 12/2015 | Lu et al. |

FOREIGN PATENT DOCUMENTS

| | | | |
|---|---|---|---|
| CN | 103012428 A | 4/2013 | |
| WO | WO 02/22601 A1 | 3/2002 | |
| WO | WO 02/22607 A1 | 3/2002 | |
| WO | WO 02/22608 A1 | 3/2002 | |
| WO | WO 02/068406 A2 | 9/2002 | |
| WO | WO 2004/094410 A1 | 11/2004 | |
| WO | WO 2005/012256 A1 | 2/2005 | |
| WO | WO 2006/032851 A1 | 3/2006 | |
| WO | WO 2006/077425 A1 | 7/2006 | |
| WO | WO 2006/077428 A1 | 7/2006 | |
| WO | WO 2006077425 A1 * | 7/2006 | ............ A61K 31/00 |
| WO | WO 2006/085685 A1 | 8/2006 | |
| WO | WO 2008/007113 A2 | 1/2008 | |
| WO | WO 2008/007122 A2 | 1/2008 | |
| WO | WO 2008/009954 A1 | 1/2008 | |
| WO | WO 2009/078432 A1 | 6/2009 | |
| WO | WO 2009/134658 A2 | 11/2009 | |
| WO | WO 2011/017009 A1 | 2/2011 | |
| WO | WO 2011017009 A1 * | 2/2011 | .......... C07D 471/04 |
| WO | WO 2011/079230 A2 | 6/2011 | |
| WO | WO 2014/108053 A1 | 7/2014 | |

OTHER PUBLICATIONS

Supplemental European Search Report of EP 14738057, dated Apr. 28, 2016.
International Search Report of PCT/CN2014/070195 mailed on Apr. 22, 2014, from the State Intellectual Property Office of the P.R. China.

* cited by examiner

*Primary Examiner* — Joseph Kosack
*Assistant Examiner* — Amanda L Aguirre
(74) *Attorney, Agent, or Firm* — Finnegan, Henderson, Farabow, Garrett & Dunner LLP

(57) ABSTRACT

The present invention relates to the field of medicinal chemistry, and in particular relates to 4-(five-membered heterocyclic pyrimidine/pyridine substituted) amino-1H-3-pyrazolecarboxamide derivatives, the preparation method thereof, pharmaceutical compositions containing these compounds and the medicinal use thereof, especially as protein kinase inhibitors for anti-tumor use.

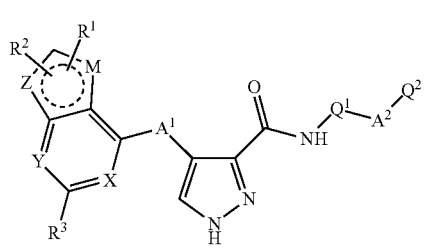

16 Claims, 1 Drawing Sheet

% inhibition of Kinase Activity (relative to DMSO control) shown in Radar Chart
I-1 compound
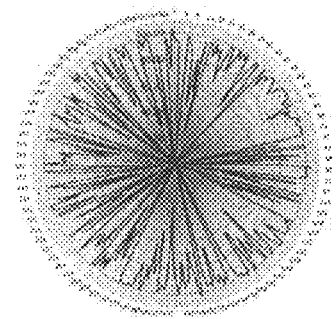
I-2 compound
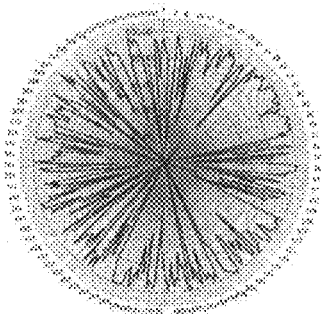
I-3 compound
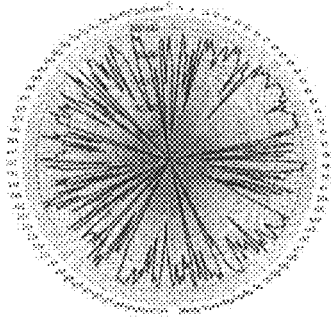
I-4 compound
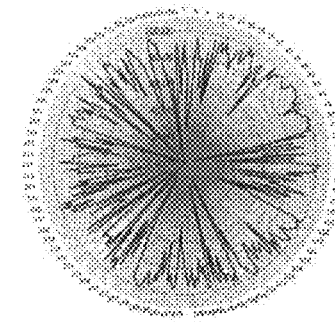
I-11 compound
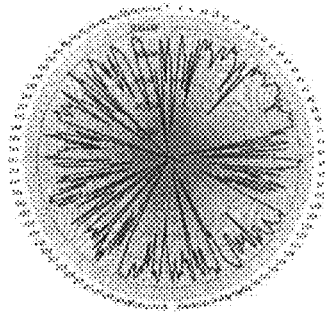
I-12 compound
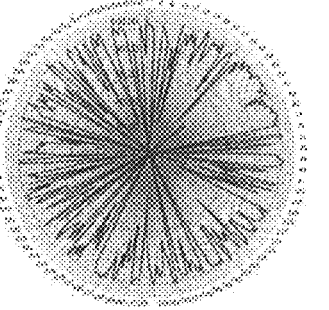
I-13 compound
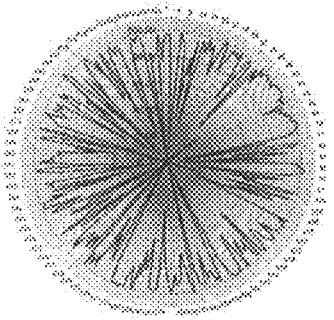
I-14 compound
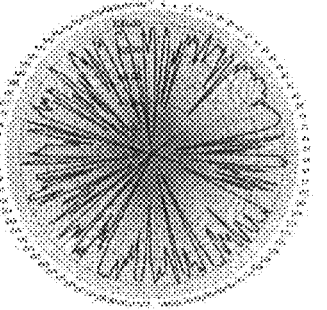
I-21 compound
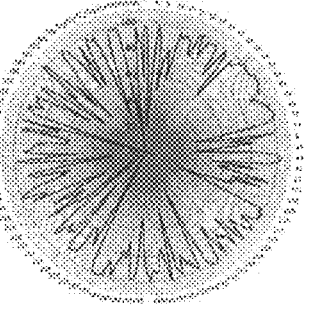
I-23 compound
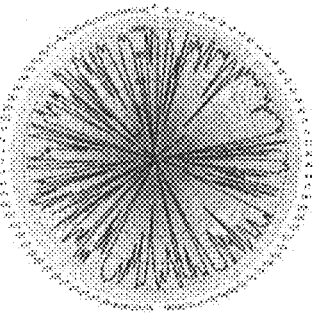
I-27 compound
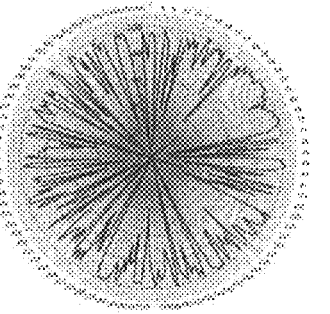
I-28 compound
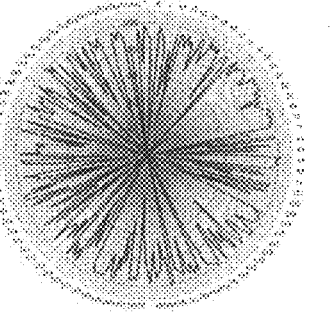

POLYCYCLIC SUBSTITUTED PYRAZOLE KINASE ACTIVITY INHIBITORS AND USE THEREOF

FIELD OF THE INVENTION

The present invention belongs to the field of medicinal chemistry and relates to 4-(five-membered heterocyclic pyrimidine/pyridine substituted)amino-1H-3-pyrazolecarboxamide derivatives, the methods for preparing the same and the pharmaceutical composition containing the same as well as their medical use, especially that of antitumor as protein kinase inhibitor.

BACKGROUND OF THE INVENTION

Under normal conditions, cell cycle is regulated by a group of related proteases, having different biological functions including inhibition or promotion of cell cycle, wherein most proteins that promote cell cycle belong to kinases. Kinases play crucial role in regulating protein for promoting important physiological function. Their major function in vivo is to transfer the phosphate of high-energy molecule adenosine triphosphate (ATP) to the receptor so as to regulate protein receptor activation or deactivation and finally regulate the cell cycle. However, it is found in many cancel cells that these kinases regulating the normal cell cycle will be suddenly out of control. Thus, it is believed that if these unregulated kinases could be suppressed, the proliferation of cancer cells will be controlled. In recent years, cyclin-dependent kinase (CDK), Aurora kinase, Polo-like kinase (PLK), kinesin (kinesins spindle protein, KSP) and checkpoint kinase (CHK) and some other new targets are found to be closely related to the cell cycle.

Among them, the co-activation of Aurora kinase in centrosome and CDK is essential for the initiation of mitosis. They are related to each other and promote mutually in regulating cell cycle and mitosis process. Corresponding inhibitors of these two inhibitors have been investigated and various compounds have been in clinical research, demonstrating good prospects for the development of anticancer drugs.

It has been found that almost all of the tumors are associated with cell cycle regulation disorder which may cause uncontrolled cell growth, impaired cell differentiation and abnormal apoptosis, and excessive activation of CDKs (cyclin-dependent kinases, CDKs) is one of the important reasons for these conditions. CDKs are important serine/threonine protein kinases, which does not exert biological activity per se until they are combined with cyclins. Once activated, the CDKs can catalyze substrate phosphorylation, actuate each phase of the cell cycle, accomplish the synthesis of DNA and mitosis in order, and finally induce the cell growth and proliferation. Meanwhile, CDKs can also bind with CDKs inhibitors (CDI) to play a negative regulatory role so as to inhibit cell cycle progression and prevent cell division. As CDKs are critical in the regulation of tumor cell proliferation and apoptosis, selective inhibition of the activity of CDKs in tumor tissues could play a positive role in treating tumors and malignant diseases. Thus, the study and screening of small-molecule inhibitors for CDKs is one of the hot fields for treatment of cancer and the development of new chemotherapy drugs.

CDK1, CDK2, CDK4 and CDK6 are the more important subtypes of CDKs in regulating the progression of cell cycle. Due to the fact that the disregulation of cell-cycle is a major cause of cancer, if the cell cycle can be prevented from entering into S phase, aberrant DNA replication would not occur. The process from the G1 to S phase is mainly regulated by CDK2/cyclin E, therefore CDK2 inhibitors can prevent cell cycle from entering into the S phase for further DNA replication. Moreover, in addition to the control of G1 to S phase, CDK2/cyclin A also controls S and G2 phase progresses throughout the cell cycle. It can be seen that CDK2 plays a very significant role in cell cycle, and therefore if the activity of CDK2 can be effectively inhibited, the cell cycle will be controlled and the uncontrolled proliferation of tumor cell will be suppressed.

In recent years, a number of small-molecule inhibitors of CDKs have been disclosed and most of them show good inhibitory activity against CDK2. They exert the inhibitory activity mainly by competitively binding to the ATP active site of CDKs.

Aurora family is a serine/threonine protein kinase. There are three kinds of Aurora kinase subtypes that are highly relevant in structure and functions in human cells: Aurora A, B and C. It is involved in the regulation of cellular mitosis, including centrosome duplication, bipolar spindle formation and chromosome rearrangement in the spindle, etc., and can accurately monitor the spindle checkpoint, abort wrong cell cycle progression and complete the repair process. During the progressing of cell cycle, Aurora kinases mainly act on the M phase, and start series of biochemical events of mitosis combined with CDKs.

Aurora A and Aurora B are closely related to tumor. Firstly, Aurora A is located on 20q13.2 while Aurora B is located on 17p13. Both of them are located in chromosomal segments of active translocations, deletions or amplification, meaning that they have a natural instability. These studies suggest that when Aurora A is overexpressed, it is a potential oncogene. The amplification of these two chromosomal regions is prevalent in tumor tissues of breast cancer and colorectal cancer, and cell lines of breast cancer, ovarian cancer, colon cancer, prostate cancer, neuroblastoma and cervical cancer. At present, there is few study on the carcinogenic effects of Aurora C.

Aurora A, B and C are highly homologous in catalytic region with only a short amino acid sequence differences in the terminal of regulating region and catalytic domain. Active sites where the inhibitors bind are located in the hinge region. The purine ring of ATP can be accommodated in a hydrophobic pocket of Aurora kinase and form a hydrogen bond with the amino acid residues in the hinge region. Aurora kinase inhibitors can competitively bind with the ATP binding site of Aurora kinase and also belong to ATP-competitive inhibitors.

It has been reported that in G2 terminal stage, microinjection of Aurora kinase antibody can significantly delay the mitotic initiation. Now the mechanism is thought to be that Aurora A kinase as downstream effector for the activated CDKs/cyclin complexes participates in a series of biochemical events for the initiation of mitosis. It forms positive feedback interactive activation loop with CDKs/cyclin complexes, that is, the CDKs/cyclin complexes firstly activate Aurora kinases and Aurora kinases in turn promote the complete activation of CDKs and facilitate the positioning within the nucleus of the complex. These two events are important for the initiation of mitosis. In short, during the cell cycle, the co-activation of Aurora kinase and CDKs on the centrosome is one of the essential conditions for the initiation of cell mitosis, in which they are mutually associated with each other in regulating the cell cycle and mitosis process. Thus, if the activities of Aurora kinase and CDKs can be inhibited simultaneously, the overgrowth of tumor cell can be dually inhibited. Therefore it is of great value to develop novel CDKs/Aurora multi-target inhibitors.

Throughout the cell cycle, in addition to the control of G1 to S phase, CDK2 also controls the cell processes of S and G2 phases. Thus, by the inhibition of CDK2, the normal replication of DNA in the cell cycle can be prohibited. While in the M phase, the regulation of cell mitosis mainly relies on Aurora A, which plays an irreplaceable role in centrosome duplication, bipolar spindle formation, chromosomal rearrangements and the like. Thus, it is believed that the inhibition of Aurora A can prevent cell mitosis. Therefore, search for multi-target small molecules targeting CDK and Aurora kinases simultaneously and affecting the cell cycle of cancer cells in multiple ways would be a better way to achieve the purpose of cancer treatment.

Hitherto, many crystal structures of CDK2 and Aurora A have been resolved, and the inhibiting mode of the inhibitors and target is very clear, which acts as the basis for structure-based drug design of multi-target inhibitors. By comparison, CDK2 and Aurora A kinase inhibitors competitively bind to the ATP-binding pocket, mainly bind with enzyme through hydrogen bonds and hydrophobic interactions. There are some common features for the action modes of the small molecule inhibitors with these two kinases and their co-efficacy regions are as follows: the three-dimensional structure and physicochemical properties such as hydrogen bonds, hydrophobic and hydrophilic spatial distribution are very similar for CDK2 and Aurora A: 1) hinge region (hinger): hinge region is the most important area for all ATP-competitive inhibitors, and in this area there are often two or three critical hydrogen bonds; and residues in these two kinases involved in the formation of the hydrogen bonds are Glu81 and Leu83 for CDK2, and Glu211 and Ala213 for Aurora A. Moreover, a number of hydrophobic planar segments often locate in the hinge region so as to ensure some hydrophobic effects. 2) hydrophobic region A: this region refers to the hydrophobic cavity formed between the hinge region and aspartic acid (Asp145 for CDK2 and Asp274 for Aurora A), which is located close to the region of the kinase motif DFG. Since the loop region has some flexibility, the selection of the hydrophobic structural fragments shows some diversity. 3) hydrophilic region: both of active sites of the two kinases contain a hydrophilic region, wherein the introduction of hydrophilic groups in this region will be of great significance for modulating the physicochemical properties of the compounds. The hydrophilic region of CDK2 is located in the vicinity of Gln85 while that of Aurora A is near Leu215. These highly overlapped pharmacodynamic effect regions allow us to design CDK/Aurora multi-target inhibitors. The multi-targeted drugs generated by overlapping of ligand molecules tend to have small molecular weight, good physical and chemical properties and much improved drug resistance.

In recent years, with the development of the study in respect of protein kinases, based on structure and gene sequence, the concept of protein family is constantly presented as a family of enzymes with similar structure and function and involved in a variety of signal transduction and cell regulation. Protein kinases can be classified into a plurality of sub-families based on the different phosphorylated substrates such as protein-tyrosine, protein-serine/threonine, lipids, etc. Protein kinases are characterized by their regulation mechanisms, including autophosphorylation, transphosphorylation with other kinases, protein-protein interactions, protein-lipid interactions, and protein-polynucleotide interactions. A single protein kinase can be involved in various regulating mechanisms. Protein kinases catalyze the δ-phosphate at ATP terminus and phosphorylate the side chain hydroxyl of serine, threonine or tyrosine residues, which regulate their substrate activity, mediate the majority of cellular signal transduction pathways and regulate many different cellular processes. The cellular processes include, but are not limited to, proliferation, differentiation, apoptosis, motility, transcription, translation and other signaling processes. Phosphorylation acts as a molecular switch, regulating the biological function of the target protein. Phosphorylation of target proteins occurs in response to a variety of extracellular signals, cell cycle events, environmental or nutritional stress, etc. The extracellular signals include hormones, neurotransmitters, growth and differentiation factors, etc. Specific protein kinase plays a role in signal transduction pathways which directly or indirectly activate or inactivate metabolic enzymes, regulatory proteins, receptors, cytoskeletal proteins, ion channels or pumps, or transcription factors. Uncontrolled signal transduction caused by protein phosphorylation control deficiencies relates to many diseases, including inflammation, cancer, diabetes, allergy/asthma, immune system diseases and disorders, central nervous system diseases and disorders as well as angiogenesis diseases and disorders.

The human protein kinome contains 518 members of protein kinases, including 90 tyrosine kinases, 388 serine/threonine kinases and 40 non-classical kinases. Based on phylogenetic analysis, Hanks and Hunter have categorized human protein kinases for several times. With the increase of cloned protein kinase members, their classification is more and more systematic and detailed. Based on the phylogenetic trees, they proposed a classification on the entire catalytic domain of protein kinase members published before June 1993. The phylogenetic tree contains four large kinase families: (a) AGC family, including the family of cAMP-dependent protein kinase (PKA and PKG family), protein kinase C family, B-adrenergic receptor kinase (BARK) family, ribosomal S6 kinase family and other related kinases: (b) CaMK family, including $Ca^{2+/-}$ calmodulin-regulated protein kinase family, Snfl/AMPK family and other related protein kinases; (c) CMGC family, including CDK family, Erk (MAP) kinase family, Glycogen synthase kinase 3 (GSK3) family, Casein kinase II family, Clk family and other related kinases; and (d) protein tyrosine kinase (PTK) family. The phylogenetic tree also includes a number of protein kinases that belong to none of the four families. Each large family could further be classified into subfamilies, and has at least one example like Abelson kinase (ABL), Akt/protein kinase B (Akt/PKB), epidermal growth factor receptor (EGFR), Fibroblast growth factor receptor (FGFR), mixed-lineage kinases (MLK), platelet-derived growth factor receptor (PDGFR), tyrosine kinase with immunoglobulin-like and EGF-like domains (TIE), vascular endothelial growth factor receptor (VEGFR). In addition to the primary structure, members of the same family are highly consistent in the topology, regulation mode and substrate specificity. Evolutionarily similar members have similar functionality.

CMGC is a serine/threonine protein kinase, and the phosphorylation sites mostly are located at serine or threonine in proline-rich environment. Members of this family have a large intervening sequences in X and XI functional subdomains. Because Dyrk (MNB), Dyrk2, Dyrk3 have high homology with Yak1, they are organized to a family. As a member of CMGC family, CDK was mentioned previously. CDK1, CDK2, CDK4 and CDK6 are mainly involved in the regulation of the entire cell cycle, while the other CDKs are associated with other biochemical processes. For example, in proper neuronal development, CDK5 is required and implicated in the phosphorylation of several neuronal proteins, such as Tau, NUDE-1, synapsin 1, DARPP32 and Munc18/Syntaxin 1A complex. Usually, neuronal CDK5 is activated by binding to p35/p39 protein. However, the activity may be disordered by binding with p25 (the truncated form of p35). Conversion of p35 to p25 and CDK5 activity disorder can be induced by ischemia, excitotoxicity and β-amyloid peptide. Therefore, p25 is related to the pathogenesis of neurodegenerative diseases like Alzheimer's disease, and is concerned as a direct target for the treatment of these diseases.

CDK7 is a nucleoprotein which has cdc2CAK activity and binds to cyclin H. CDK7 is a component of the TFIIH transcription complex with RNA polymerase II C-terminal domain (CTD) activity. Its biochemical pathways mediated by Tat are related with HIV-1 transcription regulation. CDK8 binds to the cyclin C and relates to the phosphorylation of RNA polymerase II CTD. Similarly, CDK9/cyclin-T1 complex (P-TEFb complex) relates to extension control of RNA polymerase II. PTEF-b also requires HIV-1 genome to interact with cyclin T1, through which it is transcripted and activated by virus trans-activated protein Tat. Therefore, CDK7, CDK8, CDK9 and P-TEFb complex are potential targets for anti-viral treatment.

The regulation of the CDK/cyclin complex activity at the molecular level requires a series of stimulation and inhibition of phosphorylation and dephosphorylation events. The phosphorylation of CDK is performed by a group of CDK activating kinases (CAK) and/or some kinases such as wee1, Myt1 and Mik1. The dephosphorylation is conducted by phosphatases such as cdc25 (a and c), pp2a, or KAP.

At the same time, it is discovered that the overexpression of cyclin D1 is related to esophageal cancer, breast cancer, squamous cancer and non-small cell lung cancer. In the pathogenesis of lung cancer, the inactivation of tumor suppressor genes is now a hot spot. Tumor suppressor gene p15/MTS2, which is referred to as p15 gene and encodes p15 protein, belongs to INK4 protein family. It acts on the CDK and cyclin complex, specifically inhibiting the activity of CDK4 kinase and CDK16 kinase, preventing the phosphorylation of R6 protein, restricting the cell process from G1 to S phase, and thus reducing cell proliferation.

Mitogen-activated protein kinase (MAPK) is another member of CMGG kinase family and a kind of serine/threonine protein kinase. It can transduce extracellular signals into cell and nucleus and regulate gene expression by the activation of transcription factors through conservative three level cascades (MAPKKK-MAPKK-MAPK). This pathway exists in most cells and is involved in a variety of cellular functions, such as cell movement, apoptosis, differentiation and proliferation of the cells and many other physiological processes. Four MAPK signal transduction pathways have been identified and each of them is highly specific with individual functions. To some degree, these signal pathways have some crosstalk. The research with inhibitors and activators on various signal pathways can not only promote understanding the mechanism of signal pathways, but also create new opportunities for diagnosis and treatment of diseases. ERK signal pathway is one of the most thoroughly studied pathways, wherein MEK is a key enzyme in the Ras-Raf-MEK-ERK signal transduction pathway, regulating cell responses according to different growth signals. MEK has seven subtypes, which phosphorylate and activate downstream MAPKs respectively. MEK1 and MEK2 activate ERK; MEK3 and MEK4 activate p38; and MEK5 and MEK6 activate JNK. Therefore, MEK1/MEK2 is commonly used as a cancer treatment target to develop promising anticancer drugs in the ERK signal pathway research. p38/MAPK signal pathway is an important branch of the MAPK pathway, which can be activated by stressors (such as osmotic shock, UV, hypoxia), cytokines, insulin and growth factors, and can even be activated in normal immune and inflammatory reactions. Meanwhile, study of another signal pathway p38, the main target for the treatment of rheumatoid arthritis in clinical research, also becomes a hot spot in recent years. c-Jun N-terminal kinase (JNK)/stress-activated protein (SAPK) signal pathway is an important family member of MAPKs in which c-Jun is a member of AP-1 transcription factor complex, involved in the control of cell proliferation, transformation, survival and apoptosis. JNK also phosphorylates p53 and some non-nucleoproteins. The phosphorylation of target protein mediated by JNK is very important, which can induce the gene expression of IL, VEGF, COX-2, MMP-9, heme oxygenase-1, ICAM-1, NCX1, GnRHR genes and other cytokines. JNK signal pathway is involved in inflammation and autoimmune diseases such as rheumatoid arthritis, irritable bowel syndrome and atherosclerosis. ERK5/BMK1, the K5/big mitogen-activated protein kinase (BMK1) signal pathway, is the latest discovered pathway in the MAPK family. Its extracellular stressors include high sugar, low oxygen, blood flow shear stress, reactive oxygen species (ROS), osmotic pressure and a variety of mitogens like EGF, NOF and etc. ERK5/BMK1 also follows the MAPK cascade, MEKK 2/3 (MAPK-KK)-MEK5 (MAPKK)-BMK1/ERK5 (MAPK). Once activated, ERK5 moves from cytoplasm into nucleus, and phosphorylates a large number of downstream targets which include MEF2C, c-Myc, Bim, AP-1 and etc. ERK5 plays an important role in cell survival, proliferation and differentiation. The current study found that it is closely related to the pathological processes of diabetes, kidney disease, liver fibrosis and tumors.

Glycogen synthase kinase-3 (GSK-3) is a serine/threonine kinase that occurs as two ubiquitously expressed isoforms in humans (GSK-3α and GSK-3β). GSK-3 is involved in embryonic development, protein synthesis, cell proliferation, cell differentiation, microtubule dynamics, cell motility, and cell apoptosis. Likewise, GSK-3 is involved in the progression of disease states such as diabetes, cancer, Alzheimer's disease, stroke, epilepsy, motor neuron disease and/or head trauma. Phylogenetically, GSK-3 is most closely related to CDKs.

Forming a part of the mammalian insulin response pathway, GSK-3 is able to phosphorylate, and thereby inactivate glycogen synthase. Upregulation of glycogen synthase activity and thereby glycogen synthesis through inhibition of GSK-3 has thus been considered as a potential means of combating type II, or non-insulin-dependent diabetes mellitus (NIDDM): a condition in which body tissues become resistant to insulin stimulation. Inhibition of GSK-3, e.g. by inactivation of the "mammalian target of rapamycin" protein (mTOR), can upregulate protein biosynthesis. Finally, there is some evidence for regulation of GSK-3 activity via the MAPK pathway through phosphorylation of GSK-3 by kinases such as mitogen activated protein kinase activated protein kinase 1 (MAPKAP-K1 or RSK). These data suggest that GSK-3 activity may be modulated by mitogenic, insulin and/or amino acid stimuli.

In addition, GSK-3β is a key component in vertebrate Wnt signaling pathway. This biochemical pathway has been shown to be critical for normal embryonic development and regulation of cell proliferation in normal tissues. In response to Wnt stimulation, GSK-3 becomes inhibited, which can cause GSK-3 substrate (e.g. Axin, the adenomatous polyposis (APC) gene product and β-catenin) dephosphorylation. Aberrant Wnt pathway regulation is related to many cancers. APC and/or β-catenin mutations is very common in colorectal cancer and other tumors, which shows that β-catenin is very important in cell adhesion. Thus, GSK-3 could also modulate cell adhesion processes to some degree. Apart from the biochemical pathways already described, there are also data showing GSK-3 regulates cell division via phosphorylation of cyclin-D1, and phosphorylates transcription factors such as c-Jun, CCAAT/enhancer binding protein α (C/EBPα), c-Myc and/or other substrates such as nuclear factor of activated T-cells (NFATc), heat shock factor-1 (HSF-1) and the c-AMP response element binding protein (CREB). Regardless of the tissue specificity, GSK-3 also plays a role in regulating cellular apoptosis. The role of GSK-3 in modulating cellular apoptosis, via a pro-apoptotic mechanism, may be of particular relevance to medical conditions in which neuronal apoptosis can occur. Examples are head trauma, stroke, epilepsy Alzheimer's disease and motor neuron diseases, progressive supranuclear palsy, corticobasal degeneration, and Pick's disease. It has been shown in vitro that GSK-3 is able to hyperphosphorylate the microtubule associated protein Tau. Hyperphosphorylation of Tau disrupts its normal binding to microtubules and may also lead to the formation of intra-cellular Tau filaments. It is believed that the progressive accumulation of these filaments leads to eventual neuronal dysfunction and degeneration. Inhibition of Tau phosphorylation by inhibiting GSK-3 may thus provide a means of limiting and/or preventing neurodegenerative effects.

Protein tyrosine kinases (PTKs), another important protein kinase family, catalyze γ-phosphate group of ATP to tyrosine residues of many important proteins, and therefore phosphorylate phenol hydroxyl group. In normal cells (except nerve cells), phosphorylation of tyrosine rarely occurs. Although phosphorylated tyrosine is only 0.5‰ of phosphorylated amino acids in body, it is demonstrated that tyrosine phosphorylation plays an important role in the regulation of many cellular processes. It is an important factor in signal transduction by transducing cell signals. Additionally, PTKs are involved in a series of cell functions and closely related to cell growth, differentiation and proliferation. PTKs also play a very important role in the growth and proliferation of malignant cells. Tyrosine kinase function disorders can lead to activation of its downstream signaling pathways and provoke disorders of cell proliferation, ultimately leading to tumor formation. Therefore, tyrosine kinase inhibitors are beneficial in cancer prevention and treatment.

PTKs can be classified into nonreceptor tyrosine kinases (NRTKs) and receptor tyrosine kinases (RTKs) according to whether they exist in cell membrane receptors. Up to now, 58 types of RTKs have been found. These protein kinases structurally possess a very similar catalytic region that consists of about 270 amino acids residues. RTKs are transmembrane proteins and are generally consisting of an extracellular domain, a transmembrane domain and an intracellular kinase domain. Clinical researches imply that these receptors and ligands thereof are closely relevant to many sorts of cancers. Over-expression of corresponding growth factors which are involved in cancers can lead to excess phosphorylation signals of tyrosine transduced into cells. Such growth factors like PDGF receptors (PDGF receptor α and β), colony-stimulating factor (CSF-I) receptor (CSF-1R, c-Fms), FLT-3 and c-kit, etc are relevant to many diseases such as cell proliferation and inflammation. Among them, FLT3 gene, located at the 13q12 chromosome, is an early hematopoietic growth factor gene found in 1991 and the encoded FLT3 receptor belongs to the third type of RTK receptors family. When extracellular domain of FLT3 receptor binds to its endogenous ligands, the homo- or heterodimer complex will be formed which will lead to activation of tyrosine kinase, opening active loop and making substrate protein bind to the ATP binding site. Consequently, substrate proteins are phosphorylated which leads to transduction of a series of downstream signals causing proliferation and differentiation of cells. FLT3 receptors are widely spread in hematopoietic stem/progenitor cells, thymus, lymph, placenta, brain, gonads and many other tissues. However, FLT3 gene mutation (mainly including internal tandem duplication mutations of the juxtamembrane domain and point mutations of tyrosine kinase domain) and over-expression can result in a variety of hematologic malignancy diseases such as acute myelogenous leukemia. As a result, FLT-3 becomes a hotspot in cancer treatment, particularly in hematological malignancies. Over-expression or mutation of FLT-3 leads to uncontrolled induction of FLT3 receptors and downstream channels which may cause activation of Ras. Hematological malignancies include leukemia, lymphoma (NHL), Hodgkin's disease (also known as Hodgkin's lymphoma) and myeloma like acute lymphoblastic leukemia (ALL), acute myelogenous leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large cell lymphoma (ALCL), immature lymphocytic leukemia (PML), juvenile Reap-monocytic leukemia (JMML), adult T-cell ALL, myelodysplasia with trilineage (AML/TMDS), mixed lineage leukemia (MLL), myelodysplastic syndromes (MDSs), myelodysplastic (MPD), multiple myeloma (MM) and spinal cord sarcomas.

Meanwhile, RTKs extracellular domain can bind to specific ligands such as growth factors, while their intracellular domains are phosphorylated. Signal pathways and biological processes mediated by RTKs are located in angiogenesis. It is shown that the pathway activated by RTKs is selected in angiogenesis. Activation of pathways such as via VEGFR or PDGFR can result in various procedures of angiogenesis like cell proliferation, migration, survival and vascular permeability that are closely related to a series of vascular diseases.

Currently, there are 32 nonreceptor tyrosine kinases (nRTKs) that continuously or temporarily exist in the cytoplasm, or bind to transmembrane protein in the cell. Thus, they are also known as cytoplasmic tyrosine kinase. In tumor tissues, nPTKs are often activated, promoting cell proliferation, resisting apoptosis and promoting tumor development and progression. nRTKs mainly contain 10 families: SRC, ABL, JAK, ACK, CSK, FAK, FES, FRK, TEC, SYK and etc. Cytokines can transduce signals through a variety of pathways to participate in the regulation of cell growth, differentiation and apoptosis. Generally, cytokine receptors do not contain RTKs domains in cytoplasm, but signal transductions mediated by the cytokine when binding to its receptor do exist in cytokine-targeted cells. Among them, Janus kinase (JAK) and its downstream STAT constitute an important signaling pathway and many cytokines can activate the JAK/STAT signaling pathway. When the cytokines bind to their receptors, conformational changes will occur in the cytoplasmic receptor, thereby activating associated JAK kinase family receptors. JAK kinase induces the activation of STAT by promoting its corresponding phosphorylation.

The activated STAT then dissociates from its receptor, forms a dimmer, enters into nucleus and binds to the enhanced GAS family, thus activating transcription, inducing cell transformation and regulating some gene expression related to cell proliferation and survival which play an important role in the tumorigenesis.

At present, receptor tyrosine kinases, such as VEGFR and EGFR are mostly investigated and angiogenesis inhibitors have been developed to be a systemic cancer treatment strategy. Early marketed protein kinase inhibitors are mainly single-target inhibitors against a single target. Although they have made remarkable achievements in cancer therapy previously, with the increase in the use of time and cases, there are increasingly defects. In contrast, multi-targeted kinase inhibitors are showing some advantages. By simultaneously targeting multiple targets and multiple kinase signaling pathways, multi-targeted kinase inhibitors can not only avoid drug resistance caused by a single target mutation but also significantly expand their anti-tumor spectrum. The failure of single-target inhibitors SU5416 and SU6668 indicates that multi-targeted kinase inhibitors will become the mainstream of kinase inhibitors development in the future. SU5416 and SU6668 target KDR and PDGFR-β respectively and were aborted because of poor efficacy in clinical phase III and II. However, the multi-target inhibitor sunitinib which targets multiple kinases like KDR etcs. is ultimately successful in market. Most of the currently studied compounds are multi-target inhibitors as they show better inhibitory activity and patient's tolerance compared to single-target inhibitors. The small molecule tyrosine inhibitors that are now marketed or in clinical trials can be mainly divided into the following categories according to the chemical structures: quinazolines, indolinones, pyridazines, cyanoquinolines, pyrrolopyrimidines and etc. Three anti-angiogenic TKIs including sunitinib, sorafenib and pazopanib with different binding capacity to angiogenic kinases are recently approved for the treatment of advanced cancer in patients (renal cell carcinoma, gastrointestinal stromal tumor and hepatocellular carcinoma). Many other anti-angiogenic TKIs are now under clinical trials from phase I to phase III. In addition to the beneficial anti-tumor activity, these drugs were also shown to have clinical tolerance and toxicity.

Long-term and high-dose use of taxanes injection has resulted in drug resistance in patients and led to decreased efficacy. Increasing evidences show that drug resistance may limit the efficacy of target receptor TKIs. Thus, it is of significant importance for the development of a new generation of anti-cancer drugs. At the same time, studies demonstrate that kinase-associated diseases are endogenously-related, making the single-target inhibitors difficult to exert their inhibitory activity.

Due to the essential roles of CDK and Auraro A and their related proteins in proliferating cells for coordination and promotion of cell cycle, their corresponding inhibitors can be used for the treatment of proliferative disorders, such as cancer (applications are generally targeting CDK or CDK specific therapy), as well as for the treatment of some other diseases, such as viral infections, autoimmune diseases, neurodegenerative diseases. When used in combination with the existing or new therapeutic agents, CDK-targeted therapy may also provide clinical benefits in the treatment of diseases previously described. In comparison to many existing anti-tumor agents and with respect to the afore-mentioned tyrosine kinases, CDK mutation and drug resistance of its inhibitors occur relatively less. Therefore, CDK targeted anticancer therapy could potentially have advantages over many current anti-tumor agents as they would not directly interact with DNA and should therefore reduce the risk of secondary tumor development.

Multi-target small molecule CDK inhibitors, such as flavopiridol and UCN201 have already shown good anti-tumor activity in clinical I and II trials. Nevertheless, most of the inhibitors are single-targeted and many companies have conducted research in this aspect. For example, a novel small-molecule CDK inhibitor AT7519 which is now under clinical I/II trials acts on multiple targets such as CDK1/cyclin B, CDK2/Cyclin A, CDK3/Cyclin E and etc. In the meantime, AT7519 can induce the activation of its family protein member GSK-3β by down-regulating its phosphorylation level, leading to cell apoptosis. Relatively, the structure types of cross-kinase protein family inhibitors at present are rarely reported, and thus the development of kinase inhibitors that can selectively act on multiple disease-specific targets will be of great significance.

SUMMARY

On the basis of the study of CDK2 and Aurora A small-molecule inhibitors, according to CDK2 and Aurora A crystal structures, we constructed structure-activity relationship (SAR) models and virtual screening models by computer-aided drug design tools. Moreover, we built a focused compound library by fragment-growing methods. Through virtual screening, we identified and synthesized a series of new compounds with the parent structure of 4-(five-membered heterocyclic pyrimidine/pyridine substituted)amino-H-3-pyrazolecarboxamide. Pharmacological tests showed that the compounds of the invention are not only good dual inhibitors of CDK2 and Aurora A but also exert inhibitory activity against various CMGC family and TK family kinases. They also showed potent inhibitory activity against multiple tumor cell lines and some of them are advantageous over known CDK2 inhibitor AT7519, Aurora A inhibitor AT-9283 and multi-target inhibitor staurosporine.

The invention relates to the compounds defined by formula (I):

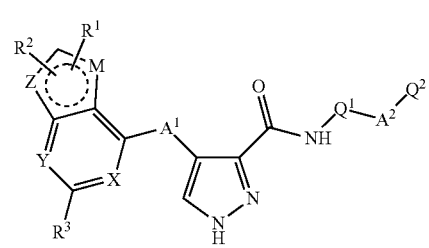

or pharmaceutically acceptable salts or tautomers thereof, wherein:

$R^1$, $R^2$ and $R^3$ each independently represent H, alkyl, cyano, halogen, haloalkyl, hydroxyl, thiol, alkoxyl, alkylthiol, alkoxylalkyl, aralkyl, diarylalkyl, aryl or Het;

X and Y each independently represent N atom or CH group, wherein the CH group can optionally be substituted by $R^4$, and $R^4$ may be H, alkyl, cyano, halogen, haloalkyl, hydroxyl, thiol, alkoxyl, alkylthiol, alkoxylalkyl, aralkyl, diarylalkyl, aryl or Het;

Z and M each independently represent NH, O, S or CH group with the proviso that one of Z and M is NH, O or S, wherein the CH or NH group can each optionally and independently be substituted by $R^5$, and $R^5$ may be H, alkyl, cyano, halogen, haloalkyl, hydroxyl, thiol, alkoxyl, alkylthiol, alkoxylalkyl, aralkyl, diarylalkyl, aryl or Het;

$A^1$ independently represents NH, O, S or alkylene group, wherein the NH or alkylene group can each optionally and independently be substituted by $R^6$, and $R^6$ may be H, alkyl, cyano, halogen, haloalkyl, hydroxyl, thiol, alkoxyl, alkylthiol, alkoxylalkyl, aralkyl, diarylalkyl, aryl or Het;

$A^2$ independently represents alkylene, C(O)NH, C(O), NHC(O), alkylene-C(O), C(O)-alkylene, alkylene-C(O)-alkylene or NHC(O)NH, wherein the above groups can each optionally and independently be substituted by $R^7$, and $R^7$ may be H, alkyl, cyano, halogen, haloalkyl, hydroxyl, thiol, alkoxyl, alkylthiol, alkoxylalkyl, aralkyl, diarylalkyl, aryl or Het;

$Q^1$ is selected from aryl or Het, wherein the aryl or Het can each optionally and independently be substituted by one or more $R^8$, and $R^8$ may be H, alkyl, cyano, halogen, haloalkyl, hydroxyl, thiol, alkoxyl, alkylthiol, alkoxylalkyl, aralkyl, diarylalkyl, aryl or Het;

$Q^2$ is selected from aryl or Het, wherein the aryl or Het can each optionally and independently be substituted by one or more $R^9$, and $R^9$ may be H, alkyl, cyano, halogen, haloalkyl, hydroxyl, thiol, alkoxyl, alkylthiol, alkoxylalkyl, aralkyl, diarylalkyl, aryl or Het;

the term "alkyl" refers to a linear or branched chain saturated hydrocarbon group having 1-6 carbon atoms, or a cyclic saturated hydrocarbon group having 3-6 carbon atoms, or a cyclic saturated hydrocarbon group having 3-6 carbon atoms which is attached to a linear or branched chain saturated hydrocarbon group having 1-6 carbon atoms;

the term "alkylene" refers to a linear or branched chain saturated hydrocarbon group having 1-6 carbon atoms, or a cyclic saturated hydrocarbon group having 3-6 carbon atoms, or a cyclic saturated hydrocarbon group having 3-6 carbon atoms which is attached to a linear or branched chain saturated hydrocarbon group having 1-6 carbon atoms; wherein one hydrogen atom is absent;

the term "alkoxyl" refers to a linear or branched chain saturated hydrocarbon group having 1-6 carbon atoms, or a cyclic saturated hydrocarbon group having 3-6 carbon atoms, or a cyclic saturated hydrocarbon group having 3-6 carbon atoms which is attached to a linear or branched chain saturated hydrocarbon group having 1-6 carbon atoms; wherein each carbon atom is optionally substituted by oxygen;

the term "alkylthiol" refers to a linear or branched chain saturated hydrocarbon group having 1-6 carbon atoms, or a cyclic saturated hydrocarbon group having 3-6 carbon atoms, or a cyclic saturated hydrocarbon group having 3-6 carbon atoms which is attached to a linear or branched chain saturated hydrocarbon group having 1-6 carbon atoms; wherein each carbon atom is optionally substituted by sulfur;

the term "alkoxylalkyl" refers to the alkyl group as defined above, which is attached to the alkoxyl group as defined above;

the term "aryl" refers to a carbonic ring selected from phenyl, naphthyl, acenaphthenyl or tetralyl, which may be each optionally substituted by 1, 2 or 3 substituents each independently selected from H, alkyl, cyano, halogen, haloalkyl, hydroxyl, thiol, alkoxyl, alkylthiol, alkoxylalkyl, aralkyl, diarylalkyl, aryl or Het;

the term "aralkyl" or "diarylalkyl" refers to the alkyl group as defined above, which is attached to the aryl group as defined above;

the term "Het" refers to a monocyclic heterocycle group selected from piperidyl, pyrrolyl, pyrazolyl, imidazolyl, furyl, thienyl, oxazolyl, isoxazolyl, thiazolyl, isothiazolyl, pyridyl, pyrimidinyl, pyrazinyl, or pyridazinyl, or a bicyclic heterocycle group selected from quinolyl, quinoxalinyl, indolyl, benzimidazolyl, benzoxazolyl, benzisoxazolyl, benzothiazolyl, benzisothiazolyl, benzofuryl, benzothienyl, 2,3-dihydro-1,4-benzodioxinyl or 1,3-benzodioxolyl; wherein the monocyclic or bicyclic heterocycle group is each optionally substituted by 1, 2 or 3 substituents each independently selected from halogen, haloalkyl, hydroxyl, alkyl or alkoxyl;

the term "halogen" refers to a substituent selected from fluoro (F), chloro (Cl), bromo (Br), or iodo (I);

the term "haloalkyl" refers to a linear or branched chain saturated hydrocarbon group having 1-6 carbon atoms, or a cyclic saturated hydrocarbon group having 3-6 carbon atoms, or a cyclic saturated hydrocarbon group having 3-6 carbon atoms which is attached to a linear or branched chain saturated hydrocarbon group having 1-6 carbon atoms; wherein one or more carbon atoms are substituted by one or more halogens.

In a preferable embodiment, $R^1$, $R^2$ and $R^3$ each independently represent H, alkyl, cyano, halogen, haloalkyl, hydroxyl, thiol, alkoxyl, alkylthiol, alkoxylalkyl, aralkyl or aryl;

X and Y each independently represent N atom or CH group, wherein the CH group can optionally be substituted by $R^4$, and $R^4$ may be H, alkyl, cyano, halogen, haloalkyl, hydroxyl, thiol, alkoxyl, alkylthiol, alkoxylalkyl, aralkyl or aryl;

Z and M each independently represent NH, O, S or CH group with the proviso that one of Z and M is NH, O or S, wherein the CH or NH group can each optionally and independently be substituted by $R^5$, and $R^5$ may be H, alkyl, cyano, halogen, haloalkyl, hydroxyl, thiol, alkoxyl, alkylthiol, alkoxylalkyl, aralkyl or aryl;

$A^1$ independently represents NH, O, S or alkylene group, wherein the NH or alkylene group can each optionally and independently be substituted by $R^6$, and $R^6$ may be H, alkyl, cyano, halogen, haloalkyl, hydroxyl, thiol, alkoxyl, alkylthiol, alkoxylalkyl, aralkyl or aryl;

$A^2$ independently represents alkylene, C(O)NH, C(O), NHC(O), alkylene-C(O), C(O)-alkylene, alkylene-C(O)-alkylene or NHC(O)NH, wherein the above groups can each optionally and independently be substituted by $R^7$, and $R^7$ may be H, alkyl, cyano, halogen, haloalkyl, hydroxyl, thiol, alkoxyl, alkylthiol, alkoxylalkyl, aralkyl or aryl;

$Q^1$ is selected from aryl or Het, wherein the aryl or Het can each optionally and independently be substituted by one or more $R^8$, and $R^8$ may be H, alkyl, cyano, halogen, haloalkyl, hydroxyl, thiol, alkoxyl, alkylthiol, alkoxylalkyl, aralkyl or aryl;

$Q^2$ is selected from aryl or Het, wherein the aryl or Het can each optionally and independently be substituted by one or more $R^9$, and $R^9$ may be H, alkyl, cyano, halogen, haloalkyl, hydroxyl, thiol, alkoxyl, alkylthiol, alkoxylalkyl, aralkyl or aryl.

In another preferable embodiment, $R^1$, $R^2$ and $R^3$ each independently represent H, alkyl, cyano, halogen, haloalkyl, hydroxyl, thiol, alkoxyl, alkylthiol or alkoxylalkyl;

X and Y each independently represent N atom or CH group, wherein the CH group can optionally be substituted by $R^4$, and $R^4$ may be H, alkyl, cyano, halogen, haloalkyl, hydroxyl, thiol, alkoxyl, alkylthiol or alkoxylalkyl;

Z and M each independently represent NH, O, S or CH group with the proviso that one of Z and M is NH, O or S, wherein the CH or NH group can each optionally and independently be substituted by $R^5$, and $R^5$ may be H, alkyl, cyano, halogen, haloalkyl, hydroxyl, thiol, alkoxyl, alkylthiol or alkoxylalkyl;

$A^1$ independently represents NH, O, S or alkylene group, wherein the NH or alkylene group can each optionally and independently be substituted by $R^6$, and $R^6$ may be H, alkyl, cyano, halogen, haloalkyl, hydroxyl, thiol, alkoxyl, alkylthiol or alkoxylalkyl;

$A^2$ independently represents alkylene, C(O)NH, C(O), NHC(O), alkylene-C(O), C(O)-alkylene, alkylene-C(O)-alkylene or NHC(O)NH, wherein the above groups can each optionally and independently be substituted by $R^7$, and $R^7$ may be H, alkyl, cyano, halogen, haloalkyl, hydroxyl, thiol, alkoxyl, alkylthiol or alkoxylalkyl;

$Q^1$ is selected from aryl or Het, wherein the aryl or Het can each optionally and independently be substituted by one or more $R^8$, and $R^8$ may be H, alkyl, cyano, halogen, haloalkyl, hydroxyl, thiol, alkoxyl, alkylthiol or alkoxylalkyl;

$Q^2$ is selected from aryl or Het, wherein the aryl or Het can each optionally and independently be substituted by one or more $R^9$, and $R^9$ may be H, alkyl, cyano, halogen, haloalkyl, hydroxyl, thiol, alkoxyl, alkylthiol or alkoxylalkyl.

In an other preferable embodiment, $R^1$, $R^2$ and $R^3$ each independently represent H, alkyl, cyano, halogen, haloalkyl, hydroxyl, thiol, alkoxyl, alkylthiol or alkoxylalkyl;

X and Y each independently represent N atom or CH group, wherein the CH group can optionally be substituted by $R^4$, and $R^4$ may be H, alkyl, cyano, halogen, haloalkyl, hydroxyl, thiol, alkoxyl, alkylthiol or alkoxylalkyl;

Z and M each independently represent NH, O, S or CH group with the proviso that one of Z and M is NH, O or S, wherein the CH or NH group can each optionally and independently be substituted by $R^5$, and $R^5$ may be H, alkyl, cyano, halogen, haloalkyl, hydroxyl, thiol, alkoxyl, alkylthiol or alkoxylalkyl;

$A^1$ independently represents NH, O, S or alkylene group, wherein the NH or alkylene group can each optionally and independently be substituted by $R^6$, and $R^6$ may be H, alkyl, cyano, halogen, haloalkyl, hydroxyl, thiol, alkoxyl, alkylthiol or alkoxylalkyl;

$A^2$ independently represents alkylene, C(O)NH, C(O), NHC(O), alkylene-C(O), C(O)-alkylene, alkylene-C(O)-alkylene or NHC(O)NH, wherein the above groups can each optionally and independently be substituted by $R^7$, and $R^7$ may be H, alkyl, cyano, halogen, haloalkyl, hydroxyl, thiol, alkoxyl, alkylthiol or alkoxylalkyl;

$Q^1$ is unsubstituted or substituted aromatic ring selected from phenyl, naphthyl, pyrrolyl, furyl, thienyl, pyridyl, pyrazinyl or pyrimidinyl, and the above groups can each optionally and independently be substituted by one or more $R^8$, and $R^8$ may be H, alkyl, cyano, halogen, haloalkyl, hydroxyl, thiol, alkoxyl, alkylthiol or alkoxylalkyl;

$Q^2$ is aromatic ring selected from phenyl, naphthyl, pyrazolyl, furyl, thienyl, pyridyl, pyrazinyl, pyrimidinyl; or $C_3$-$C_8$ aliphatic carbonic ring; or aliphatic heterocycle ring selected from tetrahydropyrrolyl, piperidyl, morpholinyl, methylpiperazinyl; and the above groups can each optionally and independently be substituted by one or more $R^8$, and $R^8$ may be H, alkyl, cyano, halogen, haloalkyl, hydroxyl, thiol, alkoxyl, alkylthiol or alkoxylalkyl.

In a further preferable embodiment, $R^1$, $R^2$ and $R^3$ each independently represent H, alkyl, cyano, halogen, haloalkyl, hydroxyl, thiol, alkoxyl, alkylthiol or alkoxylalkyl;

X and Y each independently represent N atom or CH group, wherein the CH group can optionally be substituted by $R^4$, and $R^4$ may be H, alkyl, cyano, halogen, haloalkyl, hydroxyl, thiol, alkoxyl, alkylthiol or alkoxylalkyl;

Z and M each independently represent NH, O, S or CH group with the proviso that one of Z and M is NH, O or S, wherein the CH or NH group can each optionally and independently be substituted by $R^5$, and $R^5$ may be H, alkyl, cyano, halogen, haloalkyl, hydroxyl, thiol, alkoxyl, alkylthiol or alkoxylalkyl;

$A^1$ independently represents NH, O, S or alkylene group, wherein the NH or alkylene group can each optionally and independently be substituted by $R^6$, and $R^6$ may be H, alkyl, cyano, halogen, haloalkyl, hydroxyl, thiol, alkoxyl, alkylthiol or alkoxylalkyl;

$A^2$ independently represents alkylene, C(O)NH, C(O), NHC(O), alkylene-C(O), C(O)-alkylene, alkylene-C(O)-alkylene or NHC(O)NH, wherein the above groups can each optionally and independently be substituted by $R^7$, and $R^7$ may be H, alkyl, cyano, halogen, haloalkyl, hydroxyl, thiol, alkoxyl, alkylthiol or alkoxylalkyl;

$Q^1$ is unsubstituted or substituted aromatic ring selected from phenyl, naphthyl, pyrrolyl, furyl, thienyl, pyridyl, pyrazinyl or pyrimidinyl and the substituent may be 1-2 halogen or trifluoromethyl;

$Q^2$ is aromatic ring selected from phenyl, naphthyl, pyrazolyl, furyl, thienyl, pyridyl, pyrazinyl, pyrimidinyl; or $C_3$-$C_8$ aliphatic carbonic ring; or aliphatic heterocycle ring selected from tetrahydropyrrolyl, piperidyl, morpholinyl, methylpiperazinyl.

In an other preferable embodiment, $R^1$, $R^2$ and $R^3$ each independently represents H or $C_{1-4}$ alkyl;

X and Y each independently represents N atom or CH group;

Z and M each independently represents NH, O, S or CH group with the proviso that one of Z and M is NH, O or S;

$A^1$ independently represents NH, O, S or $CH_2$ group;

$A^2$ independently represents chainlike $C_{1-4}$ alkylene, C(O)NH, C(O) or NHC(O);

$Q^1$ is unsubstituted or substituted aromatic ring selected from phenyl, naphthyl, pyrrolyl, furyl, thienyl, pyridyl, pyrazinyl or pyrimidinyl and the substituent may be 1-2 halogen or trifluoromethyl;

$Q^2$ is aromatic ring selected from phenyl, naphthyl, pyrazolyl, furyl, thienyl, pyridyl, pyrazinyl, pyrimidinyl; or $C_3$-$C_8$ aliphatic carbonic ring; or aliphatic heterocycle ring selected from tetrahydropyrrolyl, piperidyl, morpholinyl, methylpiperazinyl.

In a further preferable embodiment, $R^1$, $R^2$ and $R^3$ each independently represent H or methyl;

$A^1$ represents NH;

$A^2$ represents $CH_2$;

$Q^1$ represents phenyl;

$Q^2$ represents morpholinyl or methylpiperazinyl.

According to the invention, the pharmaceutically acceptable salts of the compounds of the invention include the acid addition salts formed by the compound of formula I with the following acids: hydrochloric acid, hydrobromic acid, sulfuric acid, phosphoric acid, methanesulfonic acid, benzenesulfonic acid, p-toluenesulfonic acid, naphthalenesulfonic acid, citric acid, tartaric acid, lactic acid, pyruvic acid, acetic acid, maleic acid or succinic acid, fumaric acid, salicylic acid, phenyl acetic acid, amygdalic acid. In addition, the acidic salts of inorganic base are included, for example, the salt containing alkaline metal cation, alkaline earth metal cation, or ammonium cation. When sulfur is present and when the nature of the adjacent atoms and groups are acceptable, it may exist in the form of —S—, —S(O)— or —S(O)$_2$—.

In the compounds of formula I, the following compounds are preferable:

4-(4-thieno[2,3-d]pyrimidinylamino)-N-(4-((4-methyl-1-piperazinyl)methyl)phenyl)-1H-3-pyrazole carboxamide (I-1)

4-(4-thieno[2,3-d]pyrimidinylamino)-N-(4-((4-morpholinyl)methyl)phenyl)-1H-3-pyrazolecarboxamide (I-2)

4-(4-(6-methylthieno[2,3-d]pyrimidinyl)amino)-N-(4-((4-methyl-1-piperazinyl)methyl)phenyl)-1H-3-pyrazolecarboxamide (I-3)

4-(4-(6-methylthieno[2,3-d]pyrimidinyl)amino)-N-(4-((4-morpholinyl)methyl)phenyl)-1H-3-pyrazolecarboxamide (I-4)

4-(4-(5-methylthieno[2,3-d]pyrimidinyl)amino)-N-(4-((4-methyl-1-piperazinyl)methyl)phenyl)-1H-3-pyrazolecarboxamide (I-5)

4-(4-(5-methylthieno[2,3-d]pyrimidinyl)amino)-N-(4-((4-morpholinyl)methyl)phenyl)-1H-3-pyrazolecarboxamide (I-6)

4-(4-(5,6-dimethylthieno[2,3-d]pyrimidinyl)amino)-N-(4-((4-methyl-1-piperazinyl)methyl)phenyl)-1H-3-pyrazolecarboxamide (I-7)

4-(4-(5,6-dimethylthieno[2,3-d]pyrimidinyl)amino)-N-(4-((4-morpholinyl)methyl)phenyl)-1H-3-pyrazolecarboxamide (I-8)

4-(4-thieno[3,2-d]pyrimidinylamino)-N-(4-((4-methyl-1-piperazinyl)methyl)phenyl)-1H-3-pyrazole carboxamide (I-9)

4-(4-thieno[3,2-d]pyrimidinylamino)-N-(4-((4-morpholinyl)methyl)phenyl)-1H-3-pyrazolecarboxamide (I-10)

4-(4-(7H-pyrrolo[2,3-d]pyrimidinyl)amino)-N-(4-((4-methyl-1-piperazinyl)methyl)phenyl)-1H-3-pyrazolecarboxamide (I-11)

4-(4-(7H-pyrrolo[2,3-d]pyrimidinyl)amino)-N-(4-((4-morpholinyl)methyl)phenyl)-1H-3-pyrazolecarboxamide (I-12)

4-(4-(6-methyl-7H-pyrrolo[2,3-d]pyrimidinyl)amino)-N-(4-((4-methyl-1-piperazinyl)methyl)phenyl)-1H-3-pyrazolecarboxamide (I-13)

4-(4-(6-methyl-7H-pyrrolo[2,3-d]pyrimidinyl)amino)-N-(4-((4-morpholinyl)methyl)phenyl)-1H-3-pyrazolecarboxamide (I-14)

4-(4-(5-methyl-7H-pyrrolo[2,3-d]pyrimidinyl)amino)-N-(4-((4-methyl-1-piperazinyl)methyl)phenyl)-1H-3-pyrazolecarboxamide (I-15)

4-(4-(5-methyl-7H-pyrrolo[2,3-d]pyrimidinyl)amino)-N-(4-((4-morpholinyl)methyl)phenyl)-1H-3-pyrazolecarboxamide (I-16)

4-(4-(5H-pyrrolo[3,2-d]pyrimidinyl)amino)-N-(4-((4-methyl-1-piperazinyl)methyl)phenyl)-1H-3-pyrazolecarboxamide (I-17)

4-(4-(5H-pyrrolo[3,2-d]pyrimidinyl)amino)-N-(4-((4-morpholinyl)methyl)phenyl)-1H-3-pyrazolecarboxamide (I-18)

4-(4-(6-methyl-5H-pyrrolo[3,2-d]pyrimidinyl)amino)-N-(4-((4-methyl-1-piperazinyl)methyl)phenyl)-1H-3-pyrazolecarboxamide (I-19)

4-(4-(6-methyl-5H-pyrrolo[3,2-d]pyrimidinyl)amino)-N-(4-((4-morpholinyl)methyl)phenyl)-1H-3-pyrazolecarboxamide (I-20)

4-(4-furo[2,3-d]pyrimidinylamino)-N-(4-((4-methyl-1-piperazinyl)methyl)phenyl)-1H-3-pyrazolecarboxamide (I-21)

4-(4-furo[2,3-d]pyrimidinylamino)-N-(4-((4-morpholinyl)methyl)phenyl)-1H-3-pyrazolecarboxamide (I-22)

4-(4-furo[3,2-d]pyrimidinylamino)-N-(4-((4-methyl-1-piperazinyl)methyl)phenyl)-1H-3-pyrazolecarboxamide (I-23)

4-(4-furo[3,2-d]pyrimidinylamino)-N-(4-((4-morpholinyl)methyl)phenyl)-1H-3-pyrazolecarboxamide (I-24)

4-(4-thieno[3,2-c]pyridylamino)-N-(4-((4-methyl-1-piperazinyl)methyl)phenyl)-1H-3-pyrazolecarboxamide (I-25)

4-(4-thieno[3,2-c]pyridylamino)-N-(4-((4-morpholinyl)methyl)phenyl)-1H-3-pyrazolecarboxamide (I-26)

4-(4-(2-methylthieno[3,2-c]pyridyl)amino)-N-(4-((4-methyl-1-piperazinyl)methyl)phenyl)-1H-3-pyrazolecarboxamide (I-27)

4-(4-(2-methylthieno[3,2-c]pyridyl)amino)-N-(4-((4-morpholinyl)methyl)phenyl)-1H-3-pyrazolecarboxamide (I-28)

4-(7-thieno[2,3-c]pyridylamino)-N-(4-((4-methyl-1-piperazinyl)methyl)phenyl)-1H-3-pyrazolecarboxamide (I-29)

4-(7-thieno[2,3-c]pyridylamino)-N-(4-((4-morpholinyl)methyl)phenyl)-1H-3-pyrazolecarboxamide (I-30)

4-(7-(3-methylthieno[2,3-c]pyridyl)amino)-N-(4-((4-methyl-1-piperazinyl)methyl)phenyl)-1H-3-pyrazolecarboxamide (I-31)

4-(7-(3-methylthieno[2,3-c]pyridyl)amino)-N-(4-((4-morpholinyl)methyl)phenyl)-1H-3-pyrazolecarboxamide (I-32)

4-(4-furo[3,2-c]pyridylamino)-N-(4-((4-methyl-1-piperazinyl)methyl)phenyl)-1H-3-pyrazolecarboxamide (I-33)

4-(4-furo[3,2-c]pyridylamino)-N-(4-((4-morpholinyl)methyl)phenyl)-1H-3-pyrazolecarboxamide (I-34)

4-(4-(2-methylfuro[3,2-c]pyridyl)amino)-N-(4-((4-methyl-1-piperazinyl)methyl)phenyl)-1H-3-pyrazolecarboxamide (I-35)

4-(4-(2-methylfuro[3,2-c]pyridyl)amino)-N-(4-((4-morpholinyl)methy)phenyl)-1H-3-pyrazolecarboxamide (I-36)

4-(7-furo[2,3-c]pyridylamino)-N-(4-((4-methyl-1-piperazinyl)methyl)phenyl)-1H-3-pyrazolecarboxamide (I-37)

4-(7-furo[2,3-c]pyridylamino)-N-(4-((4-morpholinyl)methyl)phenyl)-1H-3-pyrazolecarboxamide (I-38)

4-(7-furo[3,2-b]pyridylamino)-N-(4-((4-methyl-1-piperazinyl)methyl)phenyl)-1H-3-pyrazolecarboxamide (I-39)

4-(7-furo[3,2-b]pyridylamino)-N-(4-((4-morpholinyl)methyl)phenyl)-1H-3-pyrazolecarboxamide (I-40)

4-(4-furo[2,3-b]pyridylamino)-N-(4-((4-methyl-1-piperazinyl)methyl)phenyl)-1H-3-pyrazolecarboxamide (I-41)

4-(4-furo[2,3-b]pyridylamino)-N-(4-((4-morpholinyl)methyl)phenyl)-1H-3-pyrazolecarboxamide (I-42)

4-(7-(1H-pyrrolo[2,3-c]pyridyl)amino)-N-(4-((4-methyl-1-piperazinyl)methyl)phenyl)-1H-3-pyrazolecarboxamide (I-43)

4-(7-(1H-pyrrolo[2,3-c]pyridyl)amino)-N-(4-((4-morpholinyl)methyl)phenyl)-1H-3-pyrazolecarboxamide (I-44)

4-(7-(2-methyl-1H-pyrrolo[2,3-c]pyridyl)amino)-N-(4-((4-methyl-1-piperazinyl)methyl)phenyl)-1H-3-pyrazolecarboxamide (I-45)

4-(7-(2-methyl-1H-pyrrolo[2,3-c]pyridyl)amino)-N-(4-((4-morpholinyl)methyl)phenyl)-1H-3-pyrazolecarboxamide (I-46)

4-(4-(2-methylthieno[3,2-d]pyrimidine)ylamino)-N-(4-((4-methyl-1-piperazinyl)methyl)phenyl)-1H-3-pyrazolecarboxamide (I-47)

4-(4-(2-methylthieno[3,2-d]pyrimidine)ylamino)-N-(4-((4-morpholinyl)methyl)phenyl)-1H-3-pyrazolecarboxamide (I-48)

The compounds of the present invention can be prepared according to the following procedures:

Scheme 1

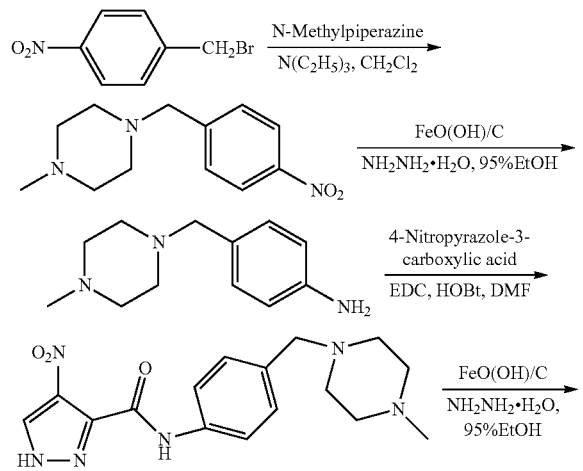

Scheme 2

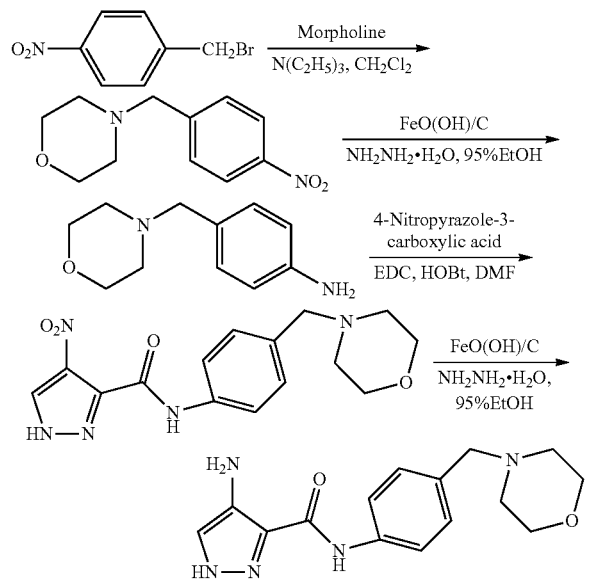

Scheme 3

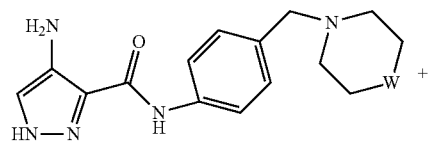

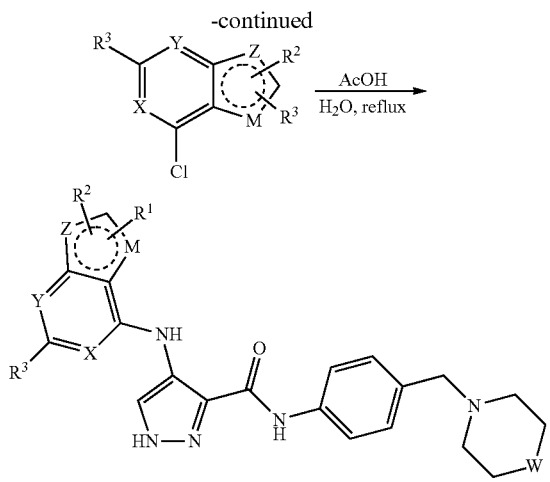

Scheme 4

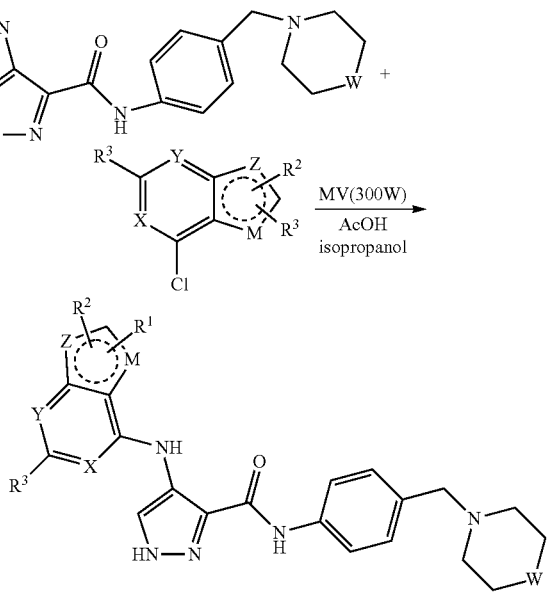

The compounds of the invention may be prepared with the above processes or similar processes, using the corresponding staffing materials according to the selections and positions of the substituents.

In the compounds of formula (I), the pyrazole ring can exist in two tautomeric forms A and B below.

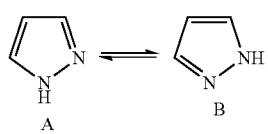

Other examples of tautomeric forms include, for example, keto-, enol-, and enolate-forms, for example, as the following tautomeric pairs: keto/enol (as illustrated below), imine/enamine, amide/imino alcohol, amidine/amidine, nitroso/oxime, thioketone/enethiol and nitro/aci-nitro.

The compounds of formula (I) and their subgroups an exist inhibitors of CMGC family kinases, in particular those selected from cyclin dependent kinases, glycogen synthase kinases (GSKs), mitogen-activated protein kinase (MAPK) and CDK-like kinase (CLK). The preferable compounds can inhibit one or more cyclin dependent kinases, glycogen synthase kinases (GSK) and mitogen-activated protein kinase (MAPK), and the kinase is selected from CDK1, CDK2, CDK3, CDK4, CDK5, CDK6, CDK7, CDK9, GSK3, CHK2, ERK7, FGFR, VEGFR, JAK, JNK, KDR, PDGFR, C-SCR, Aurora and FLT3.

The compounds of the invention can be used as inhibitors of TK family kinases, especially those selected from receptor tyrosine kinase family (especially epidermal growth factor receptor (EGFR), platelet-derived growth factor receptor (PDGFR), nerve growth factor receptor (NGFR), fibroblast growth factor receptors (FGFR), Hepatocyte growth factor (HGFR), Vascular Endothelial Growth Factor Receptor (VGFR) family) inhibitors and non-receptor tyrosine kinase family (including 10 families such as SRC, ABL, JAK, ACK, CSK, FAK, FES, FRK, TEC, SYK etc.) inhibitors. The compounds can modulate or inhibit the activities of CMGC family and TK family kinases, and thus are expected to be useful in providing a means for arresting or restoring cell proliferation, differentiation and related signal transduction abnormality. It is therefore anticipated that the compounds will be useful in treating or preventing proliferative disorders such as cancers. It is also envisaged that the compounds of the invention will be useful in treating conditions such as inflammation, viral infection, type II diabetes mellitus or non-insulin-dependent diabetes mellitus, auto-immune diseases, head trauma, stroke, epilepsy, neurological diseases (such as Alzheimer's disease), motor neuron disease.

The compounds of the invention can also be used as GSK3 inhibitor. As a consequence of their activity in modulating or inhibiting CDK kinases and glycogen synthase kinases, they are expected to be useful in providing a means of arresting or restoring the abnormal differentiation of the cell. It is therefore anticipated that the compounds will be useful in treating or preventing proliferative disorders such as cancers. It is also envisaged that the compounds of the invention will be useful in treating conditions such as viral infections, type IT diabetes mellitus or non-insulin dependent diabetes mellitus, autoimmune diseases, head trauma, stroke, epilepsy, neurodegenerative diseases (such as Alzheimer's disease), motor neuron disease, progressive supranuclear palsy, corticobasal degeneration and Pick's disease. One sub-group of disease states and conditions where it is envisaged that the compounds of the invention will be useful includes viral infections, autoimmune diseases and neurodegenerative diseases. Examples of cancers which may be inhibited include, but are not limited to, carcinoma, for example bladder cancer, breast cancer, colon cancer (e.g. colorectal cancer), lung cancer. GSK-3b can modulate the proliferation and apoptosis of cancer cell by regulating the protein factors like glycogen synthase, p27 or the like and participating classical intracellular signal pathways, play an important role in the pathogenesis of neuropsychic diseases by participating the modulation of monoamine neuroceptor, and mediate the occurrence of neurodegenerative diseases by other factors and pathways. Therefore, it is becoming a hot inhibitory target in the treatment of various diseases.

The invention encompasses the use of the compounds of the invention for inhibiting the activity of FLT3 kinase of a cell or a subject, or treating the conditions associated with the activity or expression of FLT3 kinase.

Examples of cancers, which may be inhibited include, but are not limited to, carcinoma, for example bladder cancer, breast cancer, colon cancer (e.g. colorectal cancer such as colon adenocarcinoma and colon adenoma), kidney cancer, epidermis cancer, liver cancer, lung cancer (e.g. adenocarcinoma, small cell lung cancer and non-small cell lung cancer), esophagus cancer, gallbladder cancer, ovarian cancer, pancreas cancer (e.g. exocrine pancreas cancer), stomach cancer, cervix cancer, thyroid cancer, prostate cancer, or skin cancer (for example squamous cell cancer); hematopoietic tumor of lymphoid lineage (for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma); hematopoietic tumor of myeloid lineage (for example acute or chronic myelogenous leukemia, myelodysplastic syndrome or promyelocytic leukemia); thyroid follicular cancer; tumor of mesenchymal origin (for example fibrosarcoma or rhabdomyosarcoma); tumor of the central or peripheral nervous system (for example astrocytoma, neuroblastoma, glioma or schwannoma); melanoma; seminoma; teratocarcinoma; osteosarcoma; xeroderma pigmentosum; keratoctanthoma; thyroid follicular cancer; Kaposi's sarcoma, B-cell lymphoma and chronic lymphocytic leukaemia.

Use of the compounds of the invention as the inhibitor for both CMGC and TK family kinases can be determined by the procedures in the following Examples and the activity levels of the compounds can be determined by IC50 values.

The pharmacological tests and results are summarized as follows.

(1) Assay of Inhibitory Activity to CDK2 of the Target Compound

The inhibitory activities of the synthesized compounds for CDK2/A is determined by fluorescence resonance energy transfer (FRET) and were compared with the positive control drug so as to screen the compounds with better activities. CDK2/A was purchased in the form of a kit or obtained through purification.

Procedures: CDK2/A is diluted to a suitable concentration with kinase diluent. The kinase reaction mixture contains CDK2/A, peptide substrate, HEPES (pH7.5), BRIJ-35, $MgCl_2$ and EDTA. CDK2 phospho-peptide substrate is used as the control of 100% phosphorylation and ATP-free as the control of 0% phosphorylation. After 1 h, the diluted Development Reagent A is added into the reaction system. Then the reaction is allowed to proceed for 1 h and then quenched with Stop Reagent. The excitation wavelength is 400 nm and the fluorescence intensity is detected at 445 nm (coumarin) and 520 nm (fluorescein). The inhibitions of the tested compounds are calculated according to the formula.

(2) Assay of Inhibitory Activity to Aurora A of the Target Compound

The inhibitory activities of the synthesized compounds for Aurora A is determined by fluorescence resonance energy transfer (FRET) and were compared with the positive control drug so as to screen the compounds with better activities. Aurora A was purchased in the form of a kit or obtained through purification.

Procedures: Aurora A is diluted to a suitable concentration with kinase diluent. The kinase reaction mixture contains Aurora A, peptide substrate, HEPES (pH7.5), BRIJ-35, $MgCl_2$ and EDTA. Aurora A phospho-peptide substrate is used as the control of 100% phosphorylation and ATP-free as the control of 0% phosphorylation. After 1 h, the diluted Development Reagent A is added into the reaction system. Then the reaction is allowed to proceed for 1 h and then quenched with Stop Reagent. The excitation wavelength is 400 nm and the fluorescence intensity is detected at 445 nm (coumarin) and 520 nm (fluorescein). The inhibitions of the tested compounds are calculated according to the formula.

(3) Results of CDK2, Aurora A Kinases Inhibition

| Compound No. | CDK2 inhibition % (1 × 10$^{-6}$ mol/L) | Aurora A inhibition % (1 × 10$^{-6}$ mol/L) |
| --- | --- | --- |
| I-1 | 70.91 | 67.88 |
| I-2 | 46.60 | 52.17 |
| I-3 | 62.47 | 75.19 |
| I-4 | 52.73 | 64.46 |
| I-5 | 51.24 | 58.62 |
| I-6 | 60.68 | 54.80 |
| I-7 | 65.12 | 54.93 |
| I-8 | 54.65 | 48.49 |
| I-9 | 65.03 | 67.63 |
| I-10 | 56.23 | 54.89 |
| I-11 | 67.90 | 64.26 |
| I-12 | 66.39 | 49.44 |
| I-13 | 67.00 | 60.82 |
| I-14 | 65.78 | 66.26 |
| I-15 | 73.16 | 57.43 |
| I-16 | 50.49 | 56.18 |
| I-17 | 65.96 | 62.17 |
| I-18 | 64.99 | 53.66 |
| I-19 | 65.01 | 70.28 |
| I-20 | 62.25 | 60.72 |
| I-21 | 66.01 | 60.80 |
| I-22 | 66.33 | 48.54 |
| I-23 | 60.65 | 59.67 |
| I-24 | 67.10 | 49.16 |
| I-25 | 59.48 | 59.70 |
| I-26 | 73.14 | 61.07 |
| I-27 | 72.62 | 67.82 |
| I-28 | 76.91 | 67.63 |
| I-29 | 76.17 | 64.39 |
| I-30 | 73.13 | 55.09 |
| I-31 | 45.34 | 70.27 |
| I-32 | 38.28 | 67.45 |
| I-33 | 44.93 | 45.08 |
| I-34 | 65.75 | 50.52 |
| I-35 | 73.23 | 55.99 |
| I-36 | 64.51 | 56.23 |
| I-37 | 72.22 | 59.65 |
| I-38 | 64.85 | 50.95 |
| I-39 | 37.58 | 42.11 |
| I-40 | 20.24 | 40.70 |
| I-41 | 56.16 | 42.64 |
| I-42 | 54.20 | 51.83 |
| I-43 | 76.09 | 55.02 |
| I-44 | 75.91 | 54.94 |
| I-45 | 60.11 | 63.21 |
| I-46 | 68.57 | 60.73 |
| AT-7519 | 74.96 | 38.02 |
| AT-9283 | 39.68 | 77.36 |

(4) Multi-Target Screening of the Tested Compounds

The experiment is based on the HotSpot platform for kinase screen provided by RCB through the method of standard radiolabelled kinase. The kinase (which is cloned into bacilliform virus expressing kinase domain and the IC50 value is determined, and FastBac bacilliform virus system is used as bacilliform virus), substrates and processes (Substrate+[33P]-ATP 33P-Substrate+ADP) are used to detect the interaction of test compound and the diseases associated with 342 kinases or related mutants. The system is the most comprehensive high-throughput screening system for the compounds affecting human kinases. In the experiment, 10 µM ATP, [33P]ATP and biotinylated peptides are used and SA-flash board is used to measure the incorporation rate of 33P. Various concentrations diluted with a series of DMSO stock solution were used. IC 50 values of the compounds are determined by regression analysis using data corresponding to different concentrations, or a single concentration is used to determine inhibition rate. The synthesized compounds are screened against 342 kinases at single dose of 10 µM in double holes according to the standard screening process. Staurosporine is used at the initial concentration of 10 µM, in 4-fold dilution for 10 doses as the positive control. Other positive controls are used at initial concentration of 20 µM, in 3-fold dilution for 10 doses. The tested 342 kinases are provided by Reaction Biology in Pennsylvania. DMSO was purchased from Sigma, USA.

The tested kinases: ABL1(1), ABL2/ARG(2), ACK1(3), AKT1(4), AKT2(5), AKT3(6), ALK(7), ALK1/ACVRL1 (8), ALK2/ACVR1(9), ALK3/BMPR1A(10), ALK4/ACVR1B(11), ALK5/TGFBR1(12), ALK6/BMPR1B(13), ARAF(14), ARK5/NUAK1(15), ASK1/MAP3K5(16), Aurora A(17), Aurora B(18), Aurora C(19), AXL(20), BLK (21), BMPR2(22), BMX/ETK(23), BRAF(24), BRK(25), BRSK1(26), BRSK2(27), BTK(28), c-Kit(29), c-MER(30), c-MET(31), c-Src(32), CAMK1a(33), CAMK1b(34), CAMK1d(35), CAMK1g(36), CAMK2a(37), CAMK2b (38), CAMK2d(39), CAMK2g(40), CAMK4(41), CAMKK1(42), CAMKK2(43), CDC7/DBF4(44), CDK1/cyclin A(45), CDK1/cyclin B(46), CDK1/cyclin E(47), CDK16/cyclin Y (PCTAIRE)(48), CDK2/cyclin A(49), CDK2/Cyclin A1(50), CDK2/cyclin E(51), CDK3/cyclin E(52), CDK4/cyclin D1(53), CDK4/cyclin D3(54), CDK5/p25(55), CDK5/p35(56), CDK6/cyclin D1(57), CDK6/cyclin D3(58), CDK7/cyclin H(59), CDK9/cyclin K(60), CDK9/cyclin T1(61), CHK1(62), CHK2(63), CK1a1(64), CK1d(65), CK1epsilon(66), CK1g1(67), CK1g2(68), CK1g3(69), CK2a(70), CK2a2(71), CLK1(72), CLK2(73), CLK3(74), CLK4(75), COT1/MAP3K8(76), CSK(77), CTK/MATK(78), DAPK1(79), DAPK2(80), DCAMKL1 (81), DCAMKL2(82), DDR1(83), DDR2(84), DLK/MAP3K12(85), DMPK(86), DMPK2(87), DRAK1/STK17A(88), DYRK1/DYRK1A(89), DYRK1B(90), DYRK2(91), DYRK3(92), DYRK4(93), EGFR(94), EPHA1(95), EPHA2(96), EPHA3(97), EPHA4(98), EPHA5(99), EPHA6(100), EPHA7(101), EPHA8(102), EPHB1(103), EPHB2(104), EPHB3(105), EPHB4(106), ERBB2/HER2(107), ERBB4/HER4(108), ERK1(109), ERK2/MAPK1(110), ERK5/MAPK7(111), ERK7/MAPK15(112), FAK/PTK2(113), FER(114), FES/FPS (115), FGFR1(116), FGFR2(117), FGFR3(118), FGFR4 (119), FGR(120), FLT1/VEGFR1(121), FLT3(122), FLT4/VEGFR3(123), FMS(124), FRK/PTK5(125), FYN(126), GCK/MAP4K2(127), GLK/MAP4K3(128), GRK1(129), GRK2(130), GRK3(131), GRK4(132), GRK5(133), GRK6 (134), GRK7(135), GSK3a(136), GSK3b(137), Haspin (138), HCK(139), HGK/MAP4K4(140), HIPK1(141), HIPK2(142), HIPK3(143), HIPK4(144), HPK1/MAP4K1 (145), IGF1R(146), IKKa/CHUK(147), IKKb/IKBKB (148), IKKe/IKBKE(149), IR(150), IRAK1(151), IRAK4 (152), IRR/INSRR(153), ITK(154), JAK1(155), JAK2 (156), JAK3(157), JNK1(158), JNK2(159), JNK3(160), KDR/VEGFR2(161), KHS/MAP4K5(162), LATS1(163), LATS2(164), LCK(165), LCK2/ICK(166), LIMK1(167), LIMK2(168), LKB1(169), LOK/STK10(170), LRRK2 (171), LYN(172), LYN B(173), MAPKAPK2(174), MAPKAPK3(175), MAPKAPK5/PRAK(176), MARK1(177), MARK2/PAR-1Ba(178), MARK3(179), MARK4(180), MEK1(181), MEK2(182), MEK3(183), MEKK1(184), MEKK2(185), MEKK3(186), MELK(187), MINK/MINK1 (188), MKK4(189), MKK6(190), MLCK/MYLK(191), MLCK2/MYLK2(192), MLK1/MAP3K9(193), MLK2/MAP3K10(194), MLK3/MAP3K11(195), MNK1(196), MNK2(197), MRCKa/CDC42BPA(198), MRCKb/CDC42BPB(199), MSK1/RPS6KA5(200), MSK2/

RPS6KA4(201), MSSK1/STK23(202), MST1/STK4(203), MST2/STK3(204), MST3/STK24(205), MST4(206), MUSK(207), MYLK3(208), MYO3b(209), NEK1(210), NEK11(211), NEK2(212), NEK3(213), NEK4(214), NEK5(215), NEK6(216), NEK7(217), NEK9(218), NLK(219), OSR1/OXSR1(220), P38a/MAPK14(221), P38b/MAPK11(222), P38d/MAPK13(223), P38g(224), p70S6K/RPS6KB1(225), p70S6Kb/RPS6KB2(226), PAK1(227), PAK2(228), PAK3(229), PAK4(230), PAK5(231), PAK6(232), PASK(233), PBK/TOPK(234), PDGFRa(235), PDGFRb(236), PDK1/PDPK1(237), PHKg1(238), PHKg2(239), PIM1(240), PIM2(241), PIM3(242), PKA(243), PKAcb(244), PKAcg(245), PKCa(246), PKCb1(247), PKCb2(248), PKCd(249), PKCepsilon(250), PKCeta(251), PKCg(252), PKCiota(253), PKCmu/PRKD1(254), PKCnu/PRKD3(255), PKCtheta(256), PKCzeta(257), PKD2/PRKD2(258), PKG1a(259), PKG1b(260), PKG2/PRKG2(261), PKN1/PRK1(262), PKN2/PRK2(263), PKN3/PRK3(264), PLK1(265), PLK2(266), PLK3(267), PLK4/SAK(268), PRKX(269), PYK2(270), RAF1(271), RET(272), RIPK2(273), RIPK3(274), RIPK5(275), ROCK1(276), ROCK2(277), RON/MST1R(278), ROS/ROS1(279), RSK1(280), RSK2(281), RSK3(282), RSK4(283), SGK1(284), SGK2(285), SGK3/SGKL(286), SIK1(287), SIK2(288), SIK3(289), SLK/STK2(290), SNARK/NUAK2(291), SRMS(292), SRPK1(293), SRPK2(294), SSTK/TSSK6(295), STK16(296), STK22D/TSSK1(297), STK25/YSK1 (298), STK32B/YANK2(299), STK32C/YANK3(300), STK33(301), STK38/NDR1(302), STK38L/NDR2(303), STK39/STLK3(304), SYK(305), TAK1(306), TAOK1(307), TAOK2/TAO1 (308), TAOK3/JIK(309), TBK1(310), TEC(311), TESK1(312), TGFBR2(313), TIE2/TEK(314), TLK1(315), TLK2(316), TNIK(317), TNK1(318), TRKA(319), TRKB(320), TRKC(321), TSSK2(322), TSSK3/STK22C(323), TTBK1(324), TTBK2(325), TXK(326), TYK1/LTK(327), TYK2(328), TYRO3/SKY(329), ULK1(330), ULK2(331), ULK3(332), VRK1(333), VRK2(334), WEE1(335), WNK1(336), WNK2(337), WNK3(338), YES/YES1(339), ZAK/mLTK(340), ZAP70(341), ZIPK/DAPK3(342).

The results of some compounds are set forth in FIG. 1: The compounds show over 90% inhibition activities to almost 200 kinases (the number of kinases are marked outside) and show selectivity to GMGC family: CDK family kinase CDK6/cyclin D1(57), CDK6/cyclin D3(58), CDK4/cyclin D1(53), CDK4/cyclin D3(54), CDK5/p35(56), GSK3b kinase(137), CDK5/p25(55), CDK16/cyclin Y PIM1 (48), DAPK2(98), ERK7/MAPK15(112); and TK family: KDR/VEGFR2(161), FLT1/VEGFR1(121), FLT4/VEGR3(123), FLT3(122). The inhibitory activities are more than 99%.

Compounds of the invention are tested for IC50 against GMGC family and TK family kinases. The initial concentration is 1 μM. The series dilution is prepared in 100% DMSO solution, 10 points for each compound at 3-fold. The reaction mixture contains 20 μM ATP, kinase and substrate biotinylated peptide. The hits are screened by quantitative, accurate, sensitive 33P labeled isotope label method for detection. % trl=[(tested compound signal−positive control signal)/(negative control signal−positive control signal)]%. Negative control=DMSO (100% Ctrl); Positive control=control compound (0% Ctrl). IC50 values are calculated using Hill equation and standard dose-response curve. Some results of IC50 calculated by Prism Graphpad 5 are listed in the table below.

| kinase | I-1 | I-3 | I-11 | I-13 | I-21 | I-27 | Staurosporine |
|---|---|---|---|---|---|---|---|
|  |  |  | IC50* (μM) |  |  |  |  |
| CDK1/cyclin A | 0.157 | 0.142 | 0.128 | 0.158 | 0.173 | 0.164 | 0.003 |
| CDK1/cyclin B | 0.087 | 0.079 | 0.071 | 0.088 | 0.096 | 0.091 | 0.003 |
| CDK1/cyclin E | 0.096 | 0.087 | 0.078 | 0.097 | 0.106 | 0.100 | 0.003 |
| CDK2/cyclin A | 0.015 | 0.014 | 0.013 | 0.015 | 0.017 | 0.016 | 0.001 |
| CDK2/Cyclin A1 | 0.009 | 0.009 | 0.008 | 0.010 | 0.011 | 0.010 | 0.001 |
| CDK3/cyclin E | 0.190 | 0.171 | 0.155 | 0.191 | 0.210 | 0.198 | 0.004 |
| CDK4/cyclin D1 | 0.006 | 0.006 | 0.006 | 0.008 | 0.007 | 0.007 | 0.009 |
| CDK5/p35 | 0.015 | 0.013 | 0.012 | 0.015 | 0.016 | 0.015 | 0.002 |
| CDK6/cyclin D1 | 0.005 | 0.004 | 0.004 | 0.005 | 0.005 | 0.005 | 0.003 |
| CDK7/cyclin H | 0.522 | 0.495 | 0.471 | 0.583 | 0.611 | 0.575 | 0.256 |
| CDK9/cyclin K | 0.039 | 0.037 | 0.035 | 0.043 | 0.045 | 0.043 | 0.018 |
| ERK7/MAPK15 | 0.007 | 0.007 | 0.007 | 0.008 | 0.008 | 0.008 | 0.006 |
| FGFR1 | 0.304 | 0.274 | 0.247 | 0.305 | 0.335 | 0.316 | 0.005 |
| FGFR2 | 0.233 | 0.210 | 0.189 | 0.234 | 0.257 | 0.242 | 0.003 |
| FGFR3 | 0.807 | 0.723 | 0.657 | 0.811 | 0.890 | 0.841 | 0.018 |
| FLT1/VEGFR1 | 0.020 | 0.019 | 0.019 | 0.023 | 0.024 | 0.022 | 0.015 |
| FLT3 | 0.000 | 0.000 | 0.001 | 0.001 | 0.001 | 0.001 | 0.001 |
| FLT4/VEGFR3 | 0.005 | 0.004 | 0.004 | 0.005 | 0.005 | 0.005 | 0.002 |
| GSK3b | 0.000 | 0.001 | 0.001 | 0.001 | 0.001 | 0.001 | 0.005 |
| JAK2 | 0.795 | 0.716 | 0.644 | 0.795 | 0.875 | 0.826 | 0.001 |
| JNK1 | 1.000 | 1.128 | 1.243 | 1.547 | 1.428 | 1.328 | 2.280 |
| JNK2 | 1.000 | 1.171 | 1.325 | 1.650 | 1.490 | 1.383 | 2.710 |
| KDR/VEGFR2 | 0.035 | 0.033 | 0.031 | 0.039 | 0.041 | 0.038 | 0.015 |

The results indicate that the synthesized compounds show activity and selectivity against tyrosine kinase receptor (RTK) family, such as FGFR1, FGFR2, KDR/VEGFR2, FLT1/VEGFR1, FLT3, FLT4/VEGFR3; and CGCM family, such as CDK kinase, GSK3b, JAK, ERK7/MAPK15 and the like, especially high activity and selectivity against kinase CDK, GSK3β and FLT3. The compounds show inhibitory activities against VEGFR and CDK at the same time, showing a great significance.

(4) Assay of Anti-Tumor Activity In Vitro of the Target Compound

The inhibitory activities against various cancer cell lines, such as breast cancer cell line MDA231, stomach cancer cell line MGC803, stomach cancer cell line BSG823, leukemia cell line K562, breast cancer cell line MCF-7, resistant breast cancer cell line MCF-7, leukemia cell line NB4, liver cancer cell line HEPG2, umbilical cord vein endothelium cell line HUVEC, lung cancer cell line A549, colon cancer cell line HCT116, large cell lung cancer cell line H460, liver cancer cell line 7721, lung cancer cell line H1229 and the like are determined with MTT method.

MTT method: the dehydrogenase associated with NADP in the mitochondria of living cell is capable of reducing exogenous MTT into insoluble bluish violet crystal (Formazan), which is precipitated in the cell. A dead cell does not have such a function. DMSO or Triple liquid (10% SDS-5% isobutanol-0.01 mol/L HCl) is used to dissolve the crystal in the cell. The OD determined at 570 nm by a microplate reader can reflect the amount of the living cell indirectly.

Procedures: the tumor cells in logarithmic growth phase are plated on 96 well plates and incubated for 24 h, to which is added the sample for screening (as for suspended cells, the sample can be added directly). The cells are further incubated in 5% $CO_2$ at 37☐ for 48 h and then MTT is added and the cells are incubated for a further 4 h. The crystal is dissolved with DMSO and the detection is performed on a microplate reader.

The anti-tumor activities of some target compounds in vitro against colon cancer cell HCT116, liver cancer cell 7721 and lung cancer cell H1229 are set forth below:

| Compound | HCT-116 ($IC_{50}/\mu M$) | 7721 ($IC_{50}/\mu M$) | H1299 ($IC_{50}/\mu M$) |
| --- | --- | --- | --- |
| I-1 | 0.13 | 6.232 | 3.30 |
| I-3 | 0.89 | 5.09 | 6.17 |
| I-16 | 32.27 | 54.19 | 88.97 |
| I-21 | 9.58 | 17.39 | 7.66 |
| I-22 | 8.63 | 18.09 | 10.31 |
| I-29 | 0.26 | 4.95 | 3.84 |
| I-39 | >200 | >200 | >200 |
| AT-7519 | 21.18 | >200 | 9.32 |
| AT-9283 | 21.25 | 61.18 | 10.76 |

The anti-tumor activities of target compound (I-1) against breast cancer cell line MDA231, stomach cancer cell line MGC803, stomach cancer cell line BSG823, leukemia cell line K562, breast cancer cell line MCF-7, resistant breast cancer cell line MCF-7, leukemia cell line NB4, liver cancer cell line HEPG2, umbilical cord vein endothelium cell line HUVEC, lung cancer cell line A549, colon cancer cell line HCT116, large cell lung cancer cell line H460 are set forth below.

| Cell line | I-1 ($IC_{50}/\mu M$) | AT-7519 ($IC_{50}/\mu M$) |
| --- | --- | --- |
| MDA231 | 5.45 | 2.58 |
| MGC803 | 2.27 | 1.93 |
| BSG823 | 20.73 | 16.72 |
| K562 | 3.20 | 3.24 |
| MCF7 | 0.42 | 2.04 |
| Resistant MCF7 | 3.73 | 22.10 |
| NB4 | 0.74 | 0.62 |
| HEPG2 | 25.24 | 53.58 |
| HUVEC | 2.54 | 5.67 |
| A549 | 50.26 | 53.52 |
| HCT116 | 0.25 | 2.63 |
| H460 | 2.72 | 5.63 |

The pharmacological test results demonstrate that the compounds of the invention have multi-kinases inhibitory activity and can be used in treatment or prevention of clinical diseases associated with kinase inhibitor, such as melanoma, liver cancer, kidney cancer, acute leukemia, non-small cell lung cancer, prostate cancer, thyroid cancer, skin cancer, colorectal cancer, pancreases cancer, ovarian cancer, breast cancer, myelodysplastic syndrome, esophageal cancer, gastrointestinal cancer or mesothelioma.

Pharmaceutical Formulations

The active compound can be administered alone or in the form of pharmaceutical composition (e.g. formulation). The composition comprises at least one active compound of the invention and one or more pharmaceutically acceptable carriers, adjuvants, excipients, diluents, fillers, stabilizers, preservatives. Accordingly, in a further aspect, the invention provides the synthesized compound and the sub-group thereof in the form of pharmaceutical composition, for example, the formula (I) as defined herein and the sub-group thereof. The pharmaceutical compositions can be in any form suitable for oral, parenteral, topical, intranasal, ophthalmic, otic, rectal, intravaginal or transdermal administration. Where the composition is intended for parenteral administration, it can be formulated for intravenous, intramuscular, intraperitoneal, subcutaneous administration or for direct delivery into a target organ or tissue by injection, infusion or other means of delivery.

Some pharmaceutical formulations are prepared as follows.

1) Lyophilized formulation: Aliquots of formulated compound of formula (I) and its sub group as hereinbefore defined are put into 50 mL vials and lyophilized. During lyophilisation, the composition is frozen using a one-step freezing protocol at −45☐. The temperature is raised to −10☐ for annealing, then lowered to −45☐ for freezing, followed by the first drying at 25☐ for approximately 3400 minutes, and then the second drying at 50☐. The pressure during the first and second drying is set at 80 millitor. 2) Tablet Formulation: A tablet composition (252 mg) containing the synthesized compound is prepared by mixing 50 mg of the compound with 197 mg of lactose (BP) as diluent and 3 mg of magnesium stearate as lubricant and compressing to form a tablet in a known manner. 3) Capsule Formulation: A capsule formulation is prepared by mixing 100 mg of the synthesized compound with 100 mg of lactose and filling the resulting mixture into standard opaque hard gelatin capsules. 4) Injectable Formulation I: A parenteral composition for administration by injection can be prepared by dissolving the synthesized compound (e.g. in a salt form) in water containing 10% propylene glycol to give a concentration of active compound of 1.5% by weight. The solution is filtered for sterility and the vial is then sealed. 5) Injectable Formulation II: A parenteral composition for injection is prepared by dissolving the synthesized compound (e.g. in salt form) (2 mg/ml) and mannitol (50 mg/ml) in water. The solution is filtered for sterility and filled into sealable 1 ml vials or ampoules. 6) Subcutaneous injection Formulation: A composition for subcutaneous administration is prepared by mixing the synthesized compound with pharmaceutical grade corn oil to give a concentration of 5 mg/ml. The composition is sterilized and filled into a suitable container.

In a further aspect, the invention provides the use of compound of the formula (I) and subgroups thereof as defined herein as antifungal agent. The compound may be used in animal medicine (for example, in the treatment of mammal such as human), or in the treatment of plant (e.g. in agriculture and horticulture), or as general antifungal agent, for example as preservative and disinfectant. In another aspect, the invention provides an antifungal composition for agricultural (including horticultural) use, comprising the compound of the formula (I) and the subgroup thereof as defined herein above and an agriculturally acceptable diluent or carrier.

For example, the antifungal activity of the synthesized compound is determined using the following protocol, comprising *Candida parpsilosis, Candida tropicalis, Candida albicans*-ATCC 36082 and *Cryptococcus neoformans*. The test microorganisms are maintained on Sabourahd Dextrose Agar slant at 4□. Singlet suspension of each microorganism is prepared by growing the yeast overnight at 27□ on a rotating drum in yeast-nitrogen base broth (YNB) with amino acids (Difco, Detroit, Mich.), (pH 7.0) and 0.05 morpholine propanesulphonic acid (MOPS). The suspension is then centrifuged and washed twice with 0.85% NaCl before sonicating the washed cell suspension for 4 seconds (Branson Sonifier, model 350, Danbury, Conn.). The singlet blastospore is counted in a haemocytometer and adjusted to the desired concentration in 0.85% NaCl. The activity of the test compound is determined using a modified broth microdilution technique. Test compound is diluted in DMSO to a 1.0 mg/ml ratio then diluted to 64 µg/ml in YNB broth (pH 7.0) with MOPS (fluconazol is used as the control) to provide a working solution of each compound. Using a 96-well plate, wells 1 and 3-12 are prepared with YNB broth, ten fold dilutions of the compound solution are made in wells 2-11 (concentration ranges are 64-0.125 µg/ml). Well 1431 serves as a sterility control and blank for the spectrophotometric assay. Well 12 serves as a growth control. The microtitre plate is inoculated with 10 µl in each of well 2-11 (final inoculum is 104 organisms/ml). Inoculated plate is incubated for 48 hours at 35□. The MIC values are determined spectrophotometrically by measuring the absorbance at 420 nm (Automatic Microplate Reader, DuPont Instruments, Wilmington, Del.) after agitation of the plates for 2 minutes with a vortex-mixer (Vorte-Genie 2 Mixer, Scientific Industries, Inc., Bolemia, N.Y.). The MIC endpoint is defined as the lowest drug concentration exhibiting approximately 50% (or more) reduction of the growth compared with the control well. With respect to the turbidity assay, this is defined as the lowest drug concentration at which turbidity in the well is <50% of the control (IC50). Minimal Cytolytic Concentration (MCC) is determined by subculturing all wells from the 96-well plate onto a Sabourahd Dextrose Agar (SDA) plate, incubating for 1-2 days at 35□, and then checking viability.

Some results are set forth as follows.

| Compound | Candida parpsilosis | Candida tropicalis | Candida albicans - ATCC 36082 MIC (µg/ML) | Cryptococcus neoformans |
|---|---|---|---|---|
| I-1 | 2.08 | 2.30 | 2.90 | 3.64 |
| I-3 | 2.11 | 1.88 | 5.08 | 4.89 |
| I-5 | 1.12 | 5.14 | 11.06 | 7.28 |
| I-7 | 9.81 | 10.29 | 14.71 | 17.75 |
| I-9 | 8.70 | 10.70 | 12.74 | 15.57 |
| I-11 | 11.20 | 7.72 | 7.45 | 15.03 |
| I-13 | 0.98 | 3.24 | 5.85 | 4.23 |
| I-15 | 5.78 | 5.00 | 6.77 | 9.40 |
| I-17 | 2.76 | 4.70 | 9.49 | 7.99 |
| I-19 | 6.45 | 8.58 | 11.80 | 12.86 |
| I-21 | 9.76 | 8.29 | 7.82 | 13.84 |
| I-23 | 4.32 | 3.24 | 2.92 | 5.82 |
| I-25 | 0.96 | 1.08 | 3.38 | 2.83 |
| I-27 | 1.02 | 3.57 | 5.48 | 4.06 |
| I-29 | 6.47 | 4.21 | 2.73 | 7.81 |

The invention also provides a method of treating a fungal infection in a plant or seed comprising treating the plant or seed with an antifungal effective amount of a fungicidal composition as defined above.

The compound is dissolved in acetone, with subsequent serial dilutions in acetone to obtain a range of desired concentrations. Final treatment volume is obtained by adding 9 volumes of 0.05% aqueous Tween-20™ solution or 0.01% TritonX-100™, depending upon the pathogen. The composition is then used to test the activity of the compound of the invention against tomato leaf blight (*Phytophthora infestans*) using the following protocol. Tomato (Rutgers variety) seeds are allowed to grow in a soil-free peat-based potting mixture until the seedlings are 10-20 cm tall. The plants are then sprayed to run-off with the test compound at a rate of 100 ppm. After 24 hours the test plants are inoculated by spraying with an aqueous sporangia suspension of *Phytophthora infestans*, and kept in a dew chamber overnight. The plants are then transferred to the greenhouse until disease develops on the untreated control plants.

Some results of the test compounds are set forth as follows.

| | Severity of tomato leaf blight [a] | | | |
|---|---|---|---|---|
| Compound | 0.0001 | 0.001 | 0.01 | 0.1 |
| I-1 | +++ | ++ | + | − |
| I-3 | ++ | ++ | − | − |
| I-5 | +++ | ++ | + | − |
| I-7 | ++ | ++ | − | − |
| I-9 | ++ | ++ | − | − |
| I-11 | +++ | ++ | + | − |
| I-13 | ++ | ++ | + | − |
| I-15 | ++ | ++ | + | − |
| I-17 | +++ | ++ | + | − |
| I-19 | ++++ | ++ | + | − |
| I-21 | ++++ | ++ | + | − |
| I-23 | +++ | ++ | − | − |
| I-25 | ++ | ++ | + | − |
| I-27 | ++++ | ++ | + | − |
| I-29 | +++ | ++ | + | − |
| Control | ++++ | ++++ | ++++ | +++ |

[a] ++++: >60% blight, +++: 40-60% blight, ++: 15-40% blight, +: 0-15% blight,, −: no blight

BRIEF DESCRIPTION OF THE DRAWINGS

FIG. 1 shows the inhibition rates of some compounds against 342 kinases, wherein the kinases are shown in serial number (see the above).

DETAILED DESCRIPTION OF THE INVENTION

The melting point is determined with type b melting point tube, wherein the medium is methylsilicone oil and the thermometer is not corrected. IR spectrum is determined with Nicolet Impact 410 infrared spectrometer, wherein compression is performed with KBr. $^1$HNMR is performed with JEOL FX90Q Fourier-Transform NMR Spectrometer, BRUKER ACF-300 NMR Spectrometer and BRUKER AM-500 NMR Spectrometer (internal standard TMS). MS is determined with Nicolet 2000 Fourier-Transform mass spectrometer and MAT-212 mass spectrometer. Microwave reaction is performed with CEM Discover single mode microwaver.

Example 1

4-methyl-1-(4-nitrobenzyl)piperazine (I-a)

p-nitrobenzyl bromide (10 g, 46.3 mmol) and dichloromethane (100 mL) were added into a 500 mL single neck flask, to which was slowly and dropwise added a mixture of N-methylpiperazine (4.7 g, 47.0 mmol) and triethylamine (7.1 g, 70.3 mmol) in dichloromethane (20 ml) under ice bath. The reaction mixture was refluxed for 1 h. The depletion of the starting materials was confirmed by TLC (ethyl acetate: petroleum ether=1:2). 150 mL chloroform and 100 mL saturated sodium bicarbonate solution were added into the reaction mixture, which was stirred vigorously at room temperature for 30 min. The reaction mixture was extracted with chloroform (100 ml×3). The organic layers were combined and washed with water and saturated sodium chloride once respectively (100 ml×1). Drying was performed with dry magnesium sulfate followed by filtration. After removal of the solvent under reduced pressure, 8.5 g yellowish solid was obtained; Yield: 78.1%. The product is used for subsequent reaction without further purification.

$^1$H-NMR [300 MHz, DMSO-d$_6$]: δ2.15 (3H, s, —CH$_3$), 2.3-2.5 (8H, m, —CH$_2$—×4), 3.5 (2H, s, —CH$_2$—), 7.5 (2H, d, J=8.7 Hz, ArH), 8.1 (2H, d, J=8.7 Hz, ArH).

Example 2

4-(4-nitrobenzyl)morpholine (I-b)

p-nitrobenzyl bromide (10 g, 46.5 mmol) and dichloromethane (100 mL) were added into a 500 mL single neck flask, to which was slowly and dropwise added a mixture of morpholine 4.1 g (47.1 mmol) and triethylamine (7.1 g, 70.3 mmol) in dichloromethane (20 ml) under ice bath. The reaction mixture was refluxed for 1 h. The depletion of the starting materials was confirmed by TLC (ethyl acetate: petroleum ether=1:2). 150 mL chloroform and 100 mL saturated sodium bicarbonate solution were added into the reaction mixture, which was stirred vigorously at room temperature for 30 min. The reaction mixture was extracted with chloroform (100 ml×3). The organic layers were combined and washed with water and saturated sodium chloride once respectively (100 ml×1). Drying was performed with dry magnesium sulfate followed by filtration. After removal of the solvent under reduced pressure, 8.7 g yellowish solid (I-b) was obtained; Yield: 84.5%. The product was used for subsequent reaction without further purification.

$^1$H-NMR [300 MHz, DMSO-d$_6$]: δ2.3 (4H, m, —NCH$_2$—×2), 3.3-3.5 (6H, m, —OCH$_2$—×2, —CH$_2$—), 6.9 (2H, d, J=8.7 Hz, ArH), 7.6 (2H, d, J=8.7 Hz, ArH).

Example 3

4-((4-methyl-1-piperazinyl)methyl)aniline (I-c)

Crude I-a (8.5 g, 36.2 mmol), FeO(OH)/C, 2.0 g as catalyst and 95% ethanol (100 ml) were added into a 500 mL single neck flask, which was refluxed. Into the reaction system were added slowly and dropwise a mixture of 25 mL hydrazine hydrate and 20 mL 95% ethanol. The depletion of the starting materials was confirmed by TLC (methanol: chloroform=1:15). Suction filtration was performed while the reaction mixture was hot. The filter cake was washed with hot ethanol twice (30 ml×2). After removal of the solvent under reduced pressure, white solid was obtained, which was dried under vacuum to give 6.7 g (I-c); Yield: 90.3%. The product was used for subsequent reaction without further purification.

$^1$H-NMR [300 MHz, DMSO-d$_6$]: δ2.1 (3H, s, —CH$_3$), 2.3-2.5 (8H, m, —CH$_2$—×4) 3.5 (2H, s, —CH$_2$—), 4.0 (2H, s, —NH$_2$), 7.5 (2H, d, J=8.7 Hz, ArH), 8.1 (2H, d, J=8.7 Hz, ArH).

Example 4

4-((4-morpholino)methyl)aniline (I-d)

Crude I-b (8.5 g, 38.3 mmol), FeO(OH)/C, 2.0 g as catalyst and 95% ethanol (100 ml) were added into a 500 mL single neck flask, which was refluxed. Into the reaction system were added slowly and dropwise a mixture of 25 mL hydrazine hydrate and 20 mL 95% ethanol. The depletion of the starting materials was confirmed by TLC (methanol: chloroform=1:20). Suction filtration was performed while the reaction mixture was hot. The filter cake was washed with hot ethanol twice (30 ml×2). After removal of the solvent under reduced pressure, white solid was obtained, which was dried under vacuum to give 6.6 g (I-d); Yield: 89.7%. The product was used for subsequent reaction without further purification.

$^1$H-NMR [300 MHz, DMSO-d$_6$]: δ2.3 (4H, m, —NCH$_2$—×2), 3.2 (4H, m, —OCH$_2$—×2), 3.5 (2H, s, —CH$_2$—), 4.9 (2H, s, —NH$_2$), 6.5 (2H, d, J=8.4 Hz, ArH), 6.9 (2H, d, J=8.4 Hz, ArH).

Example 5

N-(4-((4-methyl-1-piperazinyl)methyl)phenyl)-4-nitro-1H-3-pyrazolecarboxamide (I-e)

Crude I-c (7.5 g 36.6 mmol), 4-nitro-1H-pyrazole-3-carboxylic acid (6.3 g, 40.1 mmol), EDC-HCl (8.4 g, 44.0 mmol), HOBT (6.0 g, 44.4 mmol) and anhydrous DMF (100 ml) were added into a 250 mL round bottom flask, which was stirred for 24 hours at room temperature. The depletion of the starting materials was confirmed by TLC (methanol: chloroform=1:10). The reaction mixture was poured into 200 mL ice water and a large amount of yellowish solid precipitation was acquired, which was allowed to stand and suction filtered to give yellow solid. The crude was recrystallized from the mixed solvents of ethyl acetate and methanol to give 11.1 g (I-e); Yield: 88.2%; mp: 194-196° C.; MS [M+H]$^+$ 345.3.

$^1$H-NMR [300 MHz, DMSO-d$_6$]: δ2.2 (3H, s, —CH$_3$), 2.3-2.4 (8H, m, —CH$_2$—×4), 3.4 (2H, s, —CH$_2$—), 7.3 (2H, d, J=8.4 Hz, ArH), 7.6 (2H, d, J=8.4 Hz, ArH), 8.8 (1H, s, ArH), 10.6 (1H, s, —NHCO—), 14.2 (1H, s, —NH—, Pyrazole).

Example 6

N-(4-((4-morpholinyl)methyl)phenyl)-4-nitro-1H-3-pyrazolecarboxamide (I-f)

Crude I-d (7.5 g, 39.0 mmol), 4-nitro-1H-pyrazole-3-carboxylic acid (6.3 g, 40.1 mmol), EDC.HCl (8.4 g, 44.0 mmol), HOBT (6.0 g, 44.4 mmol) and anhydrous DMF (100 ml) were added into a 250 mL round bottom flask, which was stirred for 24 hours at room temperature. The depletion of the starting materials was confirmed by TLC (methanol: chloroform=1:20). The reaction mixture was poured into 200 mL ice water and a large amount of yellowish solid precipitation was acquired, which was allowed to stand and suction filtered to give yellow solid. The crude was recrystallized from the mixed solvents of ethyl acetate and methanol to give 11.6 g (I-f); Yield: 89.7%; mp: 208-210° C.; MS [M+H]$^+$ 332.4.

$^1$H-NMR [300 MHz, DMSO-d$_6$]: δ2.4 (4H, t, J=4.1 Hz, —NCH$_2$—×2), 3.4 (2H, s, —CH$_2$—), 3.6 (4H, t, J=4.1 Hz, —OCH$_2$—×2), 7.3 (2H, d, J=8.4 Hz, ArH), 7.6 (2H, d, J=8.4 Hz, ArH), 8.9 (1H, s, ArH), 10.7 (1H, s, —NHCO—), 14.2 (1H, s, Pyrazole).

Example 7

N-(4-((4-methyl-1-piperazinyl)methyl)phenyl-4-amino-1H-3-pyrazolecarboxamide (I-g)

Crude I-e (6.0 g, 17.4 mmol), FeO(OH)/C, 2 g as catalyst and 95% ethanol (100 ml) were added into a 250 mL single neck flask, which was refluxed. Into the reaction system were added slowly and dropwise a mixture of 25 mL hydrazine hydrate and 20 mL 95% ethanol. The depletion of the starting materials was confirmed by TLC (methanol: chloroform=1:10). Suction filtration was performed while the reaction mixture was hot. The filter cake was washed with hot ethanol twice (30 ml×2). After removal of the solvent under reduced pressure, off-white solid was obtained. The crude was recrystallized from the mixed solvents of ethyl acetate and methanol to give 3.5 g (I-g); Yield: 63.9%. mp: 199-201° C., MS [M+H]$^+$ 315.8.

$^1$H-NMR [300 MHz, DMSO-d$_6$]: δ2.1 (3H, s, —CH$_3$), 2.3-2.5 (81H, m, —CH$_2$—×4), 3.3 (2H, s, —CH$_2$—), 4.7 (2H, s, —NH$_2$), 7.1-7.2 (3H, m, ArH), 7.7 (2H, d, ArH), 9.7 (1H, s, —NHCO—), 12.7 (1H, s, Pyrazole).

Example 8

N-(4-((4-morpholinyl)methyl)phenyl)-4-amino-1H-3-pyrazolecarboxamide (I-h)

Crude I-f (6.0 g, 18.1 mmol), FeO(OH)/C, 2 g as catalyst and 95% ethanol (100 ml) were added into a 250 mL single neck flask, which was refluxed. Into the reaction system were added slowly and dropwise a mixture of 25 mL hydrazine hydrate and 20 mL 95% ethanol. The depletion of the starting materials was confirmed by TLC (methanol: chloroform=1:10). Suction filtration was performed while the reaction mixture was hot. The filter cake was washed with hot ethanol twice (30 ml×2). After removal of the solvent under reduced pressure, off-white solid was obtained. The crude was recrystallized from the mixed solvents of ethyl acetate and methanol to give 3.2 g (I-h); Yield: 58.6%. mp: 216-218° C., MS [M+H]$^+$ 302.0.

$^1$H-NMR [300 MHz, DMSO-d$_6$]: δ2.5 (4H, m, —NCH$_2$—×2), 3.3 (2H, s, —CH$_2$—), 3.6 (4H, m, —OCH$_2$—×2), 4.7 (2H, s, —NH$_2$), 7.2 (3H, m, ArH), 7.7 (2H, d, J 8.4 Hz, ArH), 9.7 (1H, s, —NHCO—), 12.7 (1H, s, Pyrazole)

Example 9

4-(4-thieno[2,3-d]pyrimidinylamino)-N-(4-((4-methyl-1-piperazinyl)methyl)phenyl)-1H-3-pyrazole carboxamide (I-1)

129 mg (0.41 mmol) of N-(4-((4-methyl-1-piperazinyl)methyl)phenyl-4-amino-1H-3-pyrazolecarboxamide, 70 mg (0.41 mmol) of 4-chlorothieno[2,3-d]pyrimidine and 25 mL of 50% aqueous acetic acid were added into a 50 mL single neck flask, which was refluxed. The depletion of the starting materials was confirmed by TLC (methanol:chloroform=1: 10). The reaction mixture was cooled to room temperature and adjusted with saturated aqueous NaOH solution to pH 8-9, and was extracted with ethyl acetate for three times (50 ml×3). The extracts were combined, dried with dry magnesium sulfate. After suction filtration and removal of the solvent under reduced pressure, yellowish solid was obtained. The crude was subjected to column chromatography (mobile phase: methanol:chloroform=1:15) to give 70 mg (I-1). Yield: 37.8%; mp: 285-287° C.; [M+H]$^+$ 449.3.

$^1$H-NMR [300 MHz, DMSO-d$_6$]: δ2.1 (3H, s, —CH$_3$), 2.2-2.4 (8H, m, —CH$_2$—×4), 3.4 (2H, s, —CH$_2$—), 7.3 (2H, d, J=8.4 Hz, ArH), 7.5 (1H, d, J=5.4 Hz, ArH), 7.7-7.8 (3H, m, ArH), 8.5 (1H, s, ArH), 8.6 (1H, 8, ArH), 10.0 (1H, s, —NHCO—), 10.3 (1H, s, —NH—), 13.5 (1H, s, Pyrazole).

Example 10

4-(4-thieno[2,3-d]pyrimidinylamino)-N-(4-((4-morpholinyl)methyl)phenyl)-1H-3-pyrazolecarboxamide (I-2)

Compound I-2 (78 mg) was prepared in similar manner as I-1, using 124 mg (0.41 mmol) of N-(4-((4-morpholinyl) methyl)phenyl)-4-amino-1H-3-pyrazolecarboxamide and 70 mg (0.41 mmol) of 4-chlorothieno[2,3-d]pyrimidine as starting materials. Yield: 43.6%; mp: 262-265° C.; MS [M+H]$^+$ 436.2.

$^1$H-NMR [300 MHz, DMSO-d$_6$]: δ2.3 (4H, t, J=4.2 Hz, —CH$_2$—×2), 3.4 (2H, s, —CH$_2$—), 3.5 (4H, t, J=4.2 Hz, —CH$_2$—×2), 7.3 (2H, d, J=8.4, ArH), 7.5 (1H, d, J=6.0 Hz, ArH), 7.7-7.8 (3H, m, ArH), 8.5 (1H, s, ArH), 8.6 (1H, s, ArH), 9.9 (1H, s, —NHCO—), 10.3 (1H, s, —NH—), 13.5 (1H, s, Pyrazole).

Example 11

4-(4-(6-methylthieno[2,3-d]pyrimidinyl)amino)-N-(4-((4-methyl-1-piperazinyl)methyl)phenyl)-1H-3-pyrazolecarboxamide (I-3)

Compound I-3 (75 mg) was prepared in a similar manner as I-1, using 120 mg (0.38 mmol) of N-(4-((4-methyl-1-piperazinyl)methyl)phenyl-4-amino-1H-3-pyrazolecarboxamide and 120 mg (0.38 mmol) of 4-chloro-6-methylthieno [2,3-d]pyrimidine as starting materials. Yield: 42.9%; mp: 235-238° C., MS [M+H]$^+$ 463.3.

$^1$H-NMR [300 MHz, DMSO-d$_6$]: δ2.1 (3H, s, —CH$_3$), 2.2-2.4 (8H, m, —CH—×4), 2.6 (31, s, —CH$_3$), 3.4 (2H, s, —CH$_2$—), 7.2 (1H, s, ArH), 7.3 (2H, d, J=8.4 Hz, ArH), 7.8 (2H, d, J=8.4 Hz, ArH), 8.5 (2H, s, ArH), 9.8 (1H, s, —NHCO—), 10.3 (1H, s, —NH—), 13.5 (1H, s, Pyrazole).

Example 12

4-(4-(6-methylthieno[2,3-d]pyrimidinyl)amino)-N-(4-((4-morpholinyl)methyl)phenyl)-1H-3-pyrazole-carboxamide (I-4)

Compound I-4 (80 mg) was prepared in a similar manner as I-1, using 118 mg (0.38 mmol) of N-(4-((4-morpholinyl) methyl)phenyl)-4-amino-1H-3-pyrazolecarboxamide and 70 mg (0.38 mmol) of 4-chloro-6-methylthieno[2,3-d]pyrimidine as starting materials. Yield: 47.0%; mp: >280° C., MS [M+H]$^+$ 450.3.

$^1$H-NMR [300 MHz, DMSO-d$_6$]: δ2.4 (4H, t, J=4.2 Hz, —CH$_2$—×2), 2.6 (3H, s, —CH$_3$), 3.4 (2H, s, —CH$_2$—), 3.6

(4H, t, J=4.2 Hz, —CH₂—×2), 7.2 (1H, s, ArH), 7.3 (2H, d, J=8.4 Hz, ArH), 7.8 (2H, d, J=8.4 Hz, ArH), 8.5 (2H, s, ArH), 9.8 (1H, s, —NHCO—), 10.3 (1H, s, —NH—), 13.5 (1H, s, Pyrazole).

Example 13

4-(4-(5-methylthieno[2,3-d]pyrimidinyl)amino)-N-(4-((4-methyl-1-piperazinyl)methyl)phenyl)-1H-3-pyrazolecarboxamide (I-5)

Compound I-5 (72 mg) was prepared in a similar manner as I-1, using 120 mg (0.38 mmol) of N-(4-((4-methyl-1-piperazinyl)methyl)phenyl-4-amino-1H-3-pyrazolecarboxamide and 70 mg (0.38 mmol) of 4-chloro-5-methylthieno[2,3-d]pyrimidine as starting materials. Yield: 41.1%; mp: 245-247° C., MS [M+H]⁺ 463.3.

¹H-NMR [300 MHz, DMSO-d₆]: δ2.1 (3H, s, —CH₃), 2.2-2.4 (8H, m, —CH₂—×4), 2.8 (3H, s, —CH₃), 3.4 (2H, s, —CH₂—), 7.3 (2H, d, J=8.4 Hz, ArH), 7.4 (1H, s, ArH), 7.8 (2H, d, J=8.4 Hz, ArH), 8.6 (1H, s, ArH), 8.7 (1H, s, ArH), 10.2 (1H, s, —NHCO—), 10.3 (1H, s, —NH—), 13.5 (1H, s, Pyrazole).

Example 14

4-(4-(5-methylthieno[2,3-d]pyrimidinyl)amino)-N-(4-((4-morpholinyl)methyl)phenyl)-1H-3-pyrazolecarboxamide (I-6)

Compound I-6 (64 mg) was prepared in a similar manner as I-1, using 118 mg (0.38 mmol) of N-(4-((4-morpholinyl)methyl)phenyl)-4-amino-1H-3-pyrazolecarboxamide and 70 mg (0.38 mmol) of 4-chloro-5-methylthieno[2,3-d]pyrimidine as starting materials. Yield: 37.6%; mp: >280° C., MS [M+H]⁺ 450.3.

¹H-NMR [300 MHz, DMSO-d₆]: δ2.4 (4H, t, J=4.2 Hz, —CH₂—×2), 2.8 (3H, s, —CH₃), 3.4 (2H, s, —CH₂—), 3.6 (4H, t, J=4.2 Hz, —CH₂—×2), 7.3 (2H, d, J=8.4 Hz, ArH), 7.4 (1H, s, ArH), 7.8 (2H, d, J=8.4 Hz, ArH), 8.6 (1H, s, ArH), 8.7 (1H, s, ArH), 10.2 (1H, s, —NHCO—), 10.3 (1H, s, —NH—), 13.5 (1H, s, Pyrazole).

Example 15

4-(4-(5,6-dimethylthieno[2,3-d]pyrimidinyl)amino)-N-(4-((4-methyl-1-piperazinyl)methyl)phenyl)-1H-3-pyrazolecarboxamide (I-7)

Compound I-7 (66 mg) was prepared in a similar manner as I-1, using 111 mg (0.35 mmol) of N-(4-((4-methyl-1-piperazinyl)methyl)phenyl-4-amino-1H-3-pyrazolecarboxamide and 70 mg (0.35 mmol) of 4-chloro-5,6-dimethylthieno[2,3-d]pyrimidine as starting materials. Yield: 39.3%; mp: 264-267° C.; MS [M+H]⁺ 477.3.

¹H-NMR [300 MHz, DMSO-d₆]: δ2.1 (3H, s, —CH₃), 2.2-2.4 (8H, m, —CH₂—×4), 2.6 (3H, s, —CH₃), 2.8 (3-H, s, —CH₃), 3.4 (2H, s, —CH₂—), 7.3 (2H, d, J=8.4 Hz, ArH), 7.8 (2H, d, J=8.4 Hz, ArH), 8.6 (1H, s, ArH), 8.7 (1H, s, ArH), 10.2 (1H, s, —NHCO—), 10.3 (1H, s, —NH—), 13.5 (1H, s, Pyrazole)

Example 16

4-(4-(5,6-dimethylthieno[2,3-d]pyrimidinyl)amino)-N-(4-((4-morpholinyl)methyl)phenyl)-1H-3-pyrazolecarboxamide (I-8)

Compound I-8 (73 mg) was prepared in a similar manner as I-1, using 110 mg (0.35 mmol) of N-(4-((4-morpholinyl)methyl)phenyl)-4-amino-1H-3-pyrazolecarboxamide and 70 mg (0.35 mmol) of 4-chloro-5,6-dimethylthieno[2,3-d]pyrimidine as starting materials. Yield: 44.5%; mp: 254-256° C., MS [M+H]⁺ 464.3.

¹H-NMR [300 MHz, DMSO-d₆]: δ2.4 (4H, t, J=4.2 Hz, —CH₂—×2), 2.6 (3H, s, —CH₃), 2.8 (3H, s, —CH₃), 3.4 (2H, s, —CH₂—), 3.6 (4H, t, J=4.2 Hz, —CH₂—×2), 7.3 (2H, d, J=8.4 Hz, ArH), 7.8 (2H, d, J=8.4 Hz, ArH), 8.6 (1H, s, ArH), 8.7 (1H, s, ArH), 10.2 (1H, s, —NHCO—), 10.3 (1H, s, —NH—), 13.5 (1H, s, Pyrazole).

Example 17

4-(4-thieno[3,2-d]pyrimidinylamino)-N-(4-((4-methyl-1-piperazinyl)methyl)phenyl)-1H-3-pyrazole carboxamide (I-9)

Compound I-9 (88 mg) was prepared in a similar manner as I-1, using 129 mg (0.41 mmol) of N-(4-((4-methyl-1-piperazinyl)methyl)phenyl-4-amino-1H-3-pyrazolecarboxamide and 70 mg (0.41 mmol) of 4-chlorothieno[3,2-d]pyrimidine as starting materials. Yield: 47.8%; mp: >280° C., MS [M+H]⁺ 449.3.

¹H-NMR [300 MHz, DMSO-d₆]: δ2.2 (3H, s, —CH₃), 62.3-2.5 (8H, m, —CH₂—×4), 3.4 (2H, s, —CH₂—), 7.3 (2H, d, J=8.4 Hz, ArH), 7.5 (1H, d, J=5.3 Hz, ArH), 7.8 (2H, d, J=8.4 Hz, ArH), 8.2 (1H, d, J=5.3 Hz, ArH), 8.5 (1H, s, ArH), 8.7 (1H, s, ArH), 9.7 (1H, s, —NHCO—), 10.3 (1H, s, —NH—), 13.5 (1H, s, Pyrazole).

Example 18

4-(4-thieno[3,2-d]pyrimidinylamino)-N-(4-((4-morpholinyl)methyl)phenyl)-1H-3-pyrazolecarboxamide (I-10)

Compound I-10 (93 mg) was prepared in a similar manner as I-1, using 128 mg (0.41 mmol) of N-(4-((4-morpholinyl)methyl)phenyl)-4-amino-1H-3-pyrazolecarboxamide and 70 mg (0.41 mmol) of 4-chlorothieno[3,2-d]pyrimidine as starting materials. Yield: 52.0%; mp: 275-277° C.; MS [M+H]⁺ 436.3.

¹H-NMR [300 MHz, DMSO-d₆]: δ2.4 (4H, t, J=4.2 Hz, —CH₂—×2), 3.4 (2H, s, —CH₂—), 3.6 (4H, t, J=4.2 Hz, —CH₂—×2), 7.3 (2H, d, J=8.4 Hz, ArH), 7.5 (1H, d, J=5.2 Hz, ArH), 7.8 (2H, d, J=8.4 Hz, ArH), 8.3 (1H, d, J=5.2 Hz, ArH), 8.5 (1H, s, ArH), 8.7 (1H, s, ArH), 9.7 (1H, s, —NHCO—), 10.3 (18, s, —NH—), 13.5 (1H, s, Pyrazole).

Example 19

4-(4-(7H-pyrrolo[2,3-d]pyrimidinyl)amino)-N-(4-((4-methyl-1-piperazinyl)methyl)phenyl)-1H-3-pyrazolecarboxamide (I-11)

Compound I-11 (63 mg) was prepared in a similar manner as I-1, using 144 mg (0.46 mmol) of N-(4-((4-methyl-1-piperazinyl)methyl)phenyl-4-amino-1H-3-pyrazolecarboxamide and 70 mg (0.46 mmol) of 4-chloro-7H-pyrrolo[2,3-d]pyrimidine as starting materials. Yield: 32.0%; mp: 229-230° C., MS [M+H]⁺ 432.3.

¹H-NMR [300 MHz, DMSO-d₆]: δ2.1 (3H, s, —CH₃), 2.2-2.4 (8H, m, —CH₂—×4), 3.4 (2H, s, —CH₂—), 6.5 (1H, s, ArH), 7.3 (2H, d, J=8.4 Hz, ArH), 7.6 (1H, s, ArH), 7.8 (2H, d, J=8.4 Hz, ArH), 8.4 (1H, s, ArH), 8.6 (1H, s, ArH), 9.2 (1H, s, —NHCO—), 10.2 (1H, s, —NH—), 12.0 (1H, s, Pyrrole), 13.4 (1H, s, Pyrazole).

Example 20

4-(4-(7H-pyrrolo[2,3-d]pyrimidinyl)amino)-N-(4-((4-morpholinyl)methyl)phenyl)-1H-3-pyrazolecarboxamide (I-12)

Compound I-12 (70 mg) was prepared in a similar manner as I-1, using 142 mg (0.46 mmol) of N-(4-((4-morpholinyl)methyl)phenyl)-4-amino-1H-3-pyrazolecarboxamide and 70 mg (0.46 mmol) of 4-chloro-7H-pyrrolo[2,3-d]pyrimidine as starting materials. Yield: 36.6%; mp: 213-214° C., MS [M+H]$^+$ 419.3.

$^1$H-NMR [300 MHz, DMSO-d$_6$]: δ2.3 (4H, t, J=4.4 Hz, —CH$_2$—×2), 2.4 (2H, s, —CH$_2$—), 3.6 (4H, t, J=4.4 Hz, —CH$_2$—×2), 6.5 (1H, s, ArH), 7.3 (2H, d, J=8.4 Hz, ArH), 7.6 (1H, s, ArH), 7.8 (2H, d, J=8.4 Hz, ArH), 8.4 (1H, s, ArH), 8.6 (1H, s, ArH), 9.2 (1H, s, —NHCO—), 10.2 (1H, s, —NH—), 12.0 (1H, s, Pyrrole), 13.4 (1H, P, Pyrazole).

Example 21

4-(4-(6-methyl-7H-pyrrolo[2,3-d]pyrimidinyl)amino)-N-(4-((4-methyl-1-piperazinyl)methyl)phenyl)-1H-3-pyrazolecarboxamide (I-13)

Compound I-13 (56 mg) was prepared in a similar manner as I-1, using 132 mg (0.42 mmol) of N-(4-((4-methyl-1-piperazinyl)methyl)phenyl-4-amino-1H-3-pyrazolecarboxamide and 70 mg (0.42 mmol) of 4-chloro-6-methyl-7H-pyrrolo[2,3-d]pyrimidine as starting materials. Yield: 23.0%; mp: 268-270° C., MS [M+H]$^+$ 446.3.

$^1$H-NMR [300 MHz, DMSO-d$_6$]: δ2.1 (3H, s, —CH$_3$), 2.2-2.4 (1H, m, —CH$_2$—×4. —CH$_3$), 3.4 (2H, s, —CH$_2$—), 6.5 (1H, s, ArH), 7.3 (2H, d, J=8.4 Hz, ArH), 7.8 (2I, d, J=8.4 Hz, ArH), 8.4 (1H, s, ArH), 8.6 (1H, s, ArH), 9.2 (1H, s, —NHCO—), 10.2 (1H, s, —NH—), 12.0 (1H, s, Pyrrole), 13.4 (18H, s, Pyrazole).

Example 22

4-(4-(6-methyl-7H-pyrrolo[2,3-d]pyrimidinyl)amino)-N-(4-((4-morpholinyl)methyl)phenyl)-1H-3-pyrazolecarboxamide (I-14)

Compound I-14 (61 mg) was prepared in a similar manner as I-1, using 130 mg (0.42 mmol) of N-(4-((4-morpholinyl)methyl)phenyl)-4-amino-1H-3-pyrazolecarboxamide and 70 mg (0.42 mmol) of 4-chloro-6-methyl-7H-pyrrolo[2,3-d]pyrimidine as starting materials. Yield: 33.7%; mp: 271-273° C., MS [M+H]$^+$ 433.3.

$^1$H-NMR [300 MHz, DMSO-d$_6$]: δ2.3 (7H, m, —CH$_2$—×2, —CH$_3$), 2.4 (2H, s, —CH$_2$—), 3.6 (4H, t, J=4.4 Hz, —CH$_2$—×2), 6.5 (1H, s, ArH), 7.3 (2H, d, J=8.4 Hz, ArH), 7.8 (2H, d, J=8.4 Hz, ArH), 8.4 (1H, s, ArH), 8.6 (1H, s, ArH), 9.2 (1H, s, —NHCO—), 10.2 (1H, s, —NH—), 12.0 (1H, s, Pyrrole), 13.4 (1H, s, Pyrazole).

Example 23

4-(4-(5-methyl-7H-pyrrolo[2,3-d]pyrimidinyl)amino)-N-(4-((4-methyl-1-piperazinyl)methyl)phenyl)-1H-3-pyrazolecarboxamide (I-15)

Compound I-15 (53 mg) was prepared in a similar manner as I-1, using 132 mg (0.45 mmol) of N-(4-((4-methyl-1-piperazinyl)methyl)phenyl-4-amino-1H-3-pyrazolecarboxamide and 70 mg (0.45 mmol) of 4-chloro-5-methyl-7H-pyrrolo[2,3-d]pyrimidine as starting materials. Yield: 28.3%; mp: 258-261° C. MS [M+H]$^+$ 446.3.

$^1$H-NMR [300 MHz, DMSO-d$_6$]: δ2.1 (3H, s, —CH$_3$), 2.2-2.4 (8H, m, —CH$_2$—×4), 2.6 (3H, s, —CH$_3$), 3.4 (2H, s, —CH$_2$—), 7.3 (2H, d, J=8.4 Hz, ArH), 7.6 (1H, s, ArH), 7.8 (2H, d, J=8.4 Hz, ArH), 8.4 (1H, s, ArH), 8.6 (1H, s, ArH), 9.2 (1H, s, —NHCO—), 10.2 (1H, s, —NH—), 12.0 (1H, s, Pyrrole), 13.4 (1H, s, Pyrazole).

Example 24

4-(4-(5-methyl-7H-pyrrolo[2,3-d]pyrimidinyl)amino)-N-(4-((4-morpholinyl)methyl)phenyl)-1H-3-pyrazolecarboxamide (I-16)

Compound I-16 (62 mg) was prepared in a similar manner as I-1, using 130 mg (0.45 mmol) of N-(4-((4-morpholinyl)methyl)phenyl)-4-amino-1H-3-pyrazolecarboxamide and 70 mg (0.45 mmol) of 4-chloro-5-methyl-7H-pyrrolo[2,3-d]pyrimidine as starting materials. Yield: 34.3%; mp: 267-269° C., MS [M+H]$^+$ 433.3.

$^1$H-NMR [300 MHz, DMSO-d$_6$]: δ2.3 (4H, t, J=4.4 Hz, —CH$_2$—×2), 2.4 (2H, s, —CH$_2$—), 2.6 (3H, s, —CH$_3$), 3.6 (4H, s, =4.4 Hz, —CH$_2$—×2), 7.3 (2H, d, J=8.4 Hz, ArH), 7.6 (1H, s, ArH), 7.8 (2H, d, J=8.4 Hz, ArH), 8.4 (1H, s, ArH), 8.6 (1H, s, ArH), 9.2 (1H, s, —NHCO—), 10.2 (1H, s, —NH—), 12.0 (1H, s, Pyrrole), 13.4 (1H, s, Pyrazole).

Example 25

4-(4-(5H-pyrrolo[3,2-d]pyrimidinyl)amino)-N-(4-((4-methyl-1-piperazinyl)methyl)phenyl)-1H-3-pyrazolecarboxamide (I-17)

Compound I-17 (50 mg) was prepared in a similar manner as I-1, using 144 mg (0.46 mmol) of N-(4-((4-methyl-1-piperazinyl)methyl)phenyl-4-amino-1H-3-pyrazolecarboxamide and 70 mg (0.46 mmol) of 4-chloro-5H-pyrrolo[3,2-d]pyrimidine as starting materials. Yield: 25.4%; mp: 261-263° C., MS [M+H]$^+$ 432.3.

$^1$H-NMR [300 MHz, DMSO-d$_6$]: δ2.1 (3H, s, —CH$_3$), 2.2-2.4 (8H, m, —CH$_2$—×4), 3.4 (2H, s, —CH$_2$—), 7.3 (2H, d, J=8.4 Hz, ArH), 7.6 (1H, s, ArH), 7.8 (2H, d, J=8.4 Hz, ArH), 8.2 (1H, s, ArH), 8.4 (1H, s, ArH), 8.6 (1H, s, ArH), 9.2 (1H, s, —NHCO—), 10.2 (1H, s, —NH—), 12.0 (1H, s, Pyrazole), 13.4 (1H, s, Pyrazole).

Example 26

4-(4-(5H-pyrrolo[3,2-d]pyrimidinyl)amino)-N-(4-((4-morpholinyl)methyl)phenyl)-1H-3-pyrazolecarboxamide (I-18)

Compound I-18 (67 mg) was prepared in a similar manner as I-1, using 142 mg (0.46 mmol) of N-(4-((4-morpholinyl)methyl)phenyl)-4-amino-1H-3-pyrazolecarboxamide and 70 mg (0.46 mmol) of 4-chloro-5H-pyrrolo[3,2-d]pyrimidine as starting materials. Yield: 35.1%; mp: 258-260° C., MS [M+H]$^+$ 419.3.

$^1$H-NMR [300 MHz, DMSO-d$_6$]: δ2.3 (4H, t, J=4.4 Hz, —CH$_2$—×2), 2.4 (2H, s, —CH$_2$—), 3.6 (4H, t, J=4.4 Hz, —CH$_2$—×2), 7.3 (2H, d, J=8.4 Hz, ArH), 7.6 (1H, s, ArH), 7.8 (2H, d, J=8.4 Hz, ArH), 8.2 (1H, s, ArH), 8.4 (1H, s,

ArH), 8.6 (18H, s, ArH), 9.2 (1H, s, —NHCO—), 10.2 (1H, s, —NH—), 12.0 (1H, s, Pyrrole), 13.4 (1H, s, Pyrazole).

Example 27

4-(4-(6-methyl-5H-pyrrolo[3,2-d]pyrimidinyl) amino)-N-(4-((4-methyl-1-piperazinyl)methyl)phenyl)-1H-3-pyrazolecarboxamide (I-19)

Compound I-19 (55 mg) was prepared in a similar manner as I-1, using 132 mg (0.42 mmol) of N-(4-((4-methyl-1-piperazinyl)methyl)phenyl-4-amino-1H-3-pyrazolecarboxamide and 70 mg (0.42 mmol) of 4-chloro-6-methyl-5H-pyrrolo[3,2-d]pyrimidine as starting materials. Yield: 29.4%; mp: 265-267° C., MS [M+H]$^+$ 446.3.

$^1$H-NMR [300 MHz, DMSO-d$_6$]: δ2.1 (3H, s, —CH$_3$), 2.2-2.4 (8H, m, —CH$_2$—×4), 2.6 (3H, s, —CH$_3$), 3.4 (2H, s, —CH$_2$—), 7.3 (2H, d, J=8.4 Hz, ArH), 7.6 (1H, s, ArH), 7.8 (2H, d, J=8.4 Hz, ArH), 8.4 (1H, s, ArH), 8.6 (1H, s, ArH), 9.2 (1H, s, —NHCO—), 10.2 (1H, s, —NH—), 12.0 (1H, s, Pyrrole), 13.4 (1H, s, Pyrazole).

Example 28

4-(4-(6-methyl-5H-pyrrolo[3,2-d]pyrimidinyl) amino)-N-(4-((4-morpholinyl)methyl)phenyl)-1H-3-pyrazolecarboxamide (I-20)

Compound I-20 (69 mg) was prepared in a similar manner as I-1, using 130 mg (0.42 mmol) of N-(4-((4-morpholinyl)methyl)phenyl-4-amino-1H-3-pyrazolecarboxamide and 70 mg (0.42 mmol) of 4-chloro-6-methyl-5H-pyrrolo[3,2-d]pyrimidine as starting materials. Yield: 38.1%; mp: 268-270° C. MS [M+H]$^+$ 433.3.

$^1$H-NMR [300 MHz, DMSO-d$_6$]: δ2.3 (4H, t, J=4.4 Hz, —CH$_2$—×2), 2.4 (2H, s, —CH$_2$—), 2.6 (3H, s, —CH$_3$), 3.6 (4H, t, J=4.4 Hz, —CH$_2$—×2), 7.3 (2H, d, J=8.4 Hz, ArH), 7.6 (1H, s, ArH), 7.8 (2H, d, J=8.4 Hz, ArH), 8.4 (1H, s, ArH), 8.6 (1H, s, ArH), 9.2 (1H, s, —NHCO—), 10.2 (1H, s, —NH—), 12.0 (1H, s, Pyrrole), 13.4 (1H, s, Pyrazole).

Example 29

4-(4-furo[2,3-d]pyrimidinylamino)-N-(4-((4-methyl-1-piperazinyl)methyl)phenyl)-1H-3-pyrazolecarboxamide (I-21)

Compound I-21 (45 mg) was prepared in a similar manner as I-1, using 143 mg (0.45 mmol) of N-(4-((4-methyl-1-piperazinyl)methyl)phenyl-4-amino-1H-3-pyrazolecarboxamide and 70 mg (0.45 mmol) of 4-chlorofuro[2,3-d]pyrimidine as starting materials. Yield: 23.0%; mp: 255-257° C., MS [M+H]$^+$ 433.3.

$^1$H-NMR [300 MHz, DMSO-d$_6$]: δ2.1 (3H, s, —CH$_3$), 2.2-2.4 (8H, m, —CH$_2$—×4), 3.4 (2H, s, —CH$_2$—), 7.1 (1H, d, J=2.5 Hz, ArH), 7.2 (2H, d, J=8.4 Hz, ArH), 7.7 (2H, d, J=8.4 Hz, ArH), 8.0 (1H, d, J=2.5 Hz, ArH), 8.4 (1H, s, ArH), 8.5 (1H, s, ArH), 9.7 (1H, s, —NHCO—), 10.2 (1H, s, —NH—), 13.4 (1H, s, Pyrazole).

Example 30

4-(4-furo[2,3-d]pyrimidinylamino)-N-(4-((4-morpholinyl)methyl)phenyl)-1H-3-pyrazolecarboxamide (I-22)

Compound I-22 (53 mg) was prepared in a similar manner as I-1, using 141 mg (0.45 mmol) of N-(4-((4-morpholinyl)methyl)phenyl)-4-amino-1H-3-pyrazolecarboxamide and 70 mg (0.45 mmol) 4-chlorofuro[2,3-d]pyrimidine as starting materials. Yield: 27.9%; mp: >280° C., MS [M+H]$^+$ 420.3.

$^1$H-NMR [300 MHz, DMSO-d$_6$]: δ2.3 (4H, t, J=4.2 Hz, —CH$_2$—×2), 3.4 (2H, s, —CH$_2$—), 3.6 (4H, t, J=4.2 Hz, —CH$_2$—×2), 7.1 (1H, d, J=2.5 Hz, ArH), 7.3 (2H, d, J=8.2 Hz, ArH), 7.8 (2H, d, =8.2 Hz, ArH), 8.0 (1H, d, J=2.5 Hz, ArH), 8.4 (1H, s, ArH), 8.5 (1, s, ArH), 9.7 (1H, s, —NHCO—), 10.2 (1H, s, —NH—), 13.4 (1H, s, Pyrazole).

Example 31

4-(4-furo[3,2-d]pyrimidinylamino)-N-(4-((4-methyl-1-piperazinyl)methyl)phenyl)-1H-3-pyrazolecarboxamide (I-23)

Compound I-23 (71 mg) was prepared in a similar manner as I-1, using 143 mg (0.45 mmol) of N-(4-((4-methyl-1-piperazinyl)methyl)phenyl-4-amino-1H-3-pyrazolecarboxamide and 70 mg (0.45 mmol) of 4-chlorofuro[3,2-d]pyrimidine as starting materials. Yield: 36.2%; mp: 277-279° C., MS [M+H]$^+$ 433.3.

$^1$H-NMR [300 MHz, DMSO-d$_6$]: δ2.1 (3H, s, —CH$_3$), 2.2-2.4 (8H, m, —CH$_2$—×4), 3.4 (2H, s, —CH$_2$—), 7.2 (2H, d, J=8.4 Hz, ArH), 7.7 (2H, d, J=8.4 Hz, ArH), 7.8 (1H, d, J=2.5 Hz, ArH), 8.2 (1H, d, J=2.5 Hz, ArH), 8.4 (1H, s, ArH), 8.5 (1H, s, ArH), 9.7 (1H, s, —NHCO—), 10.2 (1H, s, —NH—), 13.4 (1H, s, Pyrazole).

Example 32

4-(4-furo[3,2-d]pyrimidinylamino)-N-(4-((4-morpholinyl)methyl)phenyl)-1H-3-pyrazolecarboxamide (I-24)

Compound I-24 (80 mg) was prepared in a similar manner as I-1, using 141 mg (0.45 mmol) of N-(4-((4-morpholinyl)methyl)phenyl)-4-amino-1H-3-pyrazolecarboxamide and 70 mg (0.45 mmol) of 4-chlorofuro[3,2-d]pyrimidine as starting materials. Yield: 42.1%; mp: 271-273° C., MS [M+H]$^+$ 420.3.

$^1$H-NMR [300 MHz, DMSO-d$_6$]: δ2.3 (4H, t, J=4.2 Hz, —CH$_2$—×2), 3.4 (2H, s, —CH$_2$—), 3.6 (4H, t, J=4.2 Hz, —CH$_2$—×2), 7.3 (2H, d, J=8.2 Hz, ArH), 7.7 (2H, d, J=8.2 Hz, ArH), 7.8 (1H, d, J=2.5 Hz, ArH), 8.2 (1H, d, J=2.5 Hz, ArH), 8.4 (1H, s, ArH), 8.5 (1H, s, ArH), 9.7 (1H, s, —NHCO—), 10.2 (1H, s, —NH—), 13.4 (1H, s, Pyrazole).

Example 33

4-(4-thieno[3,2-c]pyridylamino)-N-(4-((4-methyl-1-piperazinyl)methyl)phenyl)-1H-3-pyrazolecarboxamide (I-25)

129 mg (0.41 mmol) of N-(4-((4-methyl-1-piperazinyl)methyl)phenyl-4-amino-1H-3-pyrazolecarboxamide, 70 mg (0.41 mmol) of 4-chlorothieno[3,2-c]pyridine and 1 ml of glacial acetic acid were dissolved in isopropanol (8 mL). The reaction mixture was microwaved (300 W) at 190° C. for 30 min. Isopropanol was distilled off under reduced pressure and the resulting solid was dissolved with distilled water. Saturated aqueous sodium hydroxide solution was used to adjust pH to 8~9 and the mixture was extracted with ethyl acetate for three times (50 mL×3). The extracts were combined and dried with dry magnesium sulfate. After suction filtration, the solvent was distilled off under reduced pressure to give yellowish solid. The crude was subjected to column chromatography (mobile phase: methanol:chloroform=1:15) to give I-25 (67 mg). Yield: 36.4%; mp: 268-270° C., MS [M+H]$^+$ 448.3.

$^1$H-NMR [300 MHz, DMSO-d$_6$]: δ2.1 (3H, s, —CH$_3$), 2.2-2.4 (8H, m, —CH$_2$—×4), 3.4 (21, s, —CH$_2$—), 6.7 (1H, d, J=8.0 Hz, ArH), 7.3 (2H, d, J=8.4 Hz, ArH), 7.5 (1H, d, J=5.4 Hz, ArH), 7.7-7.8 (3H, m, ArH), 7.9 (1H, d, J=8.0 Hz, ArH), 8.5 (1H, s, ArH), 10.0 (1H, s, —NHCO—), 10.3 (1H, s, —NH—), 13.5 (1H, s, Pyrazole).

Example 34

4-(4-thieno[3,2-c]pyridylamino)-N-(4-((4-morpholinyl)methyl)phenyl)-1H-3-pyrazolecarboxamide (I-26)

Compound I-26 (71 mg) was prepared in a similar manner as I-25, using 128 mg (0.41 mmol) of N-(4-((4-morpholinyl)methyl)phenyl)-4-amino-1H-3-pyrazolecarboxamide and 70 mg (0.41 mmol) of 4-chlorothieno[3,2-c]pyridine as starting materials. Yield: 39.7%; mp: 269-271° C., MS [M+H]$^+$ 435.3.

$^1$H-NMR [300 MHz, DMSO-d$_6$]: δ2.3 (4H, t, J=4.2 Hz, —CH$_2$—×2), 3.4 (2H, s, —CH$_2$—), 3.5 (4H, t, J=4.2 Hz, —CH$_2$—×2), 6.7 (1H, d, J=8.0 Hz, ArH), 7.3 (2H, d, J=8.4 Hz, ArH), 7.5 (1H, d, J=5.4 Hz, ArH), 7.7-7.8 (3H, m, ArH), 7.9 (1H, d, J=8.0 Hz, ArH), 8.5 (1H, s, ArH), 9.9 (1H, s, —NHCO—), 10.3 (1H, s, —NH—), 13.5 (1H, s, Pyrazole).

Example 35

4-(4-(2-methylthieno[3,2-c]pyridyl)amino)-N-(4-((4-methyl-1-piperazinyl)methyl)phenyl)-1H-3-pyrazolecarboxamide (I-27)

Compound I-27 (68 mg) was prepared in a similar manner as I-25, using 121 mg (0.38 mmol) of N-(4-((4-methyl-1-piperazinyl)methyl)phenyl-4-amino-1H-3-pyrazolecarboxamide and 70 mg (0.38 mmol) of 4-chloro-2-methylthieno[3,2-c]pyridine as starting materials. Yield: 38.6%; mp: 267-269° C., MS [M+H]$^+$ 462.3.

$^1$H-NMR [300 MHz, DMSO-d$_6$]: δ2.1 (3H, s, —CH$_3$), 2.6 (3H, s, —CH$_3$), 2.2-2.4 (8H, m, —CH$_2$—×4), 3.4 (2H, s, —CH$_2$—), 6.7 (1H, d, J=8.0 Hz, ArH), 7.2 (1H, s, ArH), 7.3 (2H, d, J 8.4 Hz, ArH), 7.8 (2H, d, J=8.4 Hz, ArH), 7.9 (1H, d, J=8.0 Hz, ArH), 8.5 (1H, s, ArH), 10.0 (1H, s, —NHCO—), 10.3 (1H, s, —NH—), 13.5 (1H, s, Pyrazole).

Example 36

4-(4-(2-methylthieno[3,2-c]pyridyl)amino)-N-(4-((4-morpholinyl)methyl)phenyl)-1H-3-pyrazolecarboxamide (I-28)

Compound I-28 (59 mg) was prepared in a similar manner as I-25, using 119 mg (0.38 mmol) of N-(4-((4-morpholinyl)methyl)phenyl)-4-amino-1H-3-pyrazolecarboxamide and 70 mg (0.38 mmol) of 4-chloro-2-methylthieno[3,2-c]pyridine as starting materials. Yield: 34.5%; mp: 265-267° C., MS [M+H]$^+$ 449.3.

$^1$H-NMR [300 MHz, DMSO-d$_6$]: δ2.3 (4H, t, J=4.2 Hz, —CH$_2$—×2), 2.6 (3H, s, —CH$_3$), 3.4 (2H, s, —CH$_2$—), 3.5 (4H, t, J=4.2 Hz, —CH$_2$—×2), 6.7 (1H, d, J=8.0 Hz, ArH), 7.2 (1H, s, ArH), 7.3 (2H, d, J=8.4 Hz, ArH), 7.8 (2H, d, J=8.4 Hz, ArH), 7.9 (1H, d, J=8.0 Hz, ArH), 8.5 (1H, s, ArH), 9.9 (1H, s, —NHCO—), 10.3 (1H, s, —NH—), 13.5 (1H, s, Pyrazole).

Example 37

4-(7-thieno[2,3-c]pyridylamino)-N-(4-((4-methyl-1-piperazinyl)methyl)phenyl)-1H-3-pyrazolecarboxamide (I-29)

Compound I-29 (59 mg) was prepared in a similar manner as I-25, using 129 mg (0.41 mmol) of N-(4-((4-methyl-1-piperazinyl)methyl)phenyl-4-amino-1H-3-pyrazolecarboxamide and 70 mg (0.41 mmol) of 7-chlorothieno[2,3-c]pyridine as starting materials. Yield: 30.4%; mp: 274-276° C., MS [M+H]$^+$ 448.3.

$^1$H-NMR [300 MHz, DMSO-d$_6$]: δ2.2 (3H, s, —CH$_3$), δ2.3-2.5 (8H, m, —CH$_2$—×4), 3.4 (2H, a, —CH$_2$—), 6.7 (1H, d, J=8.0 Hz, ArH), 7.3 (2H, d, J=8.4 Hz, ArH), 7.5 (1H, d, J=5.3 Hz, ArH), 7.8 (2H, d, J=8.4 Hz, ArH), 7.9 (1H, d, J=8.0 Hz, ArH), 8.2 (1H, d, J=5.3 Hz, ArH), 8.5 (1H, s, ArH), 9.7 (1H, s, —NHCO—), 10.3 (1H, s, —NH—), 13.5 (1H, s, Pyrazole).

Example 38

4-(7-thieno[2,3-c]pyridylamino)-N-(4-((4-morpholinyl)methyl)phenyl)-1H-3-pyrazolecarboxamide (I-30)

Compound I-30 (81 mg) was prepared in a similar manner as I-25, using 128 mg (0.41 mmol) of N-(4-((4-morpholinyl)methyl)phenyl)-4-amino-1H-3-pyrazolecarboxamide and 70 mg (0.41 mmol) of 7-chlorothieno[2,3-c]pyridine as starting materials. Yield: 45.3%; mp: 271-273° C., MS [M+H]$^+$ 435.3.

$^1$H-NMR [300 MHz, DMSO-d$_6$]: δ2.4 (4H, t, J=4.2 Hz, —CH$_2$—×2), 3.4 (2H, s, —CH$_2$—), 3.6 (4H, t, J=4.2 Hz, —CH$_2$—×2), 6.7 (1H, d, J=8.0 Hz, ArH), 7.3 (2H, d, J=8.4 Hz, ArH), 7.5 (1H, d, J=5.2 Hz, ArH), 7.8 (2H, d, J=8.4 Hz, ArH), 7.9 (1H, d, J=8.0 Hz, ArH), 8.3 (1H, d, J=5.2 Hz, ArH), 8.5 (1H, s, ArH), 9.7 (1H, s, —NHCO—), 10.3 (1H, s, —NH—), 13.5 (1H, s, Pyrazole).

Example 39

4-(7-(3-methylthieno[2,3-c]pyridyl)amino)-N-(4-((4-methyl-1-piperazinyl)methyl)phenyl)-1H-3-pyrazolecarboxamide (I-31)

Compound I-31 (71 mg) was prepared in a similar manner as I-25, using 121 mg (0.38 mmol) of N-(4-((4-methyl-1-piperazinyl)methyl)phenyl-4-amino-1H-3-pyrazolecarboxamide and 70 mg (0.38 mmol) of 7-chloro-3-methylthieno[2,3-c]pyridine as starting materials. Yield: 40.3%; mp: 258-260° C., MS [M+H]$^+$ 462.3.

$^1$H-NMR [300 MHz, DMSO-d$_6$]: δ2.2 (3H, s, —CH$_3$), δ2.3-2.5 (8H, m, —CH$_2$—×4), 2.6 (3H, s, —CH$_3$), 3.4 (2H, s, —CH$_2$—), 6.7 (1H, d, J=8.0 Hz, ArH), 7.3 (2H, d, J=8.4 Hz, ArH), 7.8 (2H, d, J=8.4 Hz, ArH), 7.9 (1H, d, J=8.0 Hz, ArH), 8.2 (1H, s, ArH), 8.5 (1H, s, ArH), 9.7 (1H, s, —NHCO—), 10.3 (1H, s, —NH—), 13.5 (1H, s, Pyrazole).

Example 40

4-(7-(3-methylthieno[2,3-c]pyridyl)amino)-N-(4-((4-morpholinyl)methy)phenyl)-1H-3-pyrazolecarboxamide (I-32)

Compound I-32 (71 mg) was prepared in a similar manner as I-25, using 119 mg (0.38 mmol) of N-(4-((4-morpholinyl)

methyl)phenyl)-4-amino-1H-3-pyrazolecarboxamide and 70 mg (0.38 mmol) of 7-chloro-3-methylthieno[2,3-c]pyridine as starting materials. Yield: 42.7%; mp: 275-277° C., MS [M+H]$^+$ 449.3.

$^1$H-NMR [300 MHz, DMSO-d$_6$]: δ2.4 (4H, t, J=4.2 Hz, —CH$_2$—×2), 2.6 (3H, s, —CH$_3$), 3.4 (2H, s, —CH$_2$—), 3.6 (4H, t, J=4.2 Hz, —CH$_2$—×2), 6.7 (1H, d, J=8.0 Hz, ArH), 7.3 (2H, d, J=8.4 Hz, ArH), 7.8 (2H, d, =8.4 Hz, ArH), 7.9 (1H, d, J=8.0 Hz, ArH), 8.3 (1H, s, ArH), 8.5 (1H, s, ArH), 9.7 (1H, s, —NHCO—), 10.3 (1H, s, —NH—), 13.5 (1H, s, Pyrazole).

Example 41

4-(4-furo[3,2-c]pyridylamino)-N-(4-((4-methyl-1-piperazinyl)menthyl)phenyl)-1H-3-pyrazolecarboxamide (I-33)

Compound I-33 (75 mg) was prepared in a similar manner as I-25, using 120 mg (0.46 mmol) of N-(4-((4-methyl-1-piperazinyl)methyl)phenyl-4-amino-1H-3-pyrazolecarboxamide and 70 mg (0.46 mmol) of 4-chlorofuro[3,2-c]pyridine as starting materials. Yield: 38.1%; mp: 268-270° C., MS [M+H]$^+$ 432.3.

$^1$H-NMR [300 MHz, DMSO-d$_6$]: δ2.1 (3H, s, —CH$_3$), 2.2-2.4 (8H, m, —CH$_2$—×4), 3.4 (2H, s, —CH$_2$—), 6.7 (1H, d, J=8.0 Hz, ArH), 7.1 (1H, d, J=2.5 Hz, ArH), 7.2 (2H, d, J=8.4 Hz, ArH), 7.7 (2H, d, J=8.4 Hz, ArH), 7.9 (1H, d, J=8.0 Hz, ArH), 8.0 (1H, d, J=2.5 Hz, ArH), 8.4 (1H, s, ArH), 9.7 (1H, s, —NHCO—), 10.2 (1H, s, —NH—), 13.4 (1H, s, Pyrazole).

Example 42

4-(4-furo[3,2-c]pyridylamino)-N-(4-((4-morpholinyl)methyl)phenyl)-1H-3-pyrazolecarboxamide (I-34)

Compound I-34 (68 mg) was prepared in a similar manner as I-25, using 119 mg (0.46 mmol) of N-(4-((4-morpholinyl)methyl)phenyl)-4-amino-1H-3-pyrazolecarboxamide and 70 mg (0.46 mmol) of 4-chlorofuro[3,2-c]pyridine as starting materials. Yield: 35.6%; mp: 268-271° C., MS [M+H]$^+$ 419.3.

$^1$H-NMR [300 MHz, DMSO-d$_6$]: δ2.3 (4H, t, J=4.2 Hz, —CH$_2$—×2), 3.4 (2H, s, —CH$_2$—), 3.6 (4H, t, J=4.2 Hz, —CH$_2$—×2), 6.7 (1H, d, =8.0 Hz, ArH), 7.1 (1H, d, J=2.5 Hz, ArH), 7.3 (2H, d, J=8.2 Hz, ArH), 7.8 (2H, d, J=8.2 Hz, ArH), 7.9 (1H, d, J=8.0 Hz, ArH), 8.0 (1H, d, J=2.5 Hz, ArH), 8.4 (1H, s, ArH), 9.7 (1H, s, —NHCO—), 10.2 (1H, —N—), 13.4 (1H, s, Pyrazole).

Example 43

4-(4-(2-methylfuro[3,2-c]pyridyl)amino)-N-(4-((4-methyl-1-piperazinyl)methyl)phenyl)-1H-3-pyrazolecarboxamide (I-35)

Compound I-35 (47 mg) was prepared in a similar manner as I-25, using 144 mg (0.42 mmol) of N-(4-((4-methyl-1-piperazinyl)methyl)phenyl-4-amino-1H-3-pyrazolecarboxamide and 70 mg (0.42 mmol) of 4-chloro-2-methylfuro[3,2-c]pyridine as starting materials. Yield: 25.1%; mp: 274-276° C., MS [M+H]$^+$ 446.3.

$^1$H-NMR [300 MHz, DMSO-d$_6$]: δ2.1 (3H, s, —CH$_3$), 2.2-2.4 (8H, m, —CH$_2$—×4), 2.6 (3H, s, —CH$_3$), 3.4 (2H, s, —CH$_2$—), 6.7 (1H, d, J=8.0 Hz, ArH), 7.1 (1H, s, ArH), 7.2 (2H, d, J=8.4 Hz, ArH), 7.7 (2H, d, J=8.4 Hz, ArH), 7.9 (1H, d, J=8.0 Hz, ArH), 8.4 (1H, s, ArH), 9.7 (1H, s, —NHCO—), 102 (1H, s, —NH—), 13.4 (1H, s, Pyrazole).

Example 44

4-(4-(2-methylfuro[3,2-c]pyridyl)amino)-N-(4-((4-morpholinyl)methyl)phenyl)-1H-3-pyrazolecarboxamide (I-36)

Compound I-36 (63 mg) was prepared in a similar manner as I-25, using 142 mg (0.42 mmol) of N-(4-((4-morpholinyl)methyl)phenyl)-4-amino-1H-3-pyrazolecarboxamide and 70 mg (0.42 mmol) of 4-chloro-2-methylfuro[3,2-c]pyridine as starting materials. Yield: 34.8%; mp: 275-277° C., MS [M+H]$^+$ 433.3.

$^1$H-NMR [300 MHz, DMSO-d$_6$]: δ2.3 (4H, t, J=4.2 Hz, —CH$_2$—×2), 2.6 (3H, s, —CH$_3$), 3.4 (2H, s, —CH$_2$—), 3.6 (4H, t, J=4.2 Hz, —CH$_2$—×2), 6.7 (1H, d, J=8.0 Hz, ArH), 7.1 (1H, s, ArH), 7.3 (2H, d, J=8.2 Hz, ArH), 7.8 (2H, d, J=8.2 Hz, ArH), 7.9 (1H, d, J=8.0 Hz, ArH), 8.4 (1H, s, ArH), 9.7 (1H, s, —NHCO—), 10.2 (1H, s, —NH—), 13.4 (1H, s, Pyrazole).

Example 45

4-(7-furo[2,3-c]pyridylamino)-N-(4-((4-methyl-1-piperazinyl)methyl)phenyl)-1H-3-pyrazolecarboxamide (I-37)

Compound I-37 (45 mg) was prepared in a similar manner as I-25, using 132 mg (0.46 mmol) of N-(4-((4-methyl-1-piperazinyl)methyl)phenyl-4-amino-1H-3-pyrazolecarboxamide and 70 mg (0.46 mmol) of 7-chlorofuro[2,3-c]pyridine as starting materials. Yield: 22.8%; mp: 258-261° C., MS [M+H]$^+$ 432.3.

$^1$H-NMR [300 MHz, DMSO-d$_6$]: δ2.1 (3H, s, —CH$_3$), 2.2-2.4 (8H, m, —CH$_2$—×4), 3.4 (2H, s, —CH$_2$—), 6.7 (1H, d, J=8.0 Hz, ArH), 7.2 (1H, d, J=8.4 Hz, ArH), 7.7 (2H, d, J=8.4 Hz, ArH), 7.8 (1H, d, J=2.5 Hz, ArH), 7.9 (1H, d, J=8.0 Hz, ArH), 8.3 (1H, d, J=2.5 Hz, ArH), 8.4 (1H, s, ArH), 9.7 (1H, s, —NHCO—), 10.2 (1H, s, —NH—), 13.4 (1H, s, Pyrazole).

Example 46

4-(7-furo[2,3-c]pyridylamino)-N-(4-((4-morpholinyl)methyl)phenyl)-1H-3-pyrazolecarboxamide (I-38)

Compound I-38 (47 mg) was prepared in a similar manner as I-25, using 130 mg (0.46 mmol) N-(4-((4-morpholinyl)methyl)phenyl)-4-amino-1H-3-pyrazolecarboxamide and 70 mg (0.46 mmol) of 7-chlorofuro[2,3-c]pyridine as starting materials. Yield: 24.6%; mp: 268-272° C., MS [M+H]$^+$ 419.3.

$^1$H-NMR [300 MHz, DMSO-d$_6$]: δ2.3 (4H, t, J=4.2 Hz, —CH$_2$—×2), 3.4 (2H, s, —CH$_2$—), 3.6 (4H, t, J=4.2 Hz, —CH$_2$—×2), 6.7 (1H, d, J=8.0 Hz, ArH), 7.3 (2H, d, J=8.2 Hz, ArH), 7.7 (2H, d, J=8.2 Hz, ArH), 7.8 (1H, d, J=2.5 Hz, ArH), 7.9 (1H, d, J=8.0 Hz, ArH), 8.3 (1H, d, J=2.5 Hz, ArH), 8.4 (1H, s, ArH), 9.7 (1H, s, —NHCO—), 10.2 (1H, s, —NH—), 13.4 (1H, s, Pyrazole).

Example 47

4-(7-furo[3,2-b]pyridylamino)-N-(4-((4-methyl-1-piperazinyl)methyl)phenyl)-1H-3-pyrazolecarboxamide (I-39)

Compound I-39 (48 mg) was prepared in a similar manner as I-25, using 144 mg (0.46 mmol) of N-(4-((4-methyl-1-piperazinyl)methyl)phenyl-4-amino-1H-3-pyrazolecarboxamide and 70 mg (0.46 mmol) of 7-chlorofuro[3,2-b]pyridine as starting materials. Yield: 24.4%; mp: 268-270° C., MS [M+H]+ 432.3.
$^1$H-NMR [300 MHz, DMSO-d$_6$]: δ2.1 (3H, s, —CH$_3$), 2.2-2.4 (8H, m, —CH$_2$—×4), 3.4 (2H, s, —CH$_2$—), 6.7 (1H, d, J=8.0 Hz, ArH), 7.2 (2H, d, J=8.4 Hz, ArH), 7.4 (1H, s, ArH), 7.7 (2H, d, J 8.4 Hz, ArH), 7.8 (1H, d, J=2.5 Hz, ArH), 8.2 (1H, d, J=8.0 Hz, ArH), 8.3 (1H, d, J=2.5 Hz, ArH), 8.4 (1H, s, ArH), 9.7 (1H, s, —NHCO—), 10.2 (1H, s, —NH—), 13.4 (1H, s, Pyrazole).

Example 48

4-(7-furo[3,2-b]pyridylamino)-N-(4-((4-morpholinyl)methyl)phenyl)-1H-3-pyrazolecarboxamide (I-40)

Compound I-40 (53 mg) was prepared in a similar manner as I-25, using 142 mg (0.46 mmol) of N-(4-((4-morpholinyl)methyl)phenyl)-4-amino-1H-3-pyrazolecarboxamide and 70 mg (0.46 mmol) of 7-chlorofuro[3,2-b]pyridine as starting materials. Yield: 27.7%; mp: 275-278° C., MS [M+H]+ 419.3.
$^1$H-NMR [300 MHz, DMSO-d$_6$]: δ2.3 (4H, t, J=4.2 Hz, —CH$_2$—×2), 3.4 (2H, s, —CH$_2$—), 3.6 (4H, t, J=4.2 Hz, —CH$_2$—×2), 6.7 (1H, d, J=8.0 Hz, ArH), 7.3 (2H, d, J=8.2 Hz, ArH), 7.7 (2H, d, J=8.2 Hz, ArH), 7.8 (1H, d, J=2.5 Hz, ArH), 8.2 (1H, d, J=8.0 Hz, ArH), 8.3 (1H, d, J=2.5 Hz, ArH), 8.4 (1H, s, ArH), 9.7 (1H, s, —NHCO—), 10.2 (1H, s, —NH—), 13.4 (1H, s, Pyrazole).

Example 49

4-(4-furo[2,3-b]pyridylamino)-N-(4-((4-methyl-1-piperazinyl)methyl)phenyl)-1H-3-pyrazolecarboxamide (I-41)

Compound I-41 (64 mg) was prepared in a similar manner as I-25, using 144 mg (0.46 mmol) of N-(4-((4-methyl-1-piperazinyl)methyl)phenyl-4-amino-1H-3-pyrazolecarboxamide and 70 mg (0.46 mmol) of 4-chlorofuro[2,3-b]pyridine as starting materials. Yield: 32.5%; mp: 273-276° C., MS [M+H]+ 432.3.
$^1$H-NMR [300 MHz, DMSO-d$_6$]: δ2.1 (3H, s, —CH$_3$), 2.2-2.4 (8H, m, —CH$_2$—×4), 3.4 (2H, s, —CH$_2$—), 6.7 (1H, d, J=8.0 Hz, ArH), 7.1 (1H, d, J=2.5 Hz, ArH), 7.2 (2H, d, J=8.4 Hz, ArH), 7.7 (2H, d, J=8.4 Hz, ArH), 8.0 (1H, d, J=2.5 Hz, ArH), 8.2 (1H, d, J=8.0 Hz, ArH), 8.4 (1H, s, ArH), 9.7 (1H, s, —NHCO—), 10.2 (1H, s, —NH—), 13.4 (1H, s, Pyrazole).

Example 50

4-(4-furo[2,3-b]pyridylamino)-N-(4-((4-morpholinyl)methyl)phenyl)-1H-3-pyrazolecarboxamide (I-42)

Compound I-42 (56 mg) was prepared in a similar manner as I-25, using 142 mg (0.46 mmol) of N-(4-((4-morpholinyl)phenyl)-4-amino-1H-3-pyrazolecarboxamide and 70 mg (0.46 mmol) of 4-chlorofuro[2,3-b]pyridine as starting materials. Yield: 29.3%; mp: 269-271° C., MS [M+H]+ 419.3.
$^1$H-NMR [300 MHz, DMSO-d$_6$]: δ2.3 (4H, t, J=4.2 Hz, —CH$_2$—×2), 3.4 (2H, s, —CH$_2$—), 3.6 (4H, t, J=4.2 Hz, —CH$_3$×2), 6.7 (1H, d, J=8.0 Hz, ArH), 7.1 (1H, d, J=2.5 Hz, ArH), 7.3 (2H, d, J=8.2 Hz, ArH), 7.8 (2H, d, J=8.2 Hz, ArH), 8.0 (1H, d, J=2.5 Hz, ArH), 8.2 (1H, d, J=8.0 Hz, ArH), 8.4 (1H, s, ArH), 9.7 (1H, s, —NHCO—), 10.2 (1, s, —NH—), 13.4 (1H, s, Pyrazole).

Example 51

4-(7-(1H-pyrrolo[2,3-c]pyridyl)amino)-N-(4-((4-methyl-1-piperazinyl)methyl)phenyl)-1H-3-pyrazolecarboxamide (I-43)

Compound I-43 (64 mg) was prepared in a similar manner as I-25, using 145 mg (0.46 mmol) of N-(4-((4-methyl-1-piperazinyl)methyl)phenyl-4-amino-1H-3-pyrazolecarboxamide and 70 mg (0.46 mmol) of 7-chloro-1H-pyrrolo[2,3-c]pyridine as starting materials. Yield: 32.3%; mp: 279-282° C., MS [M+H]+ 431.3.
$^1$H-NMR [300 MHz, DMSO-d$_6$]: δ2.1 (3H, s, —CH$_3$), 2.2-2.4 (8H, m, —CH$_2$—×4), 3.4 (2H, s, —CH$_2$—), 7.3 (2H, d, J=8.4 Hz, ArH), 7.4 (1H, d, J=8.0 Hz, ArH), 7.6 (1H, s, ArH), 7.8 (2H, d, J=8.4 Hz, ArH), 8.0 (1H, d, J=8.0 Hz, ArH), 8.2 (1H, s, ArH), 8.4 (1H, s, ArH), 9.2 (1H, s, —NHCO—), 10.2 (1H, s, —NH—), 12.0 (1H, s, Pyrrole), 13.4 (1H, s, Pyrazole).

Example 52

4-(7-(1H-pyrrolo[2,3-c]pyridyl)amino)-N-(4-((4-morpholinyl)methyl)phenyl)-1H-3-pyrazolecarboxamide (I-44)

Compound I-44 (52 mg) was prepared in a similar manner as I-25, using 143 mg (0.46 mmol) of N-(4-((4-morpholinyl)methyl)phenyl)-4-amino-1H-3-pyrazolecarboxamide and 70 mg (0.46 mmol) of 7-chloro-1H-pyrrolo[2,3-c]pyridine as starting materials. Yield: 27.1%; mp: 265-267° C., MS [M+H]+ 420.3.
$^1$H-NMR [300 MHz, DMSO-d$_6$]: δ2.3 (4H, t, J=4.4 Hz, —CH$_2$—×2), 2.4 (2H, s, —CH$_2$—), 3.6 (4H, t, J=4.4 Hz, —CH$_2$—×2), 7.3 (2H, d, J=8.4 Hz, ArH), 7.4 (1H, d, J=8.0 Hz, ArH), 7.6 (1H, s, ArH), 7.8 (2H, d, J=8.4 Hz, ArH), 8.0 (1H, d, 0.1=8.0 Hz, ArH), 8.2 (1H, s, ArH), 8.4 (1H, s, ArH), 9.2 (1H, s, —NHCO—), 10.2 (1H, s, —NH—), 12.0 (1H, s, Pyrrole), 13.4 (1H, s, Pyrazole).

Example 53

4-(7-(2-methyl-1H-pyrrolo[2,3-c]pyridyl)amino)-N-(4-((4-methyl-1-piperazinyl)methyl)phenyl)-1H-3-pyrazolecarboxamide (I-45)

Compound I-45 (49 mg) was prepared in a similar manner as I-25, using 132 mg (0.42 mmol) of N-(4-((4-methyl-1-piperazinyl)methyl)phenyl-4-amino-1H-3-pyrazolecarboxamide and 70 mg (0.42 mmol) of 7-chloro-2-methyl-1H-pyrrolo[2,3-c]pyridine as starting materials. Yield: 26.2%; mp: 276-278° C., MS [M+H]+ 445.3.
$^1$H-NMR [300 MHz, DMSO-d$_6$]: δ2.1 (3H, s, —CH$_3$), 2.2-2.4 (8H, m, —CH$_2$—×4), 2.6 (3H, s, —CH$_3$), 3.4 (2H, s, —CH$_2$—), 7.3 (2H, d, J=8.4 Hz, ArH), 7.4 (1H, d, J=8.0 Hz, ArH), 7.6 (1H, s, ArH), 7.8 (2H, d, J=0.0 Hz, ArH), 8.4 Hz, ArH), 8.0 (1, d, J=8.0 Hz, ArH), 0.4 (1H, s, ArH), 9.2 (1H, s, —NHCO—), 10.2 (1H, s, —NH—), 12.0 (1H, s, Pyrrole), 13.4 (1H, s, Pyrazole).

Example 54

4-(7-(2-methyl-1H-pyrrolo[2,3-c]pyridyl)amino)-N-(4-((4-morpholinyl)methyl)phenyl)-1H-3-pyrazole-carboxamide (I-46)

Compound I-46 (73 mg) was prepared in a similar manner as I-25, using 131 mg (0.42 mmol) of N-(4-((4-morpholinyl)methyl)phenyl)-4-amino-1H-3-pyrazolecarboxamide and 70 mg (0.42 mmol) of 7-chloro-2-methyl-1H-pyrrolo[2,3-c]pyridine as starting materials. Yield: 40.1%; mp: 254-258° C., MS [M+H]$^+$ 432.3.

$^1$H-NMR [300 MHz, DMSO-d$_6$]: δ2.3 (4H, t, J=4.4 Hz, —CH$_2$—×2), 2.4 (2H, s, —CH$_2$—), 2.6 (3H, s, —CH$_3$), 3.6 (4H, t, J=4.4 Hz, —CH$_2$—×2), 7.3 (2H, d, J=8.4 Hz, ArH), 7.4 (1H, d, J=8.0 Hz, ArH), 7.6 (1H, s, ArH), 7.8 (2H, d, J=8.4 Hz, ArH), 8.0 (1H, d, J=8.0 Hz, ArH), 8.4 (1H, s, ArH), 9.2 (1H, s, —NHCO—), 10.2 (1H, s, —NH—), 12.0 (1H, s, Pyrrole), 13.4 (1H, s, Pyrazole).

Example 55

4-(4-(2-methylthieno[3,2-d]pyrimidine)ylamino)-N-(4-((4-methyl-1-piperazinyl)methyl)phenyl)-1H-3-pyrazolecarboxamide (I-47)

Compound I-47 (85 mg) was prepared in a similar manner as I-1, using 120 mg (0.38 mmol) of N-(4-((4-methyl-1-piperazinyl)methyl)phenyl-4-amino-1H-3-pyrazolecarboxamide and 70 mg (0.38 mmol) of 4-chloro-2-methylthieno[3,2-d]pyrimidine as starting materials. Yield: 49.7%; mp: >280° C., MS [M+H]$^+$ 463.3.

$^1$H-NMR [300 MHz, DMSO-d$_6$]: δ2.1 (3H, s, —CH$_3$), 2.2-2.5 (8H, m, —CH$_2$—×4), 2.6 (3H, s, —CH$_3$), 3.4 (2H, s, —CH$_2$—), 7.3 (2H, d, J=8.4 Hz, ArH), 7.4 (1H, d, J=4.1 Hz, ArH), 7.8 (2H, d, J=8.4 Hz, ArH), 8.2 (1H, d, J=4.1 Hz, ArH), 8.6 (1H, s, ArH), 9.6 (1H, 8, —NHCO—), 10.3 (1H, s, —NH—), 13.5 (1H, s, Pyrazole).

Example 56

4-(4-(2-methylthieno[3,2-d]pyrimidine)ylamino)-N-(4-((4-morpholinyl)methyl)phenyl)-1H-3-pyrazole-carboxamide (I-48)

Compound I-48 (93 mg) was prepared in a similar manner as I-1, using 119 mg (0.38 mmol) of N-(4-((4-morpholinyl)methyl)phenyl)-4-amino-1H-3-pyrazolecarboxamide and 70 mg (0.38 mmol) of 4-chloro-2-methylthieno[3,2-d]pyrimidine as starting materials. Yield: 54.4%; mp: 259-262° C., MS [M+H]$^+$ 450.2.

$^1$H-NMR [300 MHz, DMSO-d$_6$]: δ2.3 (4H, t, J=4.2 Hz, —CH$_2$—×2), 2.6 (3H, s, —CH$_3$), 3.4 (2H, s, —CH$_2$—), 3.6 (4H, t, J=4.2 Hz, —CH$_3$—×2), 7.3 (2H, d, J=8.4 Hz, ArH), 7.4 (1H, d, J=4.1 Hz, ArH), 7.8 (2H, d, J=8.4 Hz, ArH), 8.2 (1H, d, J=4.1 Hz, ArH), 8.5 (1H, s, ArH), 9.7 (1H, s, —NHCO—), 10.4 (1H, s, —NH—), 13.5 (1H, s, Pyrazole).

Example 57

1. Experimental Materials

Reagents and materials: compound 1, mesylate of compound 1 (IS), compound 2, mesylate of compound 2 (2S), acetonitrile, ethyl acetate, methanol, chromatographic column Hypersil ODS (4.6 mm×200 mm, 5 mm), Centrifuge Tube, EP tube, pipette tip, rubber glove, syringe (1 mL) etc.

2. Instruments

Agilent 1200 HPLC (Agilent Technologies Co., ltd., USA), Model SHZ-88 Water Bath Constant Temperature Vibrator (Jintan Instrument Co., ltd., China), Model KQ3200DB Ultrasonic Cleaner (Kunshan Ultrasonic Instrument Co., ltd., China), Model UV-2102PCS Ultraviolet Spectrometry Photometer (Shanghai Longnike Instrument Co., ltd., China), Model TGL-16 Table Centrifuge (Shanghai Anting Science Instrument Co., ltd., China), Model XW-80A Vortex Mixers (Shanghai Jinke, China), Model PL203 Mettler Toledo Electronic Balance (Switzerland).

Animals: Male Wistar rats (weighing 200±20 g) (China Pharmaceutical University, China).

3. Measurement of Water Solubility

An excess quantity of sample was added into a 50 mL triangular flask, to which 10 mL distilled water was added, and then the flask was vibrated in a Constant Temperature Vibrator at 25° C. for 72 h. The solution was centrifuged at 10000 r/min for 15 min and then the supernatant was filtrated with 0.22 μM microfiltration membrane to remove undissolved drug. 2 mL filtrate was metered with methanol to 10 ml. The content of drug was determined with 20 μL sample injection. The results were shown in Table 3.

TABLE 3

Measurement of Water Solubility

| | Drug | | | |
|---|---|---|---|---|
| | Compound (I-1) | Compound (I-1-S) | Compound (I-2) | Compound (I-2-S) |
| Solubility ng/mL | <100 | 645 | <80 | 576 |

The results in table 3 show that water solubilities of compounds I-1 and I-2 increase when they form mesylates (I-1-S) and (I-2-S).

4. Measurement of Lipid-Water Partition Coefficient (Log P)

n-octanol and distilled water were allowed to saturate each other for 24 h. An amount of the sample was weighed accurately into a 50 mL volumetric flask and metered with n-octanol that was saturated with water (the sample was dissolved completely). A 10 mL solution of the sample in n-octanol was placed in a 50 mL triangular flask, to which was added 10 mL distilled water which was saturated with n-octanol. The mixture was equilibrated (125 rpm, 72 h) at 25° C. with a constant temperature vibrator. The lipid-water partition coefficient was calculated by the concentrations of the drug in the n-octanol stock solution before the experiment and in the n-octanol layer after experiment. The results were shown in Table 4.

TABLE 4

| | Lipid-Water Partition Coefficient (LogP) | | | |
|---|---|---|---|---|
| | Drug | | | |
| | Compound (I-1) | Compound (I-1-S) | Compound (I-2) | Compound (I-2-S) |
| LogP | 1.27 | 1.28 | 1.28 | 1.29 |

The results in table 4 show that the lipid-water partition coefficients (Log P) of compounds I-1 and I-2 have no significant difference compared with mesylates (I-1-S) and (I-2-S).

3. Stability Analysis
3.1 Plasma Sample Treatment

300 μL blood collected from the rat was mixed with 30 μL methanol and 2 mL ethyl acetate. The samples were vortexed for 3 min and centrifuged at 4000 rpm for 15 min. The supernatant was introduced into another centrifugal tube. The lower layer was repeatedly extracted and then the supernatants were combined and dried with nitrogen gas. After redissolution with 150 μL methanol, they were filtered by 0.22 μm membrane and then subjected to analysis with a injection volume of 20 μL.

3.2 Plasma Stability

The standard solution of the compounds (I-1 and I-2) were diluted with plasma, and collected at 0, 1, 2, 4, 6, 8, 12 and 24 h. The samples were prepared according to the method of 3.1. 20 μL were introduced into the HPLC system and the peak area is recorded for analysis to determine the stability of compound 1 and 2 in plasma. The results are shown in Table 5.

TABLE 5

| | Plasma stability | | | | | | | |
|---|---|---|---|---|---|---|---|---|
| Time(h) | 0 | 1 | 2 | 3 | 5 | 8 | 12 | 24 |
| Compound I-1 | 2.16 | 2.24 | 2.22 | 2.12 | 2.11 | 1.91 | 1.84 | 1.95 |
| Compound I-2 | 2.36 | 2.34 | 2.29 | 2.21 | 2.16 | 2.11 | 1.97 | 1.85 |

It can be seen that the compounds (I-1 and I-2) show good plasma stability in 24 h.

4. Experiment Animals
4.1 Experiment Design and Plasma Concentration-Time Data

An amount of compound was taken accurately to prepare CMC-Na aqueous solution containing 3 mg/mL of drug. 12 healthy male Wister rats were randomly assigned to two groups, each group including 6 rats. The first group was administrated orally compound 1. The second group was administrated orally compound 2. The doses were both 30 mg/kg (corresponding to 2 mL for each rat). The rats were fasting for 12 h before administration and free access to water. 0.6 mL blood samples were collected at 0.5, 1, 1.5, 2, 2.5, 3, 5, 8, 12 and 24 h after drug administration from the venous sinuses and added into EP tubes which were rinsed with heparin sodium previously. The samples were centrifuged at 4,000 r/min for 15 min and the upper plasma were obtained. 300 μL plasma was subjected to analysis and the chromatogram and peak area were recorded. The plasma concentrations of compounds 1 and 2 were calculated to give average concentration-time curve. Table 6 and 7 summarize the results.

TABLE 6

| Plasma concentration vs. time of rats after oral compound 1 (ng*ml/1) | | | | | | | | | | |
|---|---|---|---|---|---|---|---|---|---|---|
| Rat | time | | | | | | | | | |
| NO. | 0.5 | 1 | 1.5 | 2 | 2.5 | 3 | 5 | 8 | 12 | 24 |
| 1 | 65.08 | 73.81 | 82.09 | 100.94 | 113.35 | 125.86 | 115.59 | 233.26 | 153.29 | 167.23 |
| 2 | 76.41 | 81.17 | 82.19 | 86.23 | 104.16 | 78.87 | 172.92 | 151.83 | 135.94 | 133.16 |
| 3 | 80.51 | 80.91 | 81.99 | 86.97 | 106.91 | 266.46 | 127.6 | 271.51 | 110.59 | 79.81 |
| 4 | 76.52 | 90.92 | 92.66 | 132.81 | 158.41 | 191.06 | 232.81 | 205.77 | 162.93 | 123.91 |
| 5 | 68.85 | 104.54 | 88.06 | 113.55 | 100.48 | 149.67 | 174.04 | 157.03 | 107.83 | 126.6 |
| 6 | 68.95 | 65.58 | 77.48 | 97.96 | 96.8 | 112.43 | 159.33 | 150.59 | 135.84 | 105.83 |
| mean | 72.72 | 82.82 | 84.08 | 103.08 | 113.35 | 154.06 | 163.72 | 195 | 134.4 | 122.76 |
| sd | 5.94 | 13.58 | 5.38 | 17.71 | 22.79 | 66.64 | 41.48 | 50.42 | 22.13 | 29.1 |

TABLE 7

| Plasma concentration vs. time of rats after oral compound 2 (ng*ml/1) | | | | | | | | | | |
|---|---|---|---|---|---|---|---|---|---|---|
| Rat | time | | | | | | | | | |
| NO. | 0.5 | 1 | 1.5 | 2 | 2.5 | 3 | 5 | 8 | 12 | 24 |
| 1 | 25.98 | 28.68 | 42.95 | 37.16 | 57.6 | 57.21 | 86.12 | 119.66 | 229.22 | 209.56 |
| 2 | 24.36 | 18.66 | 33.31 | 47.57 | 39.48 | 41.79 | 78.03 | 82.66 | 256.32 | 221.75 |
| 3 | — | — | 40.25 | 47.03 | 49.89 | 65.08 | 94.32 | 121.59 | 213.94 | 74.79 |
| 4 | — | — | 45.26 | 46.08 | 51.04 | 53.93 | 76.64 | 186.27 | 286.97 | 138.91 |
| 5 | 29.26 | 208.71 | 48.34 | 53.04 | 72.86 | 81.11 | 124.06 | 196.61 | 252.66 | 198.92 |
| 6 | 123.49 | — | 57.05 | 88.44 | 74.79 | 87.89 | 272.93 | 263.95 | 345.56 | 97.83 |
| mean | 50.77 | 85.35 | 44.53 | 53.22 | 57.61 | 64.5 | 122.02 | 161.79 | 264.11 | 156.96 |
| sd | 48.52 | 106.95 | 7.98 | 18 | 13.85 | 17.34 | 75.93 | 66.18 | 47.08 | 62.13 |

4.2 Data Analysis

DAS 2.0 program was used to analyze plasma concentration vs. time data after s single oral dose (Table 6, 7). Fitting and the AIC methods were used to determine the model. The analysis was based on the principle that the larger fitting and the smaller AIC, the better model. The oral administration was consistent with the two-compartment model. The statistical distance parameter is used to compare the 2 compounds for the pharmacokinetic parameters. The results were set forth in Table 8.

TABLE 8

Pharmacokinetic parameters of the compounds 1 and 2 after oral administration in rats AUC: area under the plasma concentration-time curve; $T_{max}$: maximum time for drug peak; $T_{1/2}$: half-life; MRT: mean residence time; $C_{max}$: maximum concentration for drug peak

| Parameter | Compound I-1 | Compound I-2 |
|---|---|---|
| AUC 0-24(ng · ml/L) | 3345.7 ± 467.56 | 4346.9 ± 1298.0 |
| MRT 0-24 | 11.62 ± 1.09 | 13.76 ± 1.29 |
| $T_{max}$ | 5.5 ± 2.29 | 14 ± 5.29 |
| $T_{1/2}$ | 45.76 ± 29.12 | 14.67 ± 4.23 |
| $C_{max}$ (ng/mL) | 241.35 ± 102.97 | 265.35 ± 52.91 |

It can be seen from Table 8, the pharmacokinetic parameters of compound 1 and 2 are acceptable.

Example 58

Inhibition to S180 Grafting Tumor in Animal by the Drug

1. Experiment Materials and Animals

Test drug: compound I-1; Positive drug: AT7519, purchased from Jinan Great Chemical Co., Ltd.

Test animal: ICR mouse, clean grade, provided by Yangzhou University Medical center, License No: SCXK(Su) 2007-0001; 18-22 g, female; granule feed, provided by Jiangsu Xietong Organism Co., ltd.; Feeding conditions: air-conditioned room, 18-24° C., relative humidity 70%.

Tumor: S180, provided by Institute of Tumor Drug Research Jiangsu.

Instrument: YJ-875 Medical Microbench (Suzhou Medical Instrument).

2. Procedures

ICR mouse was inoculated with solid tumor according to tumor grafting process (tumor piece was weighed under sterile condition, homogenized with glass tissue homogenizer, placed within a sterile container, to which was added physiological saline to prepare 1:3 cell suspension. The container was placed on ice and aspirated and the cells were mixed homogeneously before each aspiration. Each mouse was inoculated subcutaneously 0.2 mL at right fore axilla). 24 h after inoculation, the mice were weighed and randomly divided into 5 groups, each group including 10 mice. Each of the drug group was administrated for the first time 24 h after inoculation (d1). The mice were administered intravenously, once a day and 7 administrations in total. The administration volume was 0.4 ml/20 g. The mice bearing tumor were sacrificed 8 days after inoculation (d8). The tumor tissue was separated and weighed. The data was analyzed with statistics method (t-test).

Dose setting: 5 groups in total.

Model control group; Positive control group: AT7519 15 mg/kg; Test drug: 30 mg/kg; Test drug: 15 mg/kg; Test drug: 7.5 mg/kg 4. Results

TABLE 1

Inhibition for S180 grafting Tumor by the drug ($\overline{X}$ ± SD)

| Group | dose (mg/kg) | Body weight(g) Before administration | Body weight(g) After administration | Animal Before experiment | Animal After experiment | Tumor weight (g) | Tumor inhibition (%) |
|---|---|---|---|---|---|---|---|
| Model control | — | 20.00 ± 2.35 | 25.00 ± 1.85 | 8 | 8 | 1.18 ± 0.28 | — |
| Test drug | 30 mg/kg | 19.88 ± 2.67 | 20.43 ± 3.20* | 8 | 7 | 0.52 ± 0.25** | 55.5 |
| Test drug | 15 mg/kg | 19.00 ± 1.00 | 20.00 ± 1.94* | 8 | 8 | 0.63 ± 0.11** | 45.2 |
| Test drug | 7.5 mg/kg | 18.63 ± 0.99 | 24.00 ± 0.75 | 8 | 8 | 0.74 ± 0.19* | 36.94 |
| Positive AT7519 | 15 mg/kg | 19.75 ± 1.85 | 23.83 ± 3.39 | 8 | 7 | 0.80 ± 0.27 | 32.45 |

*P < 0.05

**P < 0.01 (compared to the model control)

5. Conclusion

The results indicate that, compared to the model control group, the test drug (30 mg/kg and 15 mg/kg) has very significant inhibitory effect on S180 tumor growth (P<0.01), and the test drug (7.5 mg/kg) has significant inhibitory effect on S180 tumor growth (P<0.05). The test drug (30 mg/kg and 15 mg/kg) has significant inhibitory effect on the body weight of experimental animals (P<0.05).

The invention claimed is:
1. A compound defined by formula (I):

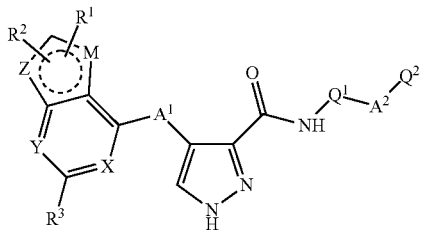

or a pharmaceutically acceptable salt or tautomer or solvate thereof or a combination thereof,
wherein:
$R^1$, $R^2$ and $R^3$ each independently represent H, alkyl, cyano, halogen, haloalkyl, hydroxyl, thiol, alkoxyl, alkylthiol, alkoxylalkyl, aralkyl, diarylalkyl, aryl or Het;
X and Y each independently represent N atom or CH group, wherein the CH group can optionally be substituted by $R^4$, and $R^4$ may be H, alkyl, cyano, halogen, haloalkyl, hydroxyl, thiol, alkoxyl, alkylthiol, alkoxylalkyl, aralkyl, diarylalkyl, aryl or Het;
Z and M each independently represent NH, O, S or CH group with the proviso that one of Z and M is NH, O or S, wherein the CH or NH group can each optionally and independently be substituted by $R^5$, and $R^5$ may be H, alkyl, cyano, halogen, haloalkyl, hydroxyl, thiol, alkoxyl, alkylthiol, alkoxylalkyl, aralkyl, diarylalkyl, aryl or Het;
$A^1$ independently represents NH, O, S or alkylene group, wherein the NH or alkylene group can each optionally and independently be substituted by $R^6$, and $R^6$ may be H, alkyl, cyano, halogen, haloalkyl, hydroxyl, thiol, alkoxyl, alkylthiol, alkoxylalkyl, aralkyl, diarylalkyl, aryl or Het;
$A^2$ independently represents alkylene, C(O)NH, C(O), NHC(O), alkylene-C(O), C(O)-alkylene, alkylene-C(O)-alkylene or NHC(O)NH, wherein the above groups can each optionally and independently be substituted by $R^7$, and $R^7$ may be H, alkyl, cyano, halogen, haloalkyl, hydroxyl, thiol, alkoxyl, alkylthiol, alkoxylalkyl, aralkyl, diarylalkyl, aryl or Het;
$Q^1$ is selected from aryl and Het, wherein the aryl or Het can each optionally and independently be substituted by one or more $R^8$, and $R^8$ may be H, alkyl, cyano, halogen, haloalkyl, hydroxyl, thiol, alkoxyl, alkylthiol, alkoxylalkyl, aralkyl, diarylalkyl, aryl or Het;
$Q^2$ is selected from aryl or Het, wherein the aryl or Het can each optionally and independently be substituted by one or more $R^9$, and $R^9$ may be H, alkyl, cyano, halogen, haloalkyl, hydroxyl, thiol, alkoxyl, alkylthiol, alkoxylalkyl, aralkyl, diarylalkyl, aryl and Het; and
wherein:
the alkyl refers to a linear or branched chain saturated hydrocarbon group having 1-6 carbon atoms, or a cyclic saturated hydrocarbon group having 3-6 carbon atoms, or a cyclic saturated hydrocarbon group having 3-6 carbon atoms which is attached to a linear or branched chain saturated hydrocarbon group having 1-6 carbon atoms;
the alkylene refers to a linear or branched chain saturated hydrocarbon group having 1-6 carbon atoms, or a cyclic saturated hydrocarbon group having 3-6 carbon atoms, or a cyclic saturated hydrocarbon group having 3-6 carbon atoms which is attached to a linear or branched chain saturated hydrocarbon group having 1-6 carbon atoms; wherein one hydrogen atom is absent;
the alkoxyl refers to a linear or branched chain saturated hydrocarbon group having 1-6 carbon atoms, or a cyclic saturated hydrocarbon group having 3-6 carbon atoms, or a cyclic saturated hydrocarbon group having 3-6 carbon atoms which is attached to a linear or branched chain saturated hydrocarbon group having 1-6 carbon atoms; wherein each carbon atom is optionally substituted by oxygen;
the alkylthiol refers to a linear or branched chain saturated hydrocarbon group having 1-6 carbon atoms, or a cyclic saturated hydrocarbon group having 3-6 carbon atoms, or a cyclic saturated hydrocarbon group having 3-6 carbon atoms which is attached to a linear or branched chain saturated hydrocarbon group having 1-6 carbon atoms; wherein each carbon atom is optionally substituted by sulfur;
the alkoxylalkyl refers to the alkyl group as defined above, which is attached to the alkoxyl group as defined above;
the aryl refers to a carbonic ring selected from phenyl, naphthyl, acenaphthenyl and tetralyl, which may be each optionally substituted by 1, 2 or 3 substituents each independently selected from H, alkyl, cyano, halogen, haloalkyl, hydroxyl, thiol, alkoxyl, alkylthiol, alkoxylalkyl, aralkyl, diarylalkyl, aryl and Het;
the aralkyl or diarylalkyl refers to the alkyl group as defined above, which is attached to the aryl group as defined above;
the Het refers to a monocyclic heterocycle group selected from piperidyl, pyrrolyl, pyrazolyl, imidazolyl, furyl, thienyl, oxazolyl, isoxazolyl, thiazolyl, isothiazolyl, pyridyl, pyrimidinyl, pyrazinyl and pyridazinyl, or a bicyclic heterocycle group selected from quinolyl, quinoxalinyl, indolyl, benzimidazolyl, benzoxazolyl, benzisoxazolyl, benzothiazolyl, benzisothiazolyl, benzofuryl, benzothienyl, 2,3-dihydro-1,4-benzodioxinyl and 1,3-benzodioxolyl; wherein the monocyclic or bicyclic heterocycle group is each optionally substituted by 1, 2 or 3 substituents each independently selected from halogen, haloalkyl, hydroxyl, alkyl and alkoxyl;
the halogen refers to a substituent selected from fluoro, chloro, bromo and iodo;
the haloalkyl refers to a linear or branched chain saturated hydrocarbon group having 1-6 carbon atoms, or a cyclic saturated hydrocarbon group having 3-6 carbon atoms, or a cyclic saturated hydrocarbon group having 3-6 carbon atoms which is attached to a linear or branched chain saturated hydrocarbon group having 1-6 carbon atoms; wherein one or more carbon atoms are substituted by one or more halogens.
2. The compound according to claim 1, wherein:
$R^1$, $R^2$ and $R^3$ each independently represent H, alkyl, cyano, halogen, haloalkyl, hydroxyl, thiol, alkoxyl, alkylthiol, alkoxylalkyl, aralkyl or aryl;
X and Y each independently represent N atom or CH group, wherein the CH group can optionally be substituted by $R^4$, and $R^4$ may be H, alkyl, cyano halogen, haloalkyl, hydroxyl, thiol, alkoxyl, alkylthiol, alkoxylalkyl, aralkyl or aryl;

Z and M each independently represent NH, O, S or CH group with the proviso that one of Z and M is NH, O or S, wherein the CH or NH group can each optionally and independently be substituted by $R^5$, and $R^5$ may be H, alkyl, cyano, halogen, haloalkyl, hydroxyl, thiol, alkoxyl, alkylthiol, alkoxylalkyl, aralkyl or aryl;

$A^1$ independently represents NH, O, S or alkylene group, wherein the NH or alkylene group can each optionally and independently be substituted by $R^6$, and $R^6$ may be H, alkyl, cyano, halogen, haloalkyl, hydroxyl, thiol, alkoxyl, alkylthiol, alkoxylalkyl, aralkyl or aryl;

$A^2$ independently represents alkylene, C(O)NH, C(O), NHC(O), alkylene-C(O), C(O)-alkylene, alkylene-C(O)-alkylene or NHC(O)NH, wherein the above groups can each optionally and independently be substituted by $R^7$, and $R^7$ may be H, alkyl, cyano, halogen, haloalkyl, hydroxyl, thiol, alkoxyl, alkylthiol, alkoxylalkyl, aralkyl or aryl;

$Q^1$ is selected from aryl and Het, wherein the aryl and Het can each optionally and independently be substituted by one or more $R^8$, and $R^8$ may be H, alkyl, cyano, halogen, haloalkyl, hydroxyl, thiol, alkoxyl, alkylthiol, alkoxylalkyl, aralkyl or aryl;

$Q^2$ is selected from aryl and Het, wherein the aryl and Het can each optionally and independently be substituted by one or more $R^9$, and $R^9$ may be H, alkyl, cyano, halogen, haloalkyl, hydroxyl, thiol, alkoxyl, alkylthiol, alkoxylalkyl, aralkyl or aryl.

3. The compound according to claim 2, wherein:

$R^1$, $R^2$ and $R^3$ each independently represent H, alkyl, cyano, halogen, haloalkyl, hydroxyl, thiol, alkoxyl, alkylthiol or alkoxylalkyl;

X and Y each independently represent N atom or CH group, wherein the CH group can optionally be substituted by $R^4$, and $R^4$ may be H, alkyl, cyano, halogen, haloalkyl, hydroxyl, thiol, alkoxyl, alkylthiol or alkoxylalkyl;

Z and M each independently represent NH, O, S or CH group with the proviso that one of Z and M is NH, O or S, wherein the CH or NH group can each optionally and independently be substituted by $R^5$, and $R^5$ may be H, alkyl, cyano, halogen, haloalkyl, hydroxyl, thiol, alkoxyl, alkylthiol or alkoxylalkyl;

$A^1$ independently represents NH, O, S or alkylene group, wherein the NH or alkylene group can each optionally and independently be substituted by $R^6$, and $R^6$ may be H, alkyl, cyano, halogen, haloalkyl, hydroxyl, thiol, alkoxyl, alkylthiol or alkoxylalkyl;

$A^2$ independently represents alkylene, C(O)NH, C(O), NHC(O), alkylene-C(O), C(O)-alkylene, alkylene-C(O)-alkylene or NHC(O)NH, wherein the above groups can each optionally and independently be substituted by $R^7$, and $R^7$ may be H, alkyl, cyano, halogen, haloalkyl, hydroxyl, thiol, alkoxyl, alkylthiol or alkoxylalkyl;

$Q^1$ is selected from aryl and Het, wherein the aryl and Het can each optionally and independently be substituted by one or more $R^8$, and $R^8$ may be H, alkyl, cyano, halogen, haloalkyl, hydroxyl, thiol, alkoxyl, alkylthiol or alkoxylalkyl;

$Q^2$ is selected from aryl and Het, wherein the aryl and Het can each optionally and independently be substituted by one or more $R^9$, and $R^9$ may be H, alkyl, cyano, halogen, haloalkyl, hydroxyl, thiol, alkoxyl, alkylthiol or alkoxylalkyl.

4. The compound according to claim 3, wherein:

$R^1$, $R^2$ and $R^3$ each independently represent H, alkyl, cyano, halogen, haloalkyl, hydroxyl, thiol, alkoxyl, alkylthiol or alkoxylalkyl;

X and Y each independently represent N atom or CH group, wherein the CH group can optionally be substituted by $R^4$, and $R^4$ may be H, alkyl, cyano, halogen, haloalkyl, hydroxyl, thiol, alkoxyl, alkylthiol or alkoxylalkyl;

Z and M each independently represent NH, O, S or CH group with the proviso that one of Z and M is NH, O or S, wherein the CH or NH group can each optionally and independently be substituted by $R^5$, and $R^5$ may be H, alkyl, cyano, halogen, haloalkyl, hydroxyl, thiol, alkoxyl, alkylthiol or alkoxylalkyl;

$A^1$ independently represents NH, O, S or alkylene group, wherein the NH or alkylene group can each optionally and independently be substituted by $R^6$, and $R^6$ may be H, alkyl, cyano, halogen, haloalkyl, hydroxyl, thiol, alkoxyl, alkylthiol or alkoxylalkyl;

$A^2$ independently represents alkylene, C(O)NH, C(O), NHC(O), alkylene-C(O), C(O)-alkylene, alkylene-C(O)-alkylene or NHC(O)NH, wherein the above groups can each optionally and independently be substituted by $R^7$, and $R^7$ may be H, alkyl, cyano, halogen, haloalkyl, hydroxyl, thiol, alkoxyl, alkylthiol or alkoxylalkyl;

$Q^1$ is unsubstituted or substituted aromatic ring selected from phenyl, naphthyl, pyrrolyl, furyl, thienyl, pyridyl, pyrazinyl and pyrimidinyl, and the above groups can each optionally and independently be substituted by one or more $R^8$, and $R^8$ may be H, alkyl, cyano, halogen, haloalkyl, hydroxyl, thiol, alkoxyl, alkylthiol or alkoxylalkyl;

$Q^2$ is aromatic ring selected from phenyl, naphthyl, pyrazolyl, furyl, thienyl, pyridyl, pyrazinyl, and pyrimidinyl; or $C_3$-$C_8$ aliphatic carbonic ring; or aliphatic heterocycle ring selected from tetrahydropyrrolyl, piperidyl, morpholinyl, and methylpiperazinyl; and the above groups can each optionally and independently be substituted by one or more $R^8$, and $R^8$ may be H, alkyl, cyano, halogen, haloalkyl, hydroxyl, thiol, alkoxyl, alkylthiol or alkoxylalkyl.

5. The compound according to claim 4, wherein:

$R^1$, $R^2$ and $R^3$ each independently represent H, alkyl, cyano, halogen, haloalkyl, hydroxyl, thiol, alkoxyl, alkylthiol or alkoxylalkyl;

X and Y each independently represent N atom or CH group, wherein the CH group can optionally be substituted by $R^4$, and $R^4$ may be H, alkyl, cyano, halogen, haloalkyl, hydroxyl, thiol, alkoxyl, alkylthiol or alkoxylalkyl;

Z and M each independently represent NH, O, S or CH group with the proviso that one of Z and M is NH, O or S, wherein the CH or NH group can each optionally and independently be substituted by $R^5$, and $R^5$ may be H, alkyl, cyano, halogen, haloalkyl, hydroxyl, thiol, alkoxyl, alkylthiol or alkoxylalkyl;

$A^1$ independently represents NH, O, S or alkylene group, wherein the NH or alkylene group can each optionally and independently be substituted by $R^6$, and $R^6$ may be H, alkyl, cyano, halogen, haloalkyl, hydroxyl, thiol, alkoxyl, alkylthiol or alkoxylalkyl;

A² independently represents alkylene, C(O)NH, C(O), NHC(O), alkylene-C(O), C(O)-alkylene, alkylene-C(O)-alkylene or NHC(O)NH, wherein the above groups can each optionally and independently be substituted by R⁷, and R⁷ may be H, alkyl, cyano, halogen, haloalkyl, hydroxyl, thiol, alkoxyl, alkylthiol or alkoxylalkyl;

Q¹ is unsubstituted or substituted aromatic ring selected from phenyl, naphthyl, pyrrolyl, furyl, thienyl, pyridyl, pyrazinyl and pyrimidinyl and the substituent may be 1-2 halogen or trifluoromethyl;

Q² is aromatic ring selected from phenyl, naphthyl, pyrazolyl, furyl, thienyl, pyridyl, pyrazinyl, and pyrimidinyl; or $C_3$-$C_8$ aliphatic carbonic ring; or aliphatic heterocycle ring selected from tetrahydropyrrolyl, piperidyl, morpholinyl, and methylpiperazinyl.

6. The compound according to claim 5, wherein:
R¹, R² and R³ each independently represent H and $C_{1-4}$ alkyl;
X and Y each independently represent N atom or CH group;
Z and M each independently represent NH, O, S or CH group with the proviso that one of Z and M is NH, O or S;
A¹ independently represents NH, O, S or CH₂ group;
A² independently represents chainlike $C_{1-4}$ alkylene, C(O)NH, C(O) or NHC(O);
Q¹ is unsubstituted or substituted aromatic ring selected from phenyl, naphthyl, pyrrolyl, furyl, thienyl, pyridyl, pyrazinyl or pyrimidinyl and the substituent may be 1-2 halogen or trifluoromethyl;
Q² is aromatic ring selected from phenyl, naphthyl, pyrazolyl, furyl, thienyl, pyridyl, pyrazinyl, pyrimidinyl; or $C_3$-$C_6$ aliphatic carbonic ring; or aliphatic heterocycle ring selected from tetrahydropyrrolyl, piperidyl, morpholinyl, and methylpiperazinyl.

7. The compound according to claim 6, wherein:
R¹, R² and R³ each independently represent H or methyl;
A¹ represents NH;
A² represents CH₂;
Q¹ represents phenyl;
Q² represents morpholinyl or methylpiperazinyl.

8. The compound according to claim 1, which is selected from:

4-(4-thieno[2,3-d]pyrimidinylamino)-N-((4-methyl-1-piperazinyl)methyl)phenyl)-1H-3-pyrazolecarboxamide (I-1)

4-(4-thieno[2,3-d]pyrimidinylamino)-N-(4-((4-morpholinyl)methyl)phenyl)-1H-3-pyrazolecarboxamide (I-2)

4-(4-(6-methylthieno[2,3-d]pyrimidinyl)amino)-N-(4-((4-methyl-1-piperazinyl)methyl)phenyl)-1H-3-pyrazolecarboxamide (I-3)

4-(4-(6-methylthieno[2,3-d]pyrimidinyl)amino)-N-(4-((4-morpholinyl)methyl)phenyl)-1H-3-pyrazolecarboxamide (I-4)

4-(4-(5-methylthieno[2,3-d]pyrimidinyl)amino)-N-(4-((4-methyl-1-piperazinyl)methyl)phenyl)-1H-3-pyrazolecarboxamide (I-5)

4-(4-(5-methylthieno[2,3-d]pyrimidinyl)amino)-N-(4-((4-morpholinyl)methyl)phenyl)-1H-3-pyrazolecarboxamide (I-6)

4-(4-(5,6-dimethylthieno[2,3-d]pyrimidinyl)amino)-N-(4-((4-methyl-1-piperazinyl)methyl)phenyl)-1H-3-pyrazolecarboxamide (I-7)

4-(4-(5,6-dimethylthieno[2,3-d]pyrimidinyl)amino)-N-(4-((4-morpholinyl)methyl)phenyl)-1H-3-pyrazolecarboxamide (I-8)

4-(4-thieno[3,2-d]pyrimidinylamino)-N-(4-((4-methyl-1-piperazinyl)methyl)phenyl)-1H-3-pyrazolecarboxamide (I-9)

4-(4-thieno[3,2-d]pyrimidinylamino)-N-(4-((4-morpholinyl)methyl)phenyl)-1H-3-pyrazolecarboxamide (I-10)

4-(4-(7H-pyrrolo[2,3-d]pyrimidinyl)amino)-N-(4-((4-methyl-1-piperazinyl)methyl)phenyl)-1H-3-pyrazolecarboxamide (I-11)

4-(4-(7H-pyrrolo[2,3-d]pyrimidinyl)amino)-N-(4-((4-morpholinyl)methyl)phenyl)-1H-3-pyrazolecarboxamide (I-12)

4-(4-(6-methyl-7H-pyrrolo[2,3-d]pyrimidinyl)amino)-N-(4-((4-methyl-1-piperazinyl)methyl)phenyl)-1H-3-pyrazolecarboxamide (I-13)

4-(4-(6-methyl-7H-pyrrolo[2,3-d]pyrimidinyl)amino)-N-(4-((4-morpholinyl)methyl)phenyl)-1H-3-pyrazolecarboxamide (I-14)

4-(4-(5-methyl-7H-pyrrolo[2,3-d]pyrimidinyl)amino)-N-(4-((4-methy-1-piperazinyl)methyl)phenyl)-1H-3-pyrazolecarboxamide (I-15)

4-(4-(5-methyl-7H-pyrrolo[2,3-d]pyrimidinyl)amino)-N-(4-((4-morpholinyl)methyl)phenyl)-1H-3-pyrazolecarboxamide (I-16)

4-(4-(5H-pyrrolo[3,2-d]pyrimidinyl)amino)-N-(4-((4-methyl-1-piperazinyl)methyl)phenyl)-1H-3-pyrazolecarboxamide (I-17)

4-(4-(5H-pyrrolo[3,2-d]pyrimidinyl)amino)-N-(4-((4-morpholinyl)methyl)phenyl)-1H-3-pyrazolecarboxamide (I-18)

4-(4-(6-methyl-5H-pyrrolo[3,2-d]pyrimidinyl)amino)-N-(4-((4-methyl-1-piperazinyl)methyl)phenyl)-1H-3-pyrazolecarboxamide (I-19)

4-(4-(6-methyl-5H-pyrrolo[3,2-d]pyrimidinyl)amino)-N-(4-((4-morpholinyl)methyl)phenyl)-1H-3-pyrazolecarboxamide (I-20)

4-(4-furo[2,3-d]pyrimidinylamino)-N-(4-((4-methy-1-piperazinyl)methyl)phenyl)-1H-3-pyrazolecarboxamide (I-21)

4-(4-furo[2,3-d]pyrimidinylamino)-N-(4-((4-morpholinyl)methyl)phenyl)-1H-3-pyrazolecarboxamide (I-22)

4-(4-furo[3,2-d]pyrimidinylamino)-N-(4-((4-methyl-1-piperazinyl)methyl)phenyl)-1H-3-pyrazolecarboxamide (I-23)

4-(4-furo[3,2-d]pyrimidinylamino)-N-(4-((4-morpholinyl)methyl)phenyl)-1H-3-pyrazolecarboxamide (I-24)

4-(4-thieno[3,2-c]pyridylamino)-N-(4-((4-methyl)-1-piperazinyl)methyl)phenyl)-1H-3-pyrazolecarboxamide (I-25)

4-(4-thieno[3,2-c]pyridylamino)-N-(4-((4-morpholinyl)methyl)phenyl)-1H-3-pyrazolecarboxamide (I-26)

4-(4-(2-methylthieno[3,2-c]pyridyl)amino)-N-(4-((4-methyl-1-piperazinyl)methyl)phenyl)-1H-3-pyrazolecarboxamide (I-27)

4-(4-(2-methylthieno[3,2-c]pyridyl)amino)-N-(4-((4-morpholinyl)methyl)phenyl)-1H-3-pyrazolecarboxamide (I-28)

4-(7-thieno[2,3-c]pyridylamino)-N-(4-((4-methyl-1-piperazinyl)methyl)phenyl)-1H-3-pyrazolecarboxamide (I-29)

4-(7-thieno[2,3-c]pyridylamino)-N-(4-((4-morpholinyl)methyl)phenyl)-1H-3-pyrazolecarboxamide (I-30)

4-(7-(3-methylthieno[2,3-c]pyridyl)amino)-N-(4-((4-methyl-1-piperazinyl)methyl)phenyl)-1H-3-pyrazolecarboxamide (I-31)

4-(7-(3-methylthieno[2,3-c]pyridyl)amino)-N-(4-((4-morpholinyl)methyl)phenyl)-1H-3-pyrazolecarboxamide (I-32)

4-(4-furo[3,2-c]pyridylamino)-N-(4-((4-methyl-1-piperazinyl)methyl)phenyl)-1H-3-pyrazolecarboxamide (I-33)

4-(4-furo[3,2-c]pyridylamino)-N-(4-((4-morpholinyl)methyl)phenyl)-1H-3-pyrazolecarboxamide (I-34)

4-(4-(2-methylfuro[3,2-c]pyridyl)amino)-N-(4-((4-methyl-1-piperazinyl)methyl)phenyl)-1H-3-pyrazolecarboxamide (I-35)

4-(4-(2-methylfuro[3,2-c]pyridyl)amino)-N-(4-((4-morpholinyl)methyl)phenyl)-1H-3-pyrazolecarboxamide (I-36)

4-(7-furo[2,3-c]pyridylamino)-N-(4-((4-methyl-1-piperazinyl)methyl)phenyl)-1H-3-pyrazolecarboxamide (I-37)

4-(7-furo[2,3-c]pyridylamino-N-(4-((4-morpholinyl)methyl)phenyl)-1H-3-pyrazolecarboxamide (I-38)

4-(7-furo[3,2-b]pyridylamino)-N-(4-((4-methyl-1-piperazinyl)methyl)phenyl)-1H-3-pyrazolecarboxamide (I-39)

4-(7-furo[3,2-b]pyridylamino)-N-(4-((4-morpholinyl)methyl)phenyl)-1H-3-pyrazolecarboxamide (I-40)

4-furo[2,3-b]pyridylamino)-N-(4-((4-methyl-1-piperazinyl)methyl)phenyl)-1H-3-pyrazolecarboxamide (I-41)

4-(4-furo[2,3-b]pyridylamino)-N-(4-((4-morpholinyl)methyl)phenyl)-1H-3-pyrazolecarboxamide (I-42)

4-(7-(1H-pyrrolo[2,3-c]pyridyl)amino)-N-(4-((4-methyl-1-piperazinyl)methyl)phenyl)-1H-3-pyrazolecarboxamide (I-43)

4-(7-(1H-pyrrolo[2,3-c]pyridyl)amino)-N-(4-((4-morpholinyl)methyl)phenyl)-1H-3-pyrazolecarboxamide (I-44)

4-(7-(2-methy-1H-pyrrolo[2,3-c]pyridyl)amino)-N-(4-((4-methyl-1-piperazinyl)methyl)phenyl)-1H-3-pyrazolecarboxamide (I-45)

4-(7-(2-methyl-1H-pyrrolo[2,3-c]pyridyl)amino)-N-(4-((4-morpholinyl)methyl)phenyl)-1H-3-pyrazolecarboxamide (I-46)

4-(4-(2-methylthieno[3,2-d]pyrimidine)ylamino)-N-(4-((4-methyl-1-piperazinyl)methyl)phenyl)-1H-3-pyrazolecarboxamide (I-47) and 4-(4-(2-methylthieno[3,2-d]pyrimidine)ylamino)-N-(4-((4-morpholinyl)methyl)phenyl)-1H-3-pyrazolecarboxamide (I-48).

9. The compound according to claim 1 or the pharmaceutically acceptable salt thereof, wherein the pharmaceutically acceptable salt is the acid addition salt formed by the compound of formula (I) with one of the following acids; hydrochloric acid, hydrobromic acid, sulfuric acid, phosphoric acid, methanesulfonic acid, benzenesulfonic acid, p-toluenesulfonic acid, naphthalenesulfonic acid, citric acid, tartaric acid, lactic acid, pyruvic acid, acetic acid, maleic acid or succinic acid, fumaric acid, salicylic acid, phenyl acetic acid, amygdalic acid; and the acidic salts of inorganic base.

10. A pharmaceutical composition comprising the compound according to claim 1 and a pharmaceutically acceptable carrier.

11. A method for treating a clinical disease mediated by CDK2 and Aurora A in a subject in need thereof, comprising administrating the compound according to claim 1 to the subject.

12. The method according to claim 11, wherein the disease is melanoma, liver cancer, kidney cancer, acute leukemia, non-small cell lung cancer, prostate cancer, thyroid cancer, skin cancer, colorectal cancer, pancreatic cancer, ovarian cancer, breast cancer, myelodysplastic syndrome, esophageal cancer, gastrointestinal cancer or mesothelioma.

13. A method for treating a clinical disease medicated by CMGC family and TK family kinases in a subject in need thereof, comprising administrating the compound according to claim 1 to the subject.

14. A method for treating a clinical disease medicated by GSK3b, FLT3, KDR, VEGFR in a subject in need thereof, comprising administrating the compound according to claim 1 to the subject.

15. The method according to claim 14, wherein the clinical disease is inflammation, virus infection, Type II diabetes mellitus or non-insulin-dependent diabetes mellitus, autoimmune disease, head trauma, stroke, epilepsy, Alzheimer's disease or motor neuron disease.

16. The compound according to claim 1 for use as an antifungal agent.

* * * * *

UNITED STATES PATENT AND TRADEMARK OFFICE
CERTIFICATE OF CORRECTION

PATENT NO.       : 9,550,792 B2  
APPLICATION NO.  : 14/759516  
DATED            : January 24, 2017  
INVENTOR(S)      : Tao Lu et al.

Page 1 of 1

It is certified that error appears in the above-identified patent and that said Letters Patent is hereby corrected as shown below:

In the Claims

Claim 8, Column 56, Lines 62-64:
"4-(7-(3-methylthieno[2, 3-c]pyridyl)amino)-N-(4-((4-methyl-1-piperazinyl)methyl)phenyl)-1H-3-pyrazolecarboxamide"

Should read:
--4-(7-(3-methylthieno[2,3-c]pyridyl)amino)-N-(4-((4-methyl-1-piperazinyl)methyl)phenyl)-1H-3-pyrazolecarboxamide--.

Signed and Sealed this  
Twenty-fifth Day of April, 2017

Michelle K. Lee  
*Director of the United States Patent and Trademark Office*